(12) United States Patent
Ranjbar et al.

(10) Patent No.: US 8,805,663 B2
(45) Date of Patent: Aug. 12, 2014

(54) SOLUTION NAVIER-STOCKS EQUATIONS OF THE BLOOD AS A NON-NEWTONIAN FLUID IN THE LEFT VENTRICLE

(76) Inventors: Saeed Ranjbar, Tehran (IR); Mersedeh Karvandi, Theran (IR); Mahdi Ajzachi, Tehran (IR)

( * ) Notice: Subject to any disclaimer, the term of this patent is extended or adjusted under 35 U.S.C. 154(b) by 553 days.

(21) Appl. No.: 13/046,797

(22) Filed: Mar. 14, 2011

(65) Prior Publication Data
US 2011/0166467 A1   Jul. 7, 2011

Related U.S. Application Data

(60) Provisional application No. 61/345,615, filed on May 18, 2010, provisional application No. 61/434,970, filed on Jan. 21, 2011, provisional application No. 61/434,979, filed on Jan. 21, 2011.

(51) Int. Cl.
G06G 7/60 (2006.01)
A61B 5/02 (2006.01)

(52) U.S. Cl.
USPC .................................. 703/11; 703/2; 600/508

(58) Field of Classification Search
USPC ......................................... 600/508; 703/2, 11
See application file for complete search history.

(56) References Cited

U.S. PATENT DOCUMENTS

| 6,674,879 B1 * | 1/2004 | Weisman et al. ............. 382/128 |
| 2008/0319308 A1 * | 12/2008 | Tang ............................. 600/416 |
| 2010/0298719 A1 * | 11/2010 | Kock et al. .................... 600/485 |
| 2011/0144967 A1 * | 6/2011 | Adirovich ....................... 703/11 |

OTHER PUBLICATIONS

Bacanni, Bernardo et al. "Fluid dynamics of the left ventricular filling in dilated cardiomyopathy". Dec. 28, 2001. Journal of Biomechanics. 35 (2002). p. 665-671.*
Baccani, Bernardo et al. "Fluid dynamics of the left ventricular filling in dilated cardiomyopathy". Dec. 28, 2001. Journal of Biomechanics. 35 (2002). p. 665-671.*

* cited by examiner

*Primary Examiner* — Christopher D Koharski
*Assistant Examiner* — Michael Carey
(74) *Attorney, Agent, or Firm* — Barry Choobin; Patent 360 LLC

(57) ABSTRACT

The present invention discloses a method for solving the Navier-Stokes equation of blood dynamics as a Non-Newtonian fluid in the left ventricle. The method seeks to provide a model of the model of myocardial motion as an elastic membrane. This invention provides a new method to study the blood flow inside a biological membrane, estimated using quadratic equations.

10 Claims, 40 Drawing Sheets

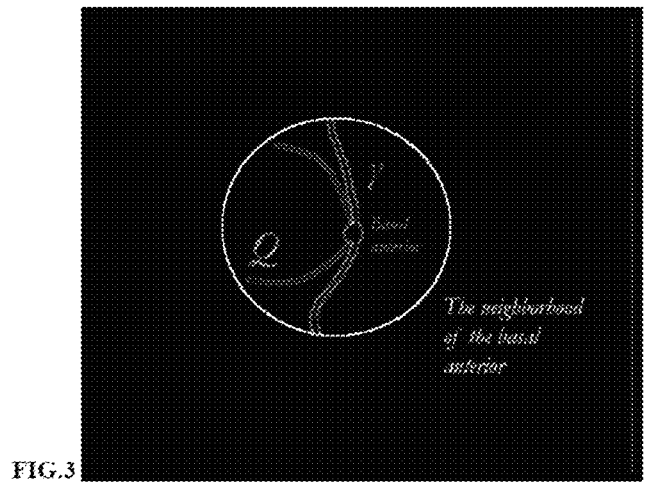
FIG.3
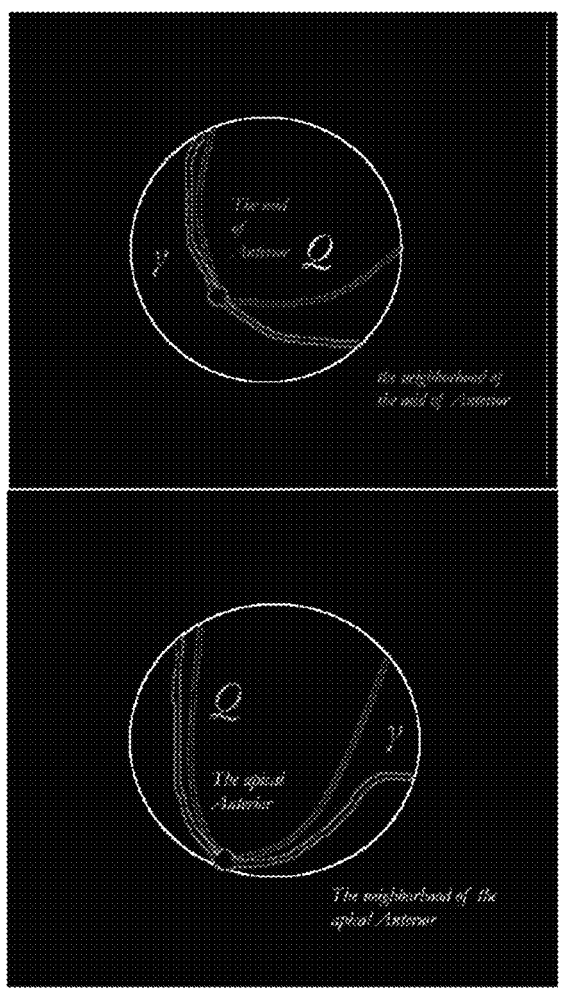

FIG.19
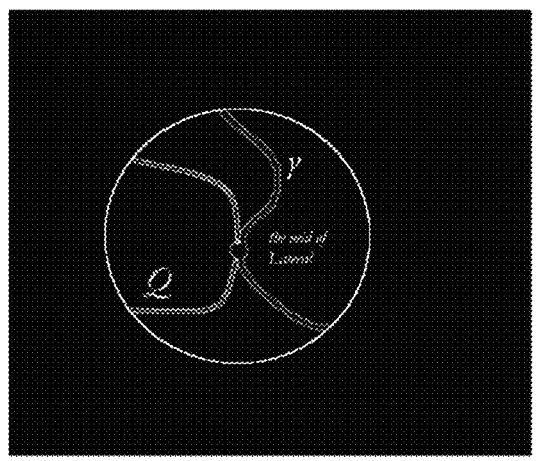
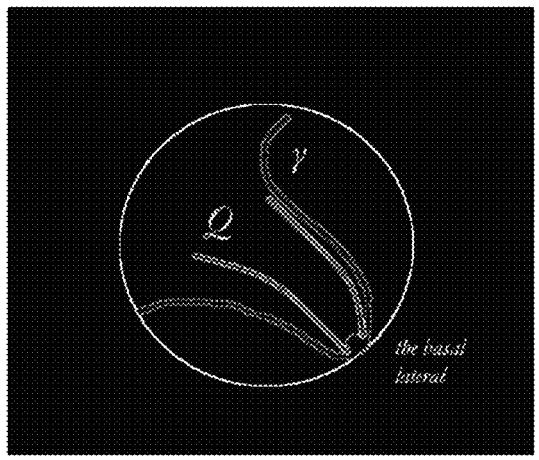

FIG.34

The blood flow curve in the region $O_{P_{bA}}$

The blood flow curve in the region $O_{P_{mA}}$

The blood flow curve in the region $O_{P_{aA}}$

The blood flow curve in the region $O_{P_{aI}}$

The blood flow curve in the region $O_{P_{mI}}$

The blood flow curve in the region $O_{P_{bI}}$

The blood flow curve in the region $O_{P_{bL}}$

The blood flow curve in the region $O_{P_{mL}}$

The blood flow curve in the region $O_{P_{aL}}$

The blood flow curve in the region $O_{P_{aS}}$

The blood flow curve in the region $O_{P_{mS}}$

The blood flow curve in the region $O_{P_{bS}}$

*We have a scheme of the blood flow curve inside the left ventricle where is made by gluing together of the above local schemes of the blood flow curves near the echocardiography samples*

FIG.37
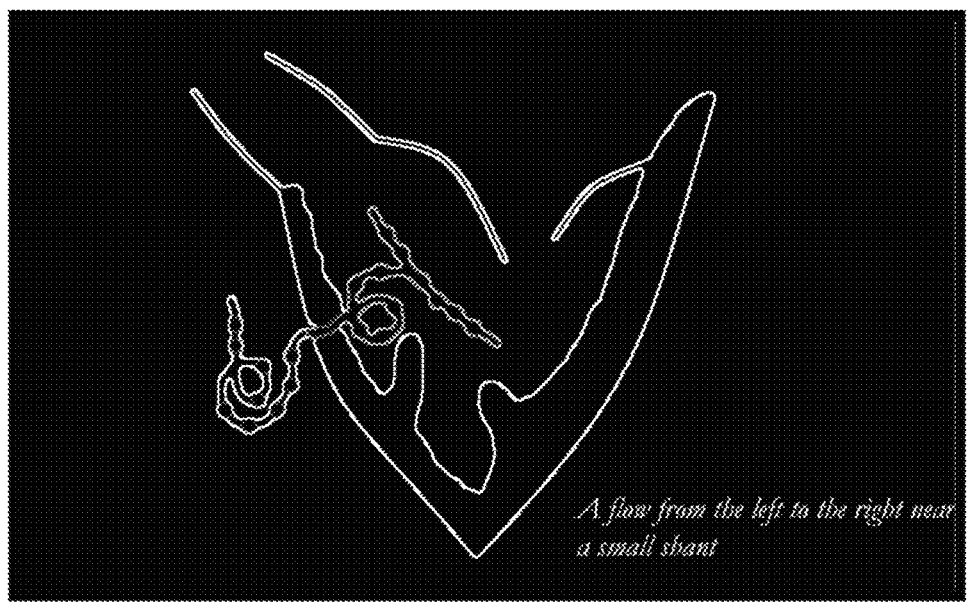
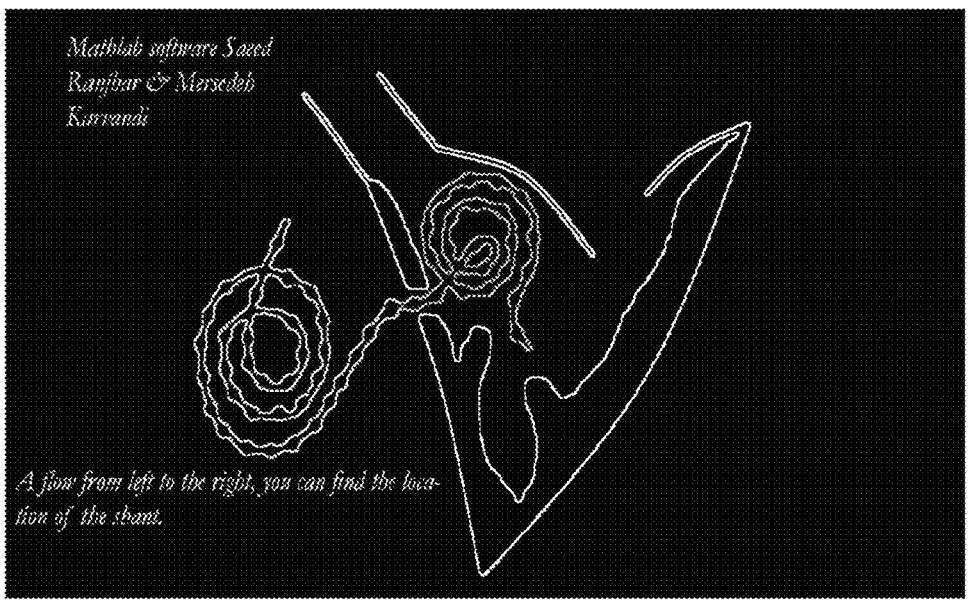

FIG.38
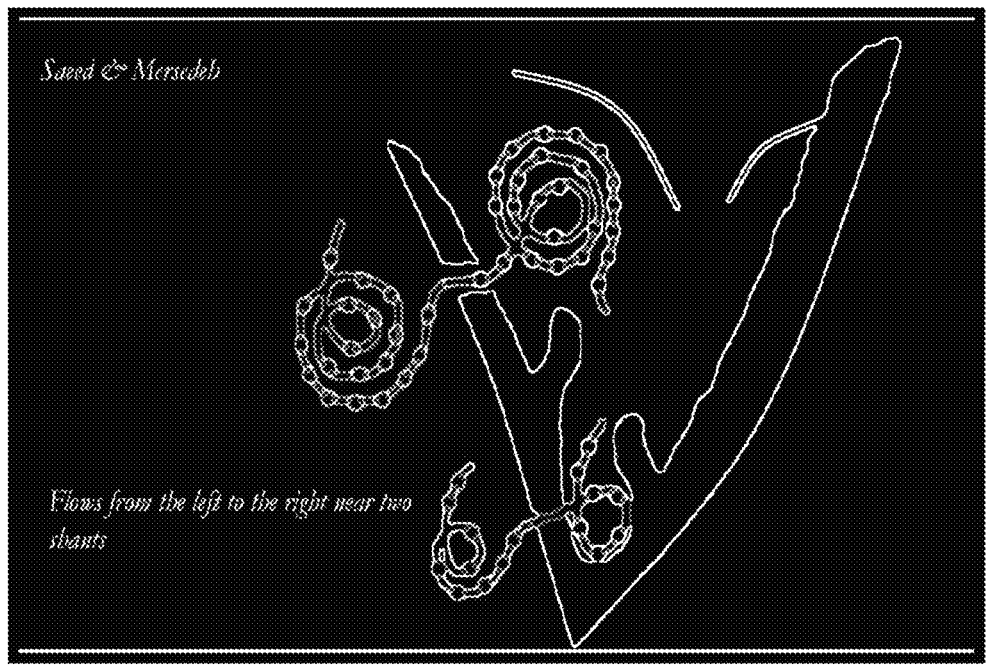
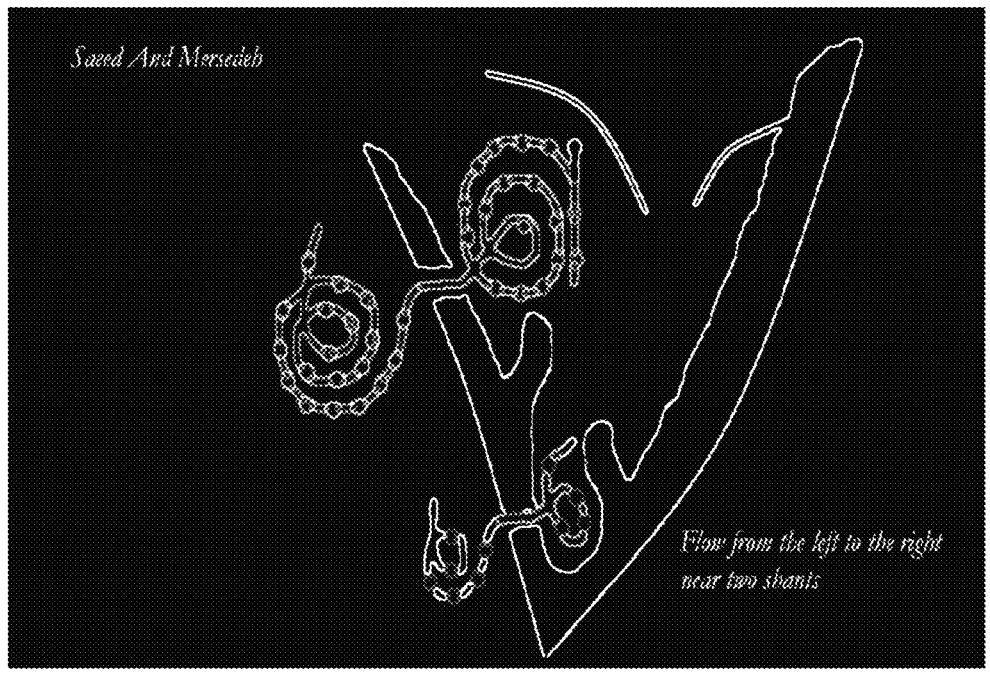

FIG.39
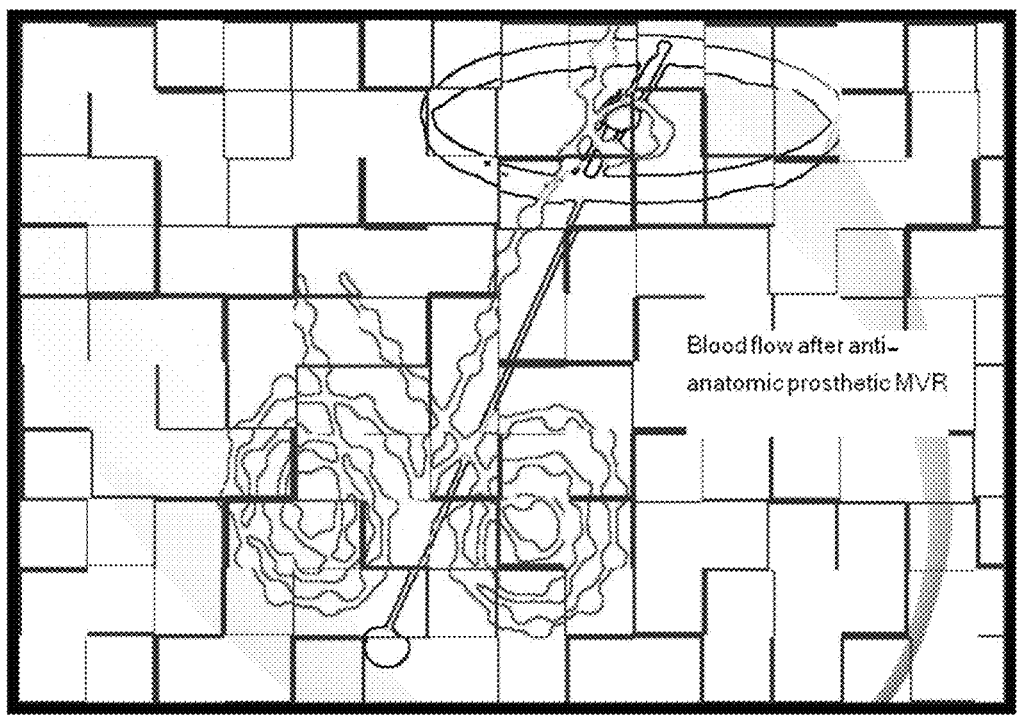
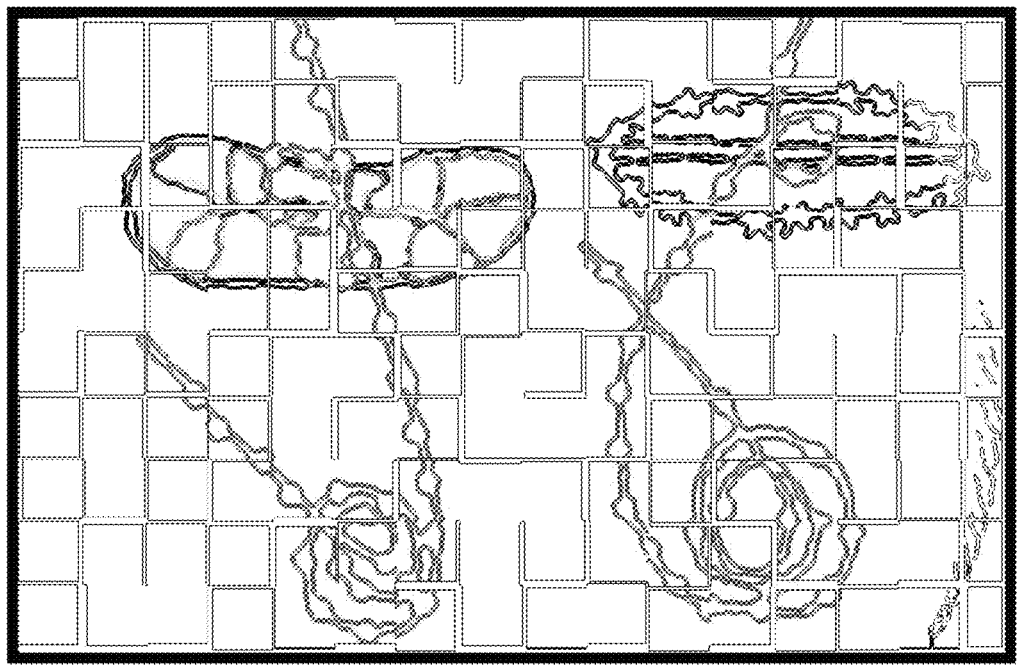

SOLUTION NAVIER-STOCKS EQUATIONS OF THE BLOOD AS A NON-NEWTONIAN FLUID IN THE LEFT VENTRICLE

CROSS-REFERENCE TO RELATED APPLICATIONS

This application claims the benefit of U.S. provisional patent application Ser. No. 61/345,615, filed May 18, 2010; 61/434,970 filed on Jan. 21, 2011; and 61/434,979 filed on Jan. 21, 2011, which are incorporated herein by reference in their entireties.

FIELD OF INVENTION

The present invention relates to a method for studying blood flow regionally near echocardiography samples and globally inside the left ventricle and software and system thereof.

BACKGROUND OF INVENTION

The Navier-Stokes equations, named after Claude-Louis Navier and George Gabriel Stokes, describe the motion of fluid substances. These equations arise from applying Newton's second law to fluid motion, together with the assumption that the fluid stress is the sum of a diffusing viscous term (proportional to the gradient of velocity), plus a pressure term.

The equations are useful because they describe the physics of many things of academic and economic interest. They may be used to model the weather, ocean currents, water flow in a pipe and air flow around a wing. The Navier-Stokes equations in their full and simplified forms help with the design of aircraft and cars, the study of blood flow, the design of power stations, the analysis of pollution, and many other things. Coupled with Maxwell's equations they can be used to model and study magneto-hydrodynamics.

Together with supplemental equations (for example, conservation of mass) and well formulated boundary conditions, the Navier-Stokes equations seem to model fluid motion accurately; even turbulent flows seem (on average) to agree with real world observations.

The Navier-Stokes equations assume that the fluid being studied is a continuum not moving at relativistic velocities. At very small scales or under extreme conditions, real fluids made out of discrete molecules will produce results different from the continuous fluids modelled by the Navier-Stokes equations. Depending on the Knudsen number of the problem, statistical mechanics or possibly even molecular dynamics may be a more appropriate approach.

Time tested formulations exist for common fluid families, but the application of the Navier-Stokes equations to less common families tends to result in very complicated formulations which are an area of current research. For this reason, these equations are usually written for Newtonian fluids. Studying such fluids is "simple" because the viscosity model ends up being linear; truly general models for the flow of other kinds of fluids, such as blood as of 2011, do not exist.

Solving the Navier-Stocks equations for an arbitrary fluid is an open problem in mathematics and of course, a very good modelling of such this fluid is strongly related to the membrane where the fluid flows on it. The blood as a complicated and Non-Newtonian fluid through the heart's chambers and heart's valves is one of the big challenges among mathematical-, medical-, physical- and computer-sciences. So far a lot of studies of the blood flowing through the heart have been attempted by various simple assumptions.

For instance, U.S. Pat. No. 5,537,641, assigned to University of Central Florida Research Foundation, Inc. discloses a method for generating a three-dimensional animation model that stimulates a fluid flow on a three-dimensional graphics display. The said patent does not extend the solution of Navier-Stokes equation to non-Newtonian fluids like blood explicitly.

U.S. Pat. No. 6,135,957 assigned to U.S. Philips Corporation describes a method of determining the viscosity and the pressure gradient in a blood vessel, including the acquisition of n≥2 blood speed values, corresponding to the same number of n radii of the blood vessel, determined along a diameter situated in a given axial position, formation of a blood speed vector by means of said n blood speed values, and evaluation of said viscosity and pressure gradient on the basis of a transformation of said blood speed value, including formation of a linear relation which directly links a flow rate vector (y) to the speed derivative vector (h), factorized by the viscosity ($\mu$), and to the pressure gradient vector ($\sigma$), and simultaneous evaluation of the two values to be determined for the viscosity ($\mu$) and the pressure gradient ($\sigma$) on the basis of said direct equation. The said method, as disclosed in U.S. '957, specifically used to determine blood speed, but seemingly does not disclose a method or system for modelling cardiac condition, specifically left ventricle having a main role in cardiac function based on flow.

Hence, the present inventors propose a novel system for solution of Navier-Stokes to model not only the normal blood flow inside the left ventricle but also for the other cavities and valves and model heart diseases.

SUMMARY OF INVENTION

The invention provides method for studying the blood flows regionally near echocardiography samples and globally inside the left ventricle.

In an aspect, according to current invention, the blood flow curves are regionally investigated near the neighbourhoods of echocardiography samples that is, the basal, mid and apical anterior, the basal, mid and apical inferior, and the basal, mid and apical lateral, the basal, mid and apical septum.

In another aspect, the flow curves investigated hereinabove are used to model heart diseases using echocardiography.

BRIEF DESCRIPTION OF DRAWINGS

FIG. 3 shows three rendering of the basal, mid and apical anterior in their corresponded regions.

FIG. 19 shows three rendering of the basal, mid and apical lateral in their corresponded regions at Mathlab software.

FIG. 34 shows a flowchart where states the blood flow curve inside the left ventricle is regionally made by gluing together blood flow curves that have been modeled near echocardiography samples.

FIG. 37 shows two blood flow curves from the left to the right one near a small shant in the Mathlab software.

FIG. 38 shows blood flow curves from the left to the right near two shants at VSD in Mathlab software.

FIG. 39 the first shows the blood flow curve after an anti-anatomic prosthetic Mitral valve replacement and the second shows the blood flow curves for the natural Mitral valve at the left and after an anatomic prosthetic Mitral valve replacement at the right respectively.

DETAILED DESCRIPTION OF INVENTION

The invention will now be described in details with reference to various preferred and optional embodiments to make the invention clear.

The present invention describes a method for solving the Navier-Stocks equations of the blood dynamic as a Non-Newtonian fluid in the left ventricle for modeling of the myocardial motion in an elastic membrane.

In an embodiment the invention provides modelling of the blood flow curves inside the left ventricle by studying the flow of the blood curves near echocardiography samples i.e. the basal, mid and apical Anterior and the basal, mid and apical Inferior and the basal, mid and apical Lateral and the basal, mid and apical Septum. These samples as the material elastic points in the myocardium of the left ventricle induce mechanical parameters to the viscosity of blood.

Invention describes method of formulating and calculating the mechanical parameters of blood, numerically, and then applying Navier-Stocks equations to model the blood flow curve regionally and globally inside the left ventricle. The method is summarized as below a. Calculating mechanical parameters of blood near echocardiography samples;

b. calculating the myofiber curve for echocardiography samples of step (a);

c. studying "quadratic form" for the curve of step (b) for each echocardiography samples;

d. determining the blood flow curve for step (c) for each echocardiography samples and e. integrating the blood flow curves of step (d) for determining blood flow curve for left ventricle globally.

Figure 1:
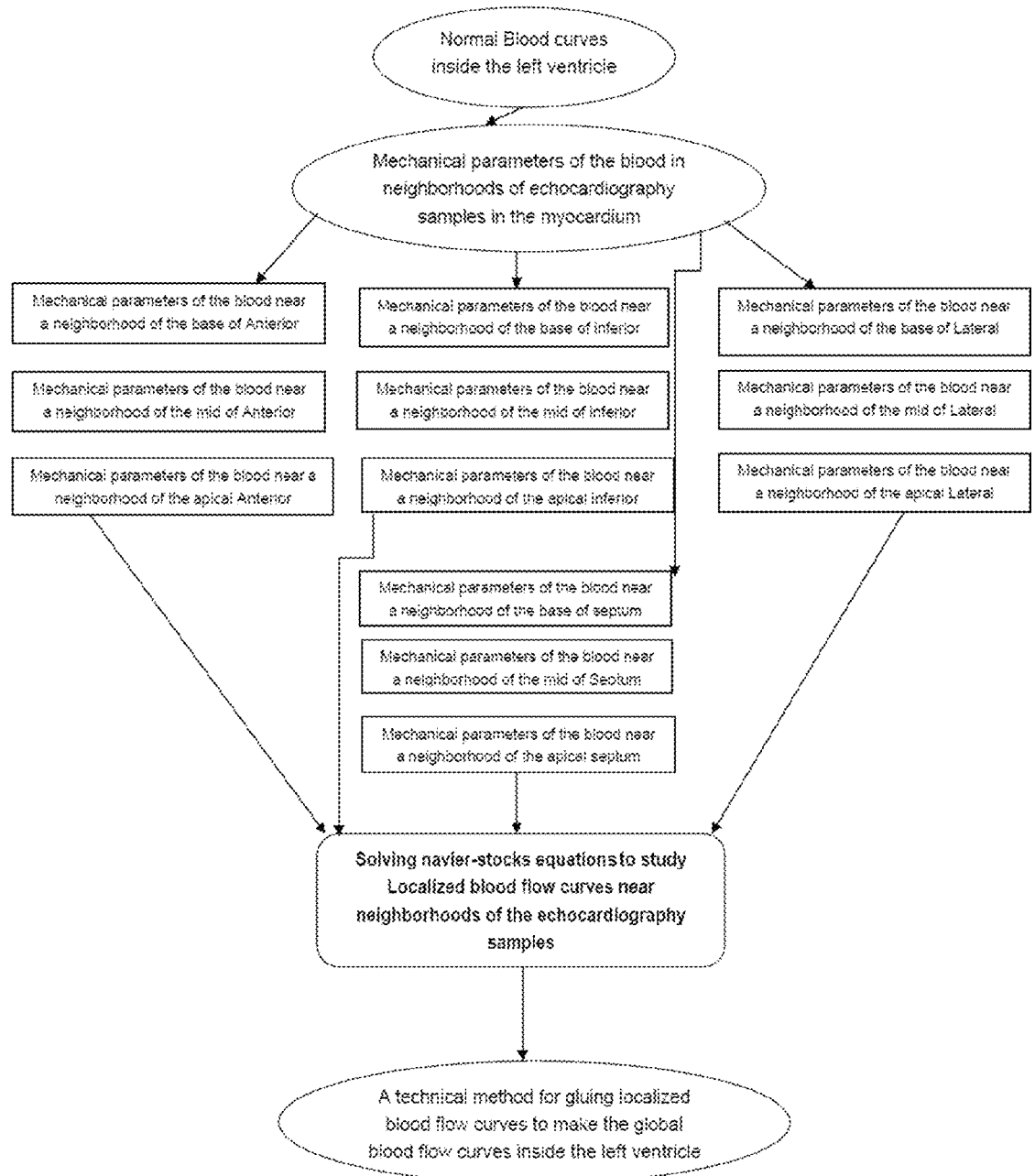
FIG. 1 shows a general flowchart of this invention.
Figure 2:
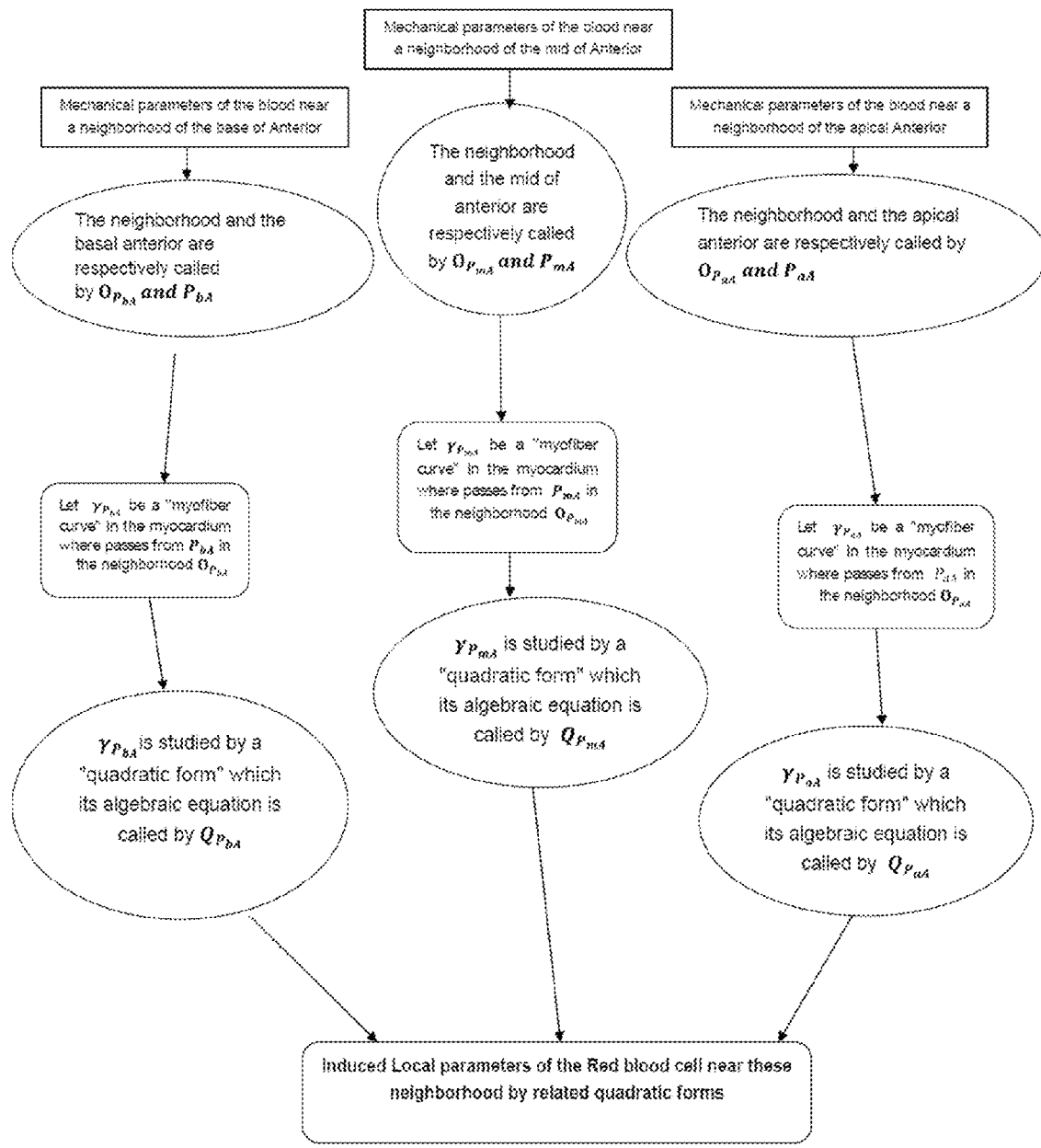
FIG. 2 shows a flowchart where states the basal, mid and apical Anterior as three echocardiography samples in the left ventricle, in their corresponded regions.

In an embodiment of invention, FIG. 2 illustrates a flowchart giving mathematical signs of the basal Anterior and the mid of Anterior and the apical Anterior in their corresponded regions to obtain good formulizations of the induced mechanical parameters of the blood.

Referring to FIG. 3, invention further describes geometrical modeling of the basal, mid and apical Anterior using Mathlab software as described below.

let $\epsilon_{rr,P_{bA}}$, $\epsilon_{ll,P_{bA}}$ and $\epsilon_{cc,P_{bA}}$ be strain components of the basal Anterior, $P_{bA}$ we set $$\gamma_{P_{bA}} = \{\text{each myocardial sample } X \text{ that } \epsilon_{rr,X} \times \epsilon_{ll,X} = \epsilon_{rr,P_{bA}} \times \epsilon_{ll,P_{bA}} \text{ and } \epsilon_{rr,X} \times \epsilon_{ll,X} \times \epsilon_{cc,X} = \epsilon_{rr,P_{bA}} \times \epsilon_{ll,P_{bA}} \times \epsilon_{cc,P_{bA}}\}$$

and similarly for the mid of Anterior and the apical Anterior would have the following sets;

$$\gamma_{P_{mA}} = \{\text{each myocardial sample } X \text{ that } \epsilon_{rr,X} \times \epsilon_{ll,X} = \epsilon_{rr,P_{mA}} \times \epsilon_{ll,P_{mA}} \text{ and } \epsilon_{rr,X} \times \epsilon_{ll,X} \times \epsilon_{cc,X} = \epsilon_{rr,P_{mA}} \times \epsilon_{ll,P_{mA}} \times \epsilon_{cc,P_{mA}}\}$$

$$\gamma_{P_{aA}} = \{\text{each myocardial sample } X \text{ that } \epsilon_{rr,X} \times \epsilon_{ll,X} = \epsilon_{rr,P_{aA}} \times \epsilon_{ll,P_{aA}} \text{ and } \epsilon_{rr,X} \times \epsilon_{ll,X} \times \epsilon_{cc,X} = \epsilon_{rr,P_{aA}} \times \epsilon_{ll,P_{aA}} \times \epsilon_{cc,P_{aA}}\}$$

In fact, $\gamma_{P_{bA}}$, $\gamma_{P_{mA}}$ and $\gamma_{P_{aA}}$ are those myofiber bands in the myocardium where have been called at FIG. 2.

In a preferred embodiment Q's at FIG. 3 have the following algebraic equations:

$$Q_{P_{bA}} : D_{P_{bA}} = \left(\sum_{k,l} \epsilon'_{rr_{P_k},P_l} dt\right) \cdot y_1^2 + \left(\sum_{k,l} \epsilon'_{ll_{P_k},P_l} dt\right) \cdot y_2^2 + \left(\sum_{k,l} \epsilon'_{cc_{P_k},P_l} dt\right) \cdot y_3^2$$

$$D_{P_{bA}} = \left(\sum_{k,l} \epsilon'_{rr_{P_k},P_l} dt\right) \cdot y_{1,bA}^2 + \left(\sum_{k,l} \epsilon'_{ll_{P_k},P_l} dt\right) \cdot y_{2,bA}^2 + \left(\sum_{k,l} \epsilon'_{cc_{P_k},P_l} dt\right) \cdot y_{3,bA}^2$$

Where, $P_k$ and $P_l$ are points belonging to $\gamma_{P_{bA}} \cap O_{P_{bA}}$ and if $P_{bA} = (y_{1,bA}, y_{2,bA}, y_{3,bA})$ as Cartesian coordinate.

By a similar argument we have the algebraic equations in Cartesian coordinate of Q's for the mid of Anterior and the apical Anterior:

For the mid of Anterior:

$$Q_{P_{mA}} : D_{P_{mA}} = \left(\sum_{k,l} \epsilon'_{rr_{P_k},P_l} dt\right) \cdot y_1^2 + \left(\sum_{k,l} \epsilon'_{ll_{P_k},P_l} dt\right) \cdot y_2^2 + \left(\sum_{k,l} \epsilon'_{cc_{P_k},P_l} dt\right) \cdot y_3^2$$

$$D_{P_{mA}} = \left(\sum_{k,l} \epsilon'_{rr_{P_k},P_l} dt\right) \cdot y_{1,mA}^2 + \left(\sum_{k,l} \epsilon'_{ll_{P_k},P_l} dt\right) \cdot y_{2,mA}^2 + \left(\sum_{k,l} \epsilon'_{cc_{P_k},P_l} dt\right) \cdot y_{3,mA}^2$$

Where, $P_k$ and $P_l$ are points belonging to $\gamma_{P_{mA}} \cap O_{P_{mA}}$ and if $P_{mA} = (y_{1,mA}, y_{2,mA}, y_{3,mA})$ as Cartesian coordinate.

For apical Anterior:

$$Q_{P_{aA}} : D_{P_{aA}} = \left(\sum_{k,l} \epsilon'_{rr_{P_k},P_l} dt\right) \cdot y_1^2 + \left(\sum_{k,l} \epsilon'_{ll_{P_k},P_l} dt\right) \cdot y_2^2 + \left(\sum_{k,l} \epsilon'_{cc_{P_k},P_l} dt\right) \cdot y_3^2$$

$$D_{P_{aA}} = \left(\sum_{k,l} \epsilon'_{rr_{P_k},P_l} dt\right) \cdot y_{1,aA}^2 + \left(\sum_{k,l} \epsilon'_{ll_{P_k},P_l} dt\right) \cdot y_{2,aA}^2 + \left(\sum_{k,l} \epsilon'_{cc_{P_k},P_l} dt\right) \cdot y_{3,aA}^2$$

Where, $P_k$ and $P_l$ are points belonging to $\gamma_{P_{aA}} \cap O_{P_{aA}}$ and if $P_{aA} = (y_{1,aA}, y_{2,aA}, y_{3,aA})$ as Cartesian coordinate.

Figure 5:
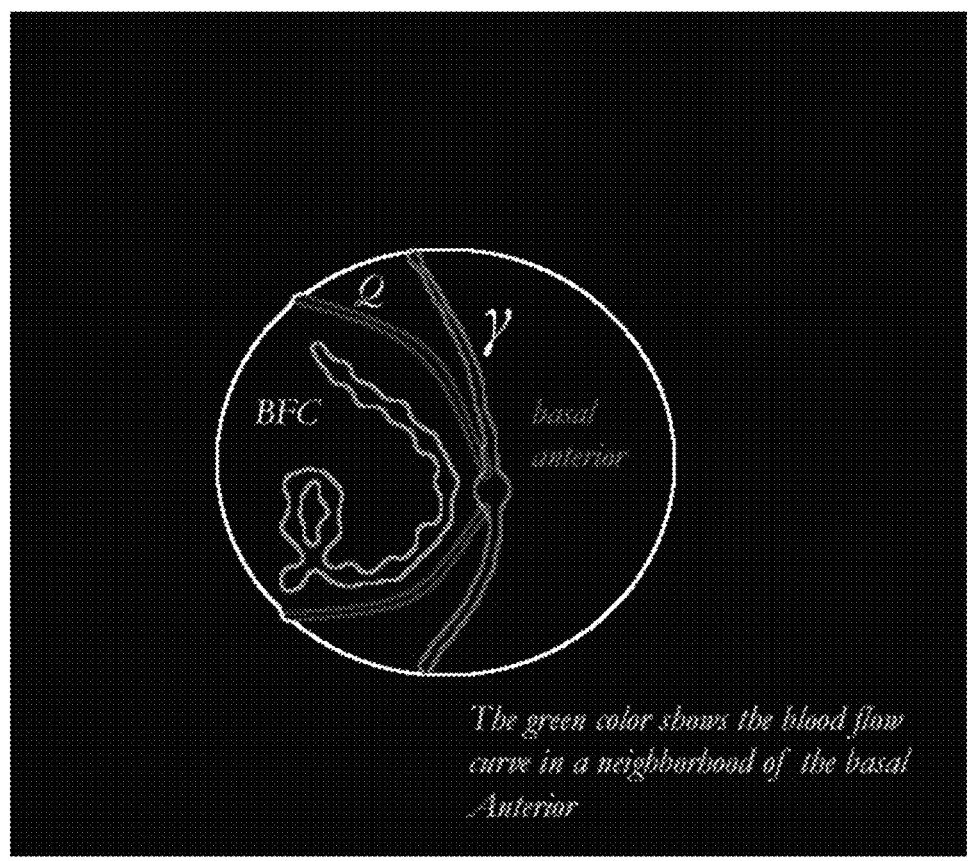
FIG. 5 shows the blood flow curve near the corresponded neighbourhood of the basal anterior in the myocardium of the left ventricle where has been rendered at Mathlab software.

In a preferred embodiment, the invention provides an analytical solution of the Navier-Stocks equations in the region $O_{P_{mA}}$ of the apical Inferior. FIG. 5 shows a rendering of these solutions in the mathlab software.

Figure 4:
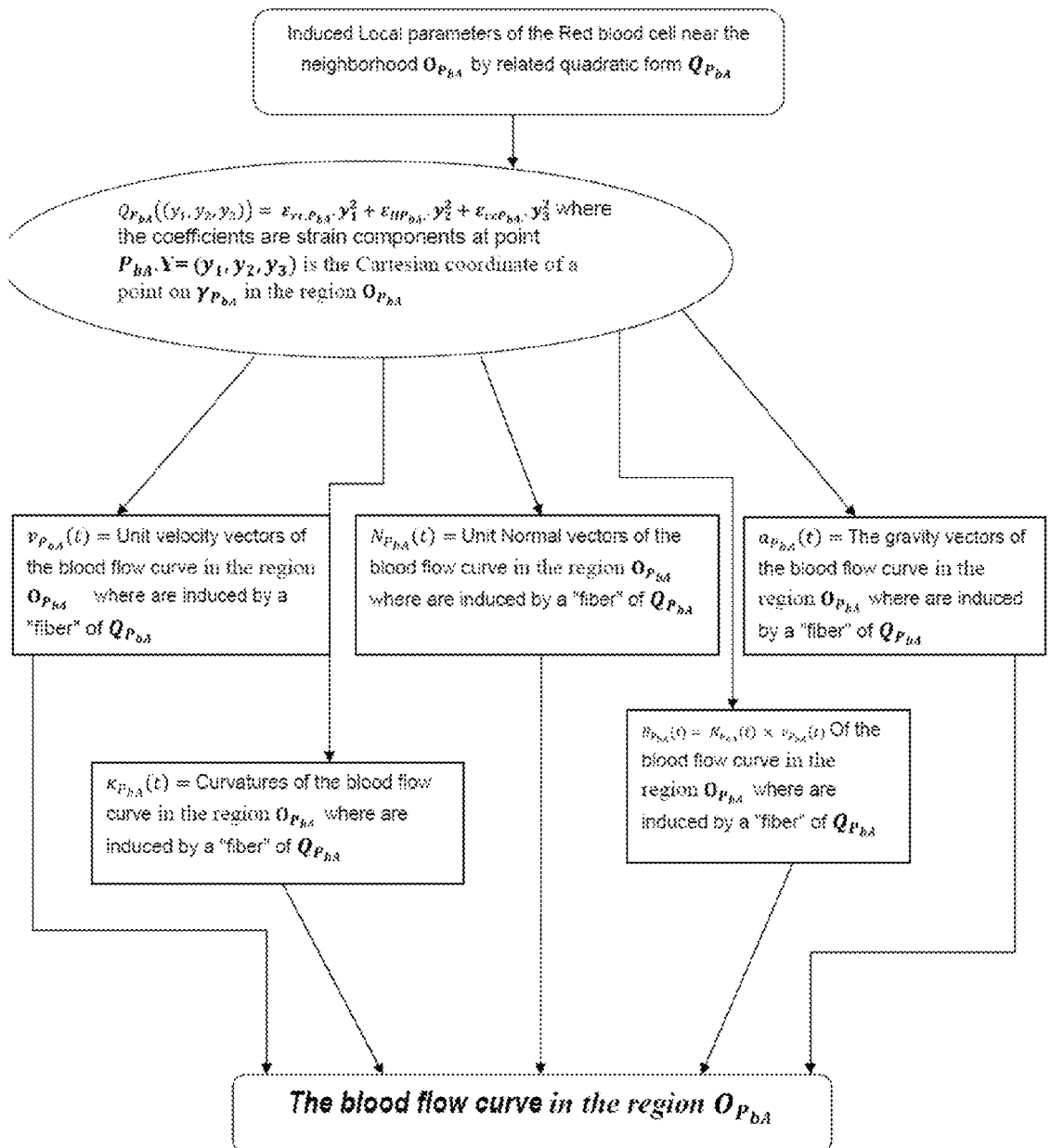
FIG. 4 shows a flowchart that models the blood flow curve near a neighbourhood of the basal Anterior in the myocardium of the left ventricle.

FIG. 4 shows the mechanical parameters of blood which were induced by $Q_{P_{mA}}$ in region $O_{P_{mA}}$ related to apical inferior. The surface is;

$$F_{P_{bA}}((y_1, y_2, y_3)) = \left(\sum_{k,l} \epsilon'_{rr_{P_k},P_l} dt\right) \cdot y_1^2 + \left(\sum_{k,l} \epsilon'_{ll_{P_k},P_l} dt\right) \cdot y_2^2 + \left(\sum_{k,l} \epsilon'_{cc_{P_k},P_l} dt\right) \cdot y_3^2 - D_{P_{bA}}$$

In the region $O_{P_{bA}}$, let $\phi_{1,P_{bA}}(t)$, $\phi_{2,P_{bA}}(t)$ and $\phi_{3,P_{bA}}(t)$ are parameterized forms of the projections of the surface $F_{P_{bA}}$ on xy-axis and yz-axis:

$$\varphi_{1,P_{bA}}(t) = \left(t, \left(\left(D_{P_{bA}} - \left(\sum_{k,l} \epsilon'_{rr_{P_k},P_l} dt\right) t^2\right) \Big/ \left(\sum_{k,l} \epsilon'_{ll_{P_k},P_l} dt\right)\right)^{\frac{1}{2}}\right);$$

$$\varphi_{2,P_{bA}}(t) = \left(t, \left(\left(D_{P_{bA}} - \left(\sum_{k,l} \epsilon'_{rr_{P_k},P_l} dt\right) t^2\right) \Big/ \left(\sum_{k,l} \epsilon'_{cc_{P_k},P_l} dt\right)\right)^{\frac{1}{2}}\right);$$

$$\varphi_{3,P_{bA}}(t) = \left(t, \left(\left(D_{P_{bA}} - \left(\sum_{k,l} \epsilon'_{ll_{P_k},P_l} dt\right) t^2\right) \Big/ \left(\sum_{k,l} \epsilon'_{cc_{P_k},P_l} dt\right)\right)^{\frac{1}{2}}\right)$$

Following formulae were set;

$$T_{1,P_{bA}}(t) = \phi_{1,P_{bA}}(t)' / |\phi_{1,P_{bA}}(t)'|;$$

$$S_{1,P_{bA}} = \int_{t_o}^{t} \varphi_{1,P_{bA}}(u)' du;$$

$$\kappa_{1,P_{bA}}(t) \cdot N_{1,P_{bA}}(t) = \frac{dT_{1,P_{bA}}}{ds};$$

$$\kappa_{1,P_{bA}}(t) = \left(\left(\left(D_{P_{bA}} - \left(\sum_{k,l} \epsilon'_{rr_{P_k},P_l} dt\right) t^2\right) \Big/ \left(\sum_{k,l} \epsilon'_{ll_{P_k},P_l} dt\right)\right)^{\frac{1}{2}}\right) - 0 \Big/ S_{1,P_{bA}}^3;$$

$$a_{1,P_{bA}}(t) = S_{1,P_{bA}}'' \cdot T_{1,P_{bA}}(t) + \kappa_{1,P_{bA}}(t) \cdot N_{1,P_{bA}}(t)$$

$$T_{2,P_{bA}}(t) = \phi_{2,P_{bA}}(t)' / |\phi_{2,P_{bA}}(t)'|;$$

$$S_{2,P_{bA}} = \int_{t_o}^{t} \varphi_{2,P_{bA}}(u)' du;$$

$$\kappa_{2,P_{bA}}(t) \cdot N_{2,P_{bA}}(t) = \frac{dT_{2,P_{bA}}}{ds};$$

$$\kappa_{2,P_{bA}}(t) = \left(\left(\left(D_{P_{bA}} - \left(\sum_{k,l} \epsilon'_{rr_{P_k},P_l} dt\right) t^2\right) \Big/ \left(\sum_{k,l} \epsilon'_{cc_{P_k},P_l} dt\right)\right)^{\frac{1}{2}}\right) - 0 \Big/ S_{2,P_{bA}}^3;$$

$$a_{2,P_{bA}}(t) = S_{2,P_{bA}}'' \cdot T_{2,P_{bA}}(t) + \kappa_{2,P_{bA}}(t) \cdot N_{2,P_{bA}}(t)$$

$$T_{3,P_{bA}}(t) = \phi_{3,P_{bA}}(t)' / |\phi_{3,P_{bA}}(t)'|;$$

$$S_{3,P_{bA}} = \int_{t_o}^{t} \varphi_{3,P_{bA}}(u)' du;$$

$$\kappa_{3,P_{bA}}(t) \cdot N_{3,P_{bA}}(t) = \frac{dT_{2,P_{bA}}}{ds};$$

$$\kappa_{3,P_{bA}}(t) = \left(\left(\left(D_{P_{bA}} - \left(\sum_{k,l} \varepsilon'_{u_{P_k},P_l} dI\right)t^2\right)\middle/\left(\sum_{k,l} \varepsilon'_{u_{P_k},P_l} dI\right)\right)^{\frac{1}{2}}\right) - 0 \middle/ S_{3,P_{bA}}^3;$$

$$a_{3,P_{bA}}(t) = S_{3,P_{bA}} \cdot T_{3,P_{bA}}(t) + \kappa_{3,P_{bA}}(t) \cdot N_{3,P_{bA}}(t)$$

If $(x_1, x_2, x_3, t)$ is the coordinate system of the red blood cell in a neighbourhood $O_{P_{bA}}$ of the basal anterior and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{bA}}, C_{2,P_{bA}}$ and $C_{3,P_{bA}}$ are the graphs of $\phi_{1,P_{bA}}(t), \phi_{2,P_{bA}}(t)$ and $\phi_{3,P_{bA}}(t)$ respectively then the mechanical parameters of the red blood cells in the region $O_{P_{bA}}$ are realized by the following formulas:

$$v_{1,P_{bA}}(t) = \int_{C_{1,P_{bA}}} T_{1,P_{bA}}(t) \otimes \delta(x_1, x_2, x_3, t) d\tau;$$

$$n_{1,P_{bA}}(t) = \int_{C_{1,P_{bA}}} N_{1,P_{bA}}(t) \otimes \delta(x_1, x_2, x_3, t) d\tau;$$

$$a_{1,P_{bA}}^{RBC}(t) = \int_{C_{1,P_{bA}}} a_{1,P_{bA}}(t) \otimes \delta(x_1, x_2, x_3, t) dt$$

$$v_{2,P_{bA}}(t) = \int_{C_{2,P_{bA}}} T_{2,P_{bA}}(t) \otimes \delta(x_1, x_2, x_3, t) d\tau;$$

$$n_{2,P_{bA}}(t) = \int_{C_{2,P_{bA}}} N_{2,P_{bA}}(t) \otimes \delta(x_1, x_2, x_3, t) d\tau;$$

$$a_{2,P_{bA}}^{RBC}(t) = \int_{C_{2,P_{bA}}} a_{2,P_{bA}}(t) \otimes \delta(x_1, x_2, x_3, t) dt$$

$$v_{3,P_{bA}}(t) = \int_{C_{3,P_{bA}}} T_{3,P_{bA}}(t) \otimes \delta(x_1, x_2, x_3, t) d\tau;$$

$$n_{3,P_{bA}}(t) = \int_{C_{3,P_{bA}}} N_{3,P_{bA}}(t) \otimes \delta(x_1, x_2, x_3, t) d\tau;$$

$$a_{3,P_{bA}}^{RBC}(t) = \int_{C_{3,P_{bA}}} a_{3,P_{bA}}(t) \otimes \delta(x_1, x_2, x_3, t) dt$$

the formulas as mentioned hereinabove give analytical solution of the Navier-Stocks equations in the region $O_{P_{bA}}$ of the basal Anterior. The invention provides, with reference to FIG. 5, provides a rendering of this solution in the mathlab software.

Figure 7:
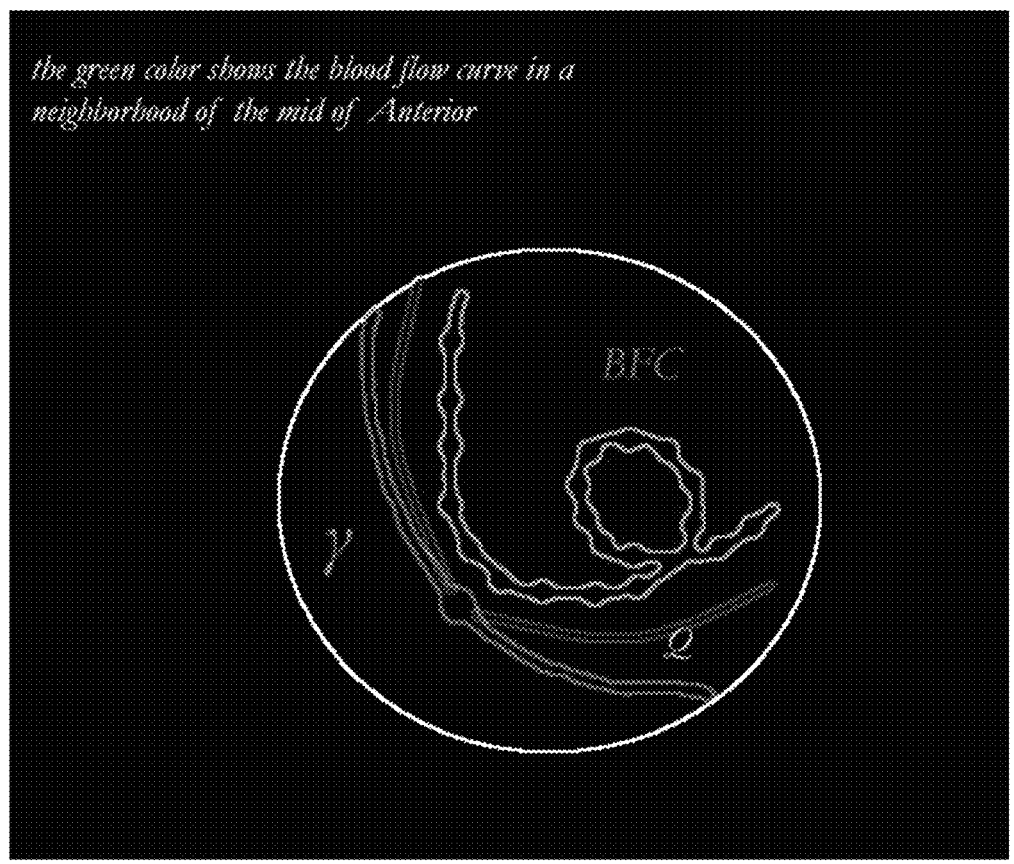
FIG. 7 shows the blood flow curve near the corresponded neighborhood of the mid anterior in the myocardium of the left ventricle where has been rendered at Mathlab software.

In a preferred embodiment, the invention provides an analytical solution of the Navier-Stocks equations in the region $O_{P_{mA}}$ of the apical Inferior. FIG. 7 shows a rendering of these solutions in the mathlab software.

Figure 6:
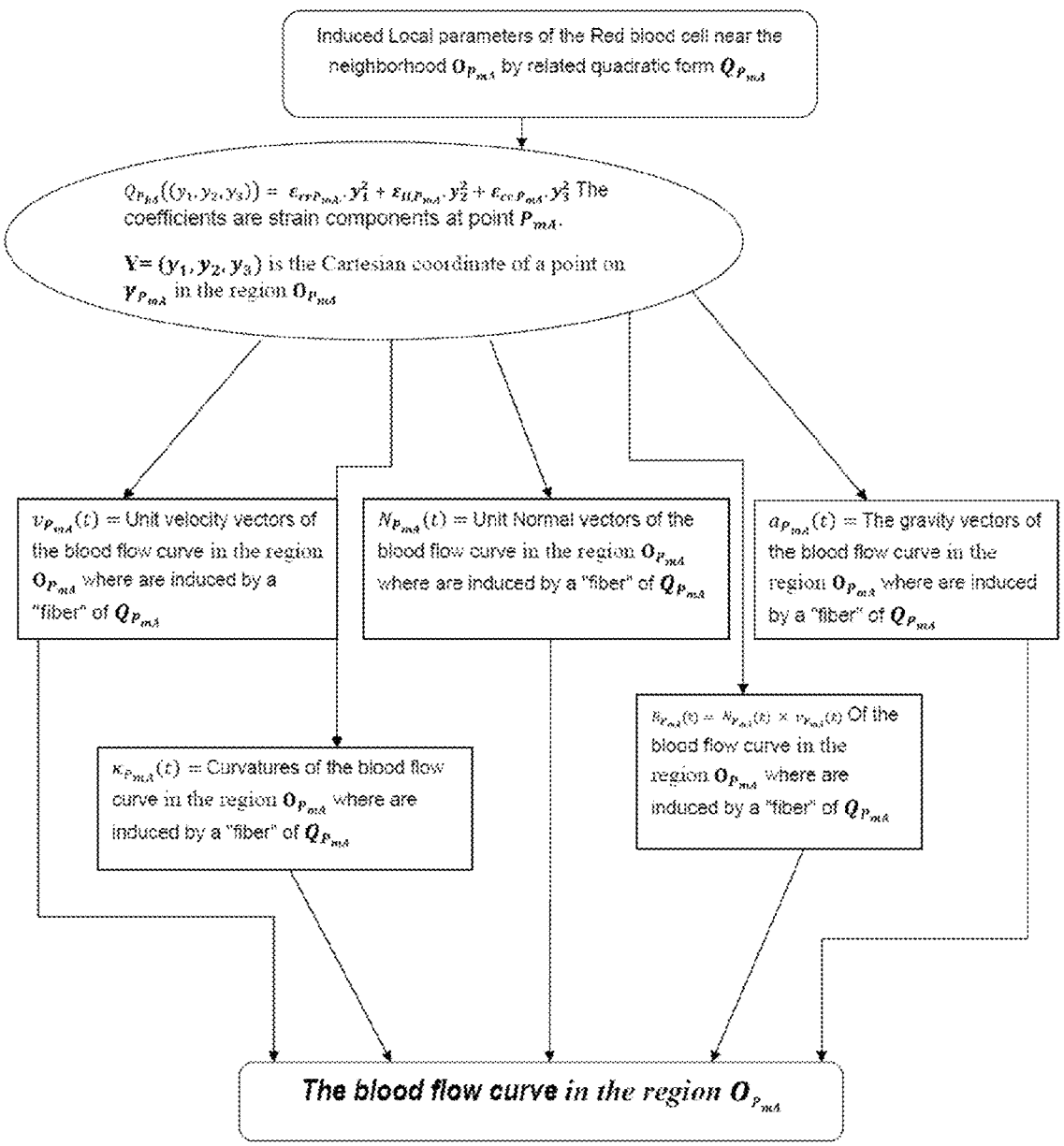
FIG. 6 shows a flowchart that models the blood flow curve near a neighbourhood of the mid Anterior in the myocardium of the left ventricle.

FIG. 6 shows the mechanical parameters of blood which were induced by $Q_{P_{mA}}$ in region $O_{P_{mA}}$ related to apical inferior. The surface is;

$$F_{P_{mA}}((y_1, y_2, y_3)) = \left(\sum_{k,l} \varepsilon'_{rr_{P_k},P_l} dI\right) \cdot y_1^2 + \left(\sum_{k,l} \varepsilon'_{u_{P_k},P_l} dI\right) \cdot y_2^2 + \left(\sum_{k,l} \varepsilon'_{cc_{P_k},P_l} dI\right) \cdot y_3^2 - D_{P_{mA}}.$$

In the region $O_{P_{mA}}$, let $\phi_{1,P_{mA}}(t), \phi_{2,P_{mA}}(t)$ and $\phi_{3,P_{mA}}(t)$ are parameterized forms of the projections of the surface $F_{P_{mA}}$ on xy-axis and yz-axis:

$$\varphi_{1,P_{mA}}(t) = \left(t, \left(\left(D_{P_{mA}} - \left(\sum_{k,l} \varepsilon'_{rr_{P_k},P_l} dI\right)t^2\right)\middle/\left(\sum_{k,l} \varepsilon'_{u_{P_k},P_l} dI\right)\right)^{\frac{1}{2}}\right);$$

$$\varphi_{2,P_{mA}}(t) = \left(t, \left(\left(D_{P_{mA}} - \left(\sum_{k,l} \varepsilon'_{rr_{P_k},P_l} dI\right)t^2\right)\middle/\left(\sum_{k,l} \varepsilon'_{cc_{P_k},P_l} dI\right)\right)^{\frac{1}{2}}\right);$$

$$\varphi_{3,P_{mA}}(t) = \left(t, \left(\left(D_{P_{mA}} - \left(\sum_{k,l} \varepsilon'_{u_{P_k},P_l} dI\right)t^2\right)\middle/\left(\sum_{k,l} \varepsilon'_{cc_{P_k},P_l} dI\right)\right)^{\frac{1}{2}}\right)$$

Following formulae were set;

$$T_{1,P_{mA}}(t) = \phi_{1,P_{mA}}(t)' / |\phi_{1,P_{mA}}(t)'|;$$

$$S_{1,P_{mA}} = \int_{t_o}^{t} \varphi_{1,P_{mA}}(u)' du;$$

$$\kappa_{1,P_{mA}}(t) \cdot N_{1,P_{mA}}(t) = \frac{dT_{1,P_{mA}}}{ds};$$

$$\kappa_{1,P_{mA}}(t) = \left(\left(\left(D_{P_{mA}} - \left(\sum_{k,l} \varepsilon'_{rr_{P_k},P_l} dI\right)t^2\right)\middle/\left(\sum_{k,l} \varepsilon'_{u_{P_k},P_l} dI\right)\right)^{\frac{1}{2}}\right) - 0 \middle/ S_{1,P_{mA}}^3;$$

$$a_{1,P_{mA}}(t) = S_{1,P_{mA}}'' \cdot T_{1,P_{mA}}(t) + \kappa_{1,P_{mA}}(t) \cdot N_{1,P_{mA}}(t)$$

$$T_{2,P_{mA}}(t) = \phi_{2,P_{mA}}(t)' / |\phi_{2,P_{mA}}(t)'|;$$

$$S_{2,P_{mA}} = \int_{t_o}^{t} \varphi_{2,P_{mA}}(u)' du;$$

$$\kappa_{2,P_{mA}}(t) \cdot N_{2,P_{mA}}(t) = \frac{dT_{2,P_{mA}}}{ds};$$

$$\kappa_{2,P_{mA}}(t) = \left(\left(\left(D_{P_{mA}} - \left(\sum_{k,l} \varepsilon'_{rr_{P_k},P_l} dI\right)t^2\right)\middle/\left(\sum_{k,l} \varepsilon'_{cc_{P_k},P_l} dI\right)\right)^{\frac{1}{2}}\right) - 0 \middle/ S_{2,P_{mA}}^3;$$

$$a_{2,P_{mA}}(t) = S_{2,P_{mA}}'' \cdot T_{2,P_{mA}}(t) + \kappa_{2,P_{mA}}(t) \cdot N_{2,P_{mA}}(t)$$

$$T_{3,P_{mA}}(t) = \phi_{3,P_{mA}}(t)' / |\phi_{3,P_{mA}}(t)'|;$$

$$S_{3,P_{mA}} = \int_{t_o}^{t} \varphi_{3,P_{mA}}(u)' du;$$

$$\kappa_{3,P_{mA}}(t) \cdot N_{3,P_{mA}}(t) = \frac{dT_{2,P_{mA}}}{ds};$$

$$\kappa_{3,P_{mA}}(t) = \left(\left(\left(D_{P_{mA}} - \left(\sum_{k,l} \varepsilon'_{u_{P_k},P_l} dI\right)t^2\right)\middle/\left(\sum_{k,l} \varepsilon'_{u_{P_k},P_l} dI\right)\right)^{\frac{1}{2}}\right) - 0 \middle/ S_{3,P_{mA}}^3;$$

$$a_{3,P_{mA}}(t) = S_{3,P_{mA}} \cdot T_{3,P_{mA}}(t) + \kappa_{3,P_{mA}}(t) \cdot N_{3,P_{mA}}(t)$$

If $(x_1, x_2, x_3, t)$ is the coordinate system of the red blood cell in a neighbourhood $O_{P_{mA}}$ of the basal anterior and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{mA}}$, $C_{2,P_{mA}}$ and $C_{3,P_{mA}}$ are the graphs of $\phi_{1,P_{mA}}(t)$, $\phi_{2,P_{mA}}(t)$ and $\phi_{3,P_{mA}}(t)$ respectively then the mechanical parameters of the red blood cells in the region $O_{P_{mA}}$ are realized by the following formulas:

$$v_{1,P_{mA}}(t) = \int_{C_{1,P_{mA}}} T_{1,P_{mA}}(t) \otimes \delta(x_1, x_2, x_3, t) d\tau;$$

$$n_{1,P_{mA}}(t) = \int_{C_{1,P_{mA}}} N_{1,P_{mA}}(t) \otimes \delta(x_1, x_2, x_3, t) d\tau;$$

$$a^{RBC}_{1,P_{mA}}(t) = \int_{C_{1,P_{mA}}} a_{1,P_{mA}}(t) \otimes \delta(x_1, x_2, x_3, t) dt$$

$$v_{2,P_{mA}}(t) = \int_{C_{2,P_{mA}}} T_{2,P_{mA}}(t) \otimes \delta(x_1, x_2, x_3, t) d\tau;$$

$$n_{2,P_{mA}}(t) = \int_{C_{2,P_{mA}}} N_{2,P_{mA}}(t) \otimes \delta(x_1, x_2, x_3, t) d\tau;$$

$$a^{RBC}_{2,P_{mA}}(t) = \int_{C_{2,P_{mA}}} a_{2,P_{mA}}(t) \otimes \delta(x_1, x_2, x_3, t) dt$$

$$v_{3,P_{mA}}(t) = \int_{C_{3,P_{mA}}} T_{3,P_{mA}}(t) \otimes \delta(x_1, x_2, x_3, t) d\tau;$$

$$n_{3,P_{mA}}(t) = \int_{C_{3,P_{mA}}} N_{3,P_{mA}}(t) \otimes \delta(x_1, x_2, x_3, t) d\tau;$$

$$a^{RBC}_{3,P_{mA}}(t) = \int_{C_{3,P_{mA}}} a_{3,P_{mA}}(t) \otimes \delta(x_1, x_2, x_3, t) dt$$

Figure 9:
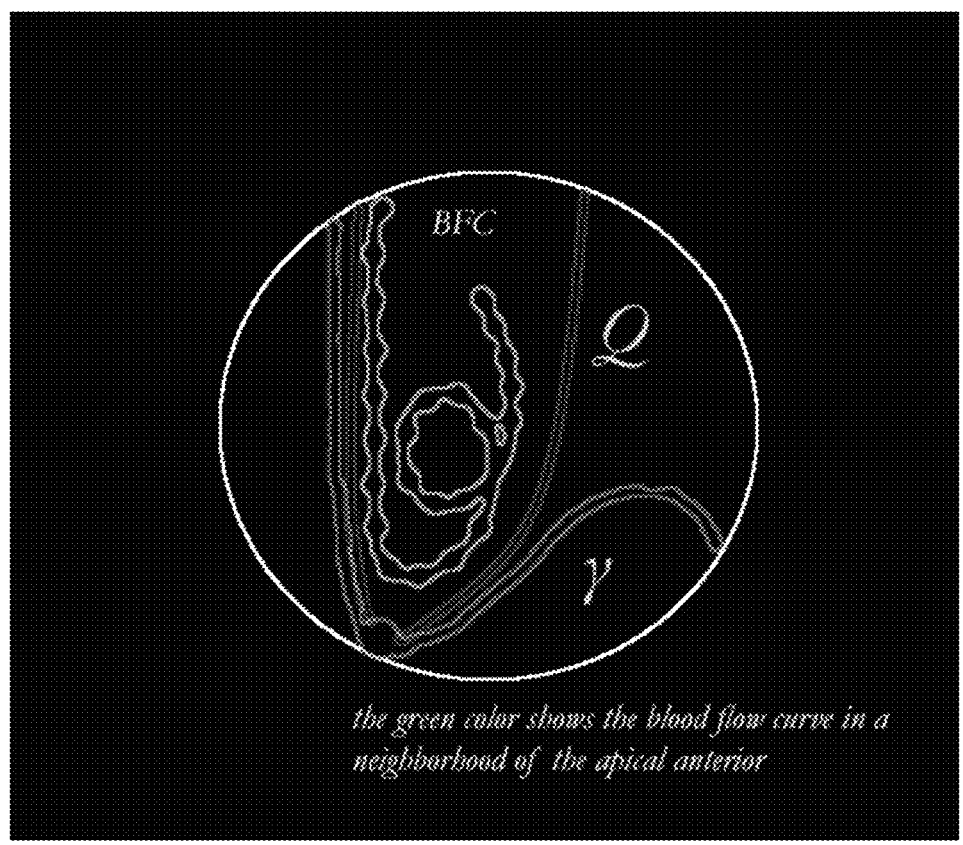
FIG. 9 shows the blood flow curve near the corresponded neighborhood of the mid anterior in the myocardium of the left ventricle where has been rendered at Mathlab software.

In a preferred embodiment, the invention provides an analytical solution of the Navier-Stocks equations in the region $O_{P_{aA}}$ of the apical Inferior. FIG. 9 shows a rendering of these solutions in the mathlab software.

Figure 8:
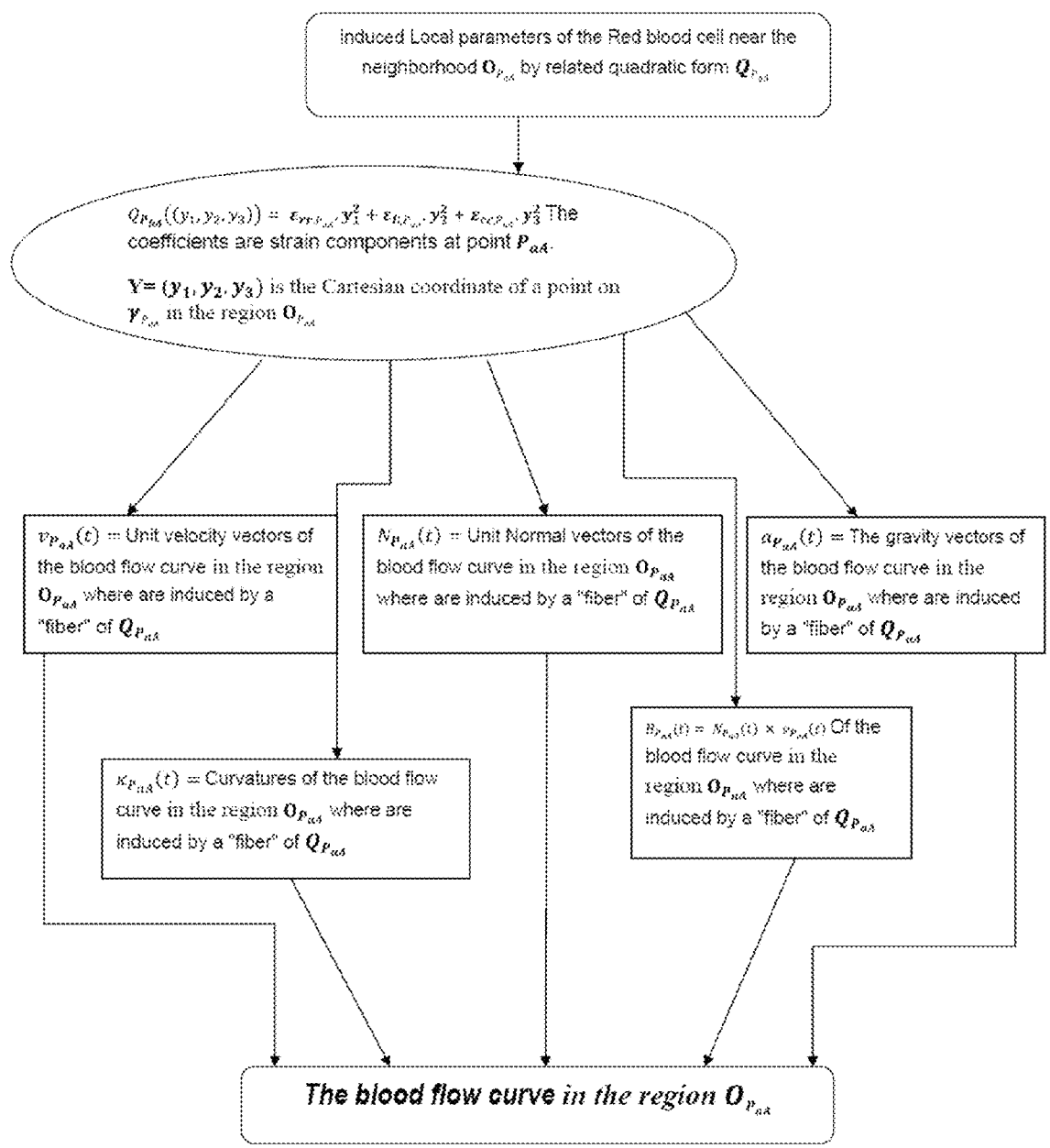
FIG. 8 shows a flowchart that models the blood flow curve near a neighborhood of the apical Anterior in the myocardium of the left ventricle.

FIG. 8 shows the mechanical parameters of blood which were induced by $Q_{P_{aA}}$ in region $O_{P_{aA}}$ related to apical inferior. The surface is;

$$F_{P_{aA}}((y_1, y_2, y_3)) = \left(\sum_{k,l} \varepsilon'_{rr_{P_k,P_l}} d\tau\right) \cdot y_1^2 + \left(\sum_{k,l} \varepsilon'_{u_{P_k,P_l}} d\tau\right) \cdot y_2^2 + \left(\sum_{k,l} \varepsilon'_{cc_{P_k,P_l}} d\tau\right) \cdot y_3^2 - D_{P_{aA}}$$

In the region $O_{P_{aA}}$, let $\phi_{1,P_{aA}}(t)$, $\phi_{2,P_{aA}}(t)$ and $\phi_{3,P_{aA}}(t)$ are parameterized forms of the projections of the surface $F_{P_{aA}}$ on xy-axis and yz-axis:

$$\varphi_{1,P_{aA}}(t) = \left(t, \left(\left(D_{P_{aA}} - \left(\sum_{k,l} \varepsilon'_{rr_{P_k,P_l}} d\tau\right) t^2\right) \bigg/ \left(\sum_{k,l} \varepsilon'_{u_{P_k,P_l}} d\tau\right)\right)^{\frac{1}{2}}\right);$$

$$\varphi_{2,P_{aA}}(t) = \left(t, \left(\left(D_{P_{aA}} - \left(\sum_{k,l} \varepsilon'_{rr_{P_k,P_l}} d\tau\right) t^2\right) \bigg/ \left(\sum_{k,l} \varepsilon'_{cc_{P_k,P_l}} d\tau\right)\right)^{\frac{1}{2}}\right);$$

$$\varphi_{3,P_{aA}}(t) = \left(t, \left(\left(D_{P_{aA}} - \left(\sum_{k,l} \varepsilon'_{u_{P_k,P_l}} d\tau\right) t^2\right) \bigg/ \left(\sum_{k,l} \varepsilon'_{cc_{P_k,P_l}} d\tau\right)\right)^{\frac{1}{2}}\right)$$

Following formulae were set;

$$T_{1,P_{aA}}(t) = \phi_{1,P_{aA}}(t)' / |\phi_{1,P_{aA}}(t)'|;$$

$$S_{1,P_{aA}} = \int_{t_o}^{t} \varphi_{1,P_{aA}}(u)' du;$$

$$\kappa_{1,P_{aA}}(t) \cdot N_{1,P_{aA}}(t) = \frac{dT_{1,P_{aA}}}{ds};$$

$$\kappa_{1,P_{aA}}(t) = \left(\left(\left(D_{P_{aA}} - \left(\sum_{k,l} \varepsilon'_{rr_{P_k,P_l}} d\tau\right) t^2\right) \bigg/ \left(\sum_{k,l} \varepsilon'_{u_{P_k,P_l}} d\tau\right)\right)^{\frac{1}{2}}\right) - 0 \bigg/ S^{'3}_{1,P_{aA}};$$

$$a_{1,P_{aA}}(t) = S_{1,P_{aA}}'' \cdot T_{1,P_{aA}}(t) + \kappa_{1,P_{aA}}(t) \cdot N_{1,P_{aA}}(t)$$

$$T_{2,P_{aA}}(t) = \phi_{2,P_{aA}}(t)' / |\phi_{2,P_{aA}}(t)'|;$$

$$S_{2,P_{aA}} = \int_{t_o}^{t} \varphi_{2,P_{aA}}(u)' du;$$

$$\kappa_{2,P_{aA}}(t) \cdot N_{2,P_{aA}}(t) = \frac{dT_{2,P_{aA}}}{ds};$$

$$\kappa_{2,P_{aA}}(t) = \left(\left(\left(D_{P_{aA}} - \left(\sum_{k,l} \varepsilon'_{rr_{P_k,P_l}} d\tau\right) t^2\right) \bigg/ \left(\sum_{k,l} \varepsilon'_{cc_{P_k,P_l}} d\tau\right)\right)^{\frac{1}{2}}\right) - 0 \bigg/ S^{'3}_{2,P_{aA}};$$

$$a_{2,P_{aA}}(t) = S_{2,P_{aA}}'' \cdot T_{2,P_{aA}}(t) + \kappa_{2,P_{aA}}(t) \cdot N_{2,P_{aA}}(t)$$

$$T_{3,P_{aA}}(t) = \phi_{3,P_{aA}}(t)' / |\phi_{3,P_{aA}}(t)'|;$$

$$S_{3,P_{aA}} = \int_{t_o}^{t} \varphi_{3,P_{aA}}(u)' du;$$

$$\kappa_{3,P_{aA}}(t) \cdot N_{3,P_{aA}}(t) = \frac{dT_{2,P_{aA}}}{ds};$$

$$\kappa_{3,P_{aA}}(t) = \left(\left(\left(D_{P_{aA}} - \left(\sum_{k,l} \varepsilon'_{u_{P_k,P_l}} d\tau\right) t^2\right) \bigg/ \left(\sum_{k,l} \varepsilon'_{u_{P_k,P_l}} d\tau\right)\right)^{\frac{1}{2}}\right) - 0 \bigg/ S^{'3}_{3,P_{aA}};$$

$$a_{3,P_{aA}}(t) = S_{3,P_{aA}} \cdot T_{3,P_{aA}}(t) + \kappa_{3,P_{aA}}(t) \cdot N_{3,P_{aA}}(t)$$

If $(x_1, x_2, x_3, t)$ is the coordinate system of the red blood cell in a neighbourhood $O_{P_{mA}}$ of the basal anterior and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{aA}}$, $C_{2,P_{aA}}$ and $C_{3,P_{aA}}$ are the graphs of $\phi_{1,P_{aA}}(t)$, $\phi_{2,P_{aA}}(t)$ and $\phi_{3,P_{aA}}(t)$ respectively then the mechanical parameters of the red blood cells in the region $O_{P_{mA}}$ are realized by the following formulas:

$$v_{1,P_{aA}}(t) = \int_{C_{1,P_{aA}}} T_{1,P_{aA}}(t) \otimes \delta(x_1, x_2, x_3, t) d\tau;$$

-continued $$n_{1,P_{aA}}(t) = \int_{C_1,P_{aA}} N_{1,P_{aA}}(t) \otimes \delta(x_1, x_2, x_3, t)dt;$$

$$a_{1,P_{aA}}^{RBC}(t) = \int_{C_1,P_{aA}} a_{1,P_{aA}}(t) \otimes \delta(x_1, x_2, x_3, t)dt$$

$$v_{2,P_{aA}}(t) = \int_{C_2,P_{aA}} T_{2,P_{aA}}(t) \otimes \delta(x_1, x_2, x_3, t)dt;$$

$$n_{2,P_{aA}}(t) = \int_{C_2,P_{aA}} N_{2,P_{aA}}(t) \otimes \delta(x_1, x_2, x_3, t)dt;$$

$$a_{2,P_{aA}}^{RBC}(t) = \int_{C_2,P_{aA}} a_{2,P_{aA}}(t) \otimes \delta(x_1, x_2, x_3, t)dt$$

$$v_{3,P_{aA}}(t) = \int_{C_3,P_{aA}} T_{3,P_{aA}}(t) \otimes \delta(x_1, x_2, x_3, t)dt;$$

$$n_{3,P_{aA}}(t) = \int_{C_3,P_{aA}} N_{3,P_{aA}}(t) \otimes \delta(x_1, x_2, x_3, t)dt;$$

$$a_{3,P_{aA}}^{RBC}(t) = \int_{C_3,P_{aA}} a_{3,P_{aA}}(t) \otimes \delta(x_1, x_2, x_3, t)dt$$

Figure 10:
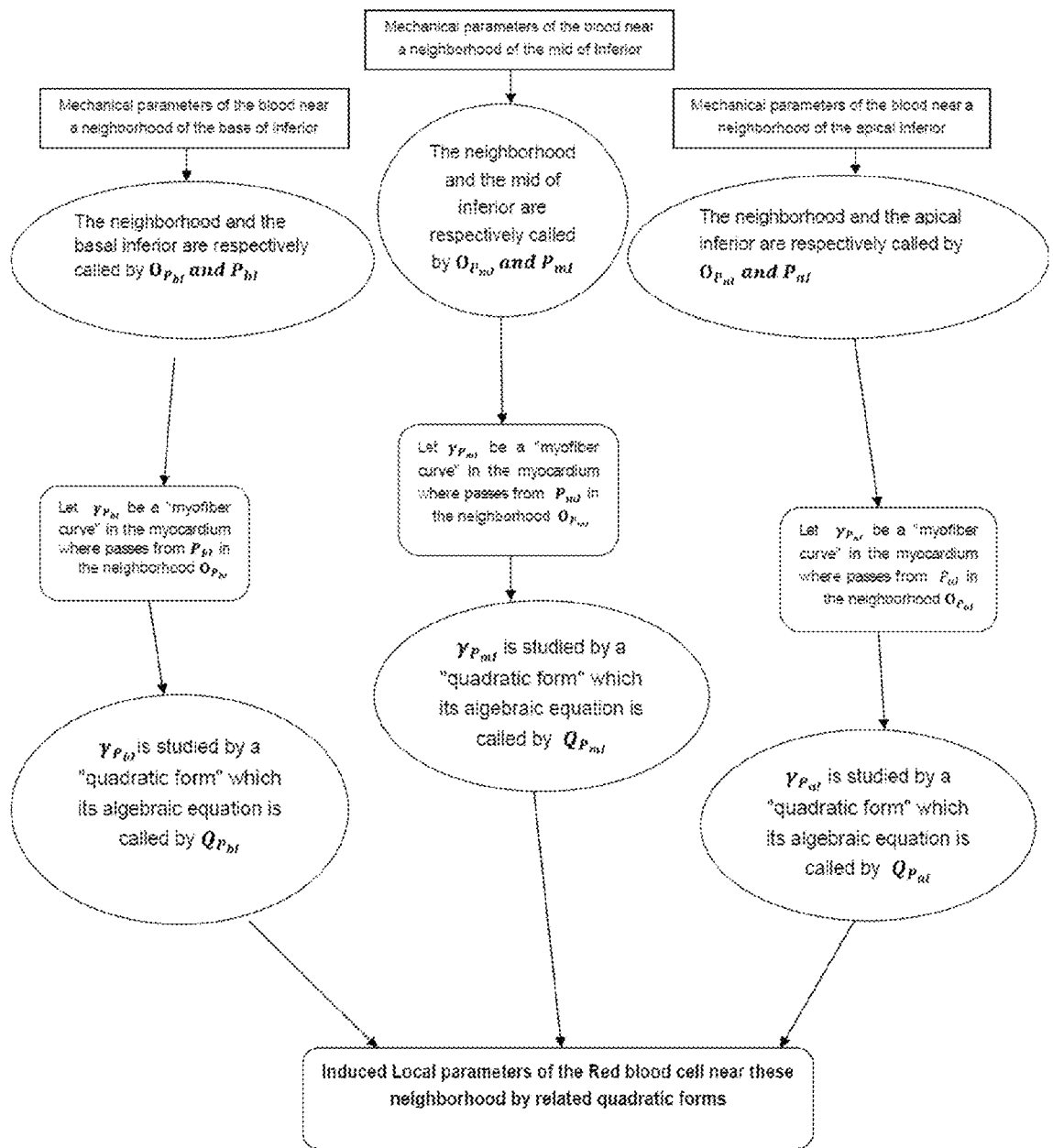
FIG. 10 shows a flowchart where states the basal, mid and apical Inferior as three echocardiography samples in the left ventricle, in their corresponded regions.
Figure 11:
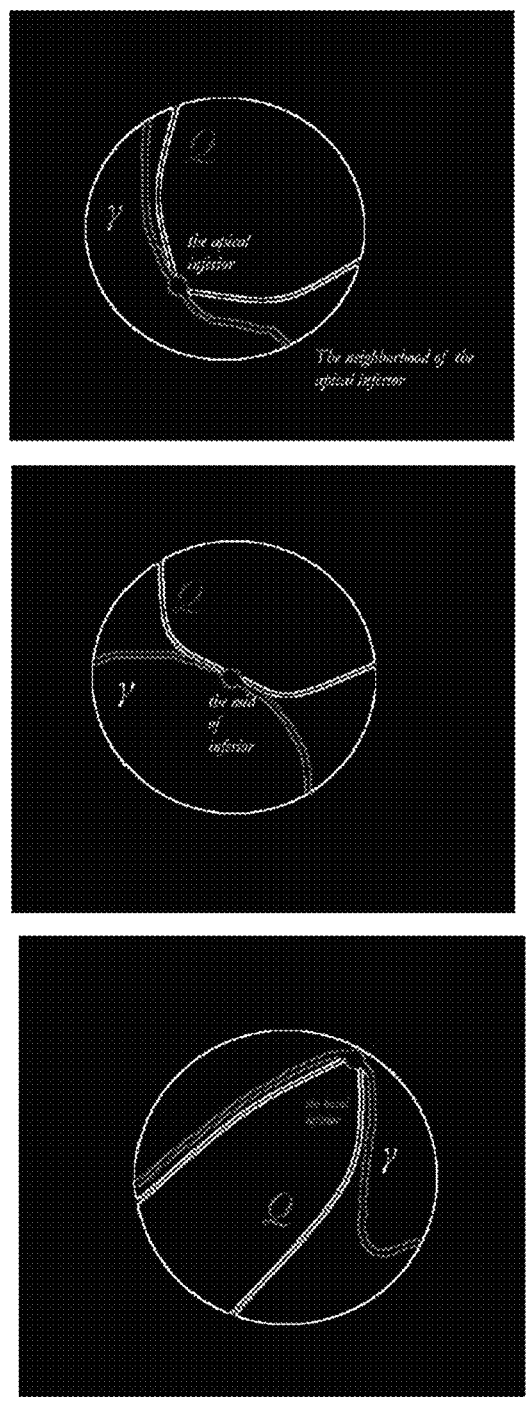
FIG. 11 shows three rendering of the basal, mid and apical inferior in their corresponded regions at Mathlab software.

In an embodiment the invention provides mathematical signs of the basal Inferior and the mid of Inferior and the apical Inferior in their corresponded regions to gain good formulizations of the induced mechanical parameters of the blood, as shown in FIG. 10.

Accordingly, let $\epsilon_{rr,P_{bl}}$, $\epsilon_{ll,P_{bl}}$ and $\epsilon_{cc,P_{bl}}$ be the strain components of the basal Inferior $P_{bl}$, then $\gamma_{P_{bl}}$={each myocardial sample $X$ that $\epsilon_{rr,X} \times \epsilon_{ll,X} = \epsilon_{rr,P_{bl}} \times \epsilon_{ll,P_{bl}}$ and $\epsilon_{rr,X} \times \epsilon_{ll,X} \times \epsilon_{cc,X} = \epsilon_{rr,P_{bl}} \times \epsilon_{ll,P_{bl}} \times \epsilon_{cc,P_{bl}}$} similarly for mid and apical inferior the sets are:

$\gamma_{P_{ml}}$={each myocardial sample $X$ that $\epsilon_{rr,X} \times \epsilon_{ll,X} = \epsilon_{rr,P_{ml}} \times \epsilon_{ll,P_{ml}}$ and $\epsilon_{rr,X} \times \epsilon_{ll,X} \times \epsilon_{cc,X} = \epsilon_{rr,P_{ml}} \times \epsilon_{ll,P_{ml}} \times \epsilon_{cc,P_{ml}}$}

$\gamma_{P_{al}}$={each myocardial sample $X$ that $\epsilon_{rr,X} \times \epsilon_{ll,X} = \epsilon_{rr,P_{al}} \times \epsilon_{ll,P_{al}}$ and $\epsilon_{rr,X} \times \epsilon_{ll,X} \times \epsilon_{cc,X} = \epsilon_{rr,P_{al}} \times \epsilon_{ll,P_{al}} \times \epsilon_{cc,P_{al}}$}

$\gamma_{P_{bl}}$, $\gamma_{P_{ml}}$ and $\gamma_{P_{al}}$ are the myofiber bands illustrated in FIG. 2. The Q's have following values $$Q_{P_{bl}} : D_{P_{bl}} = \left(\sum_{k,l} \varepsilon_{rr_{P_k},P_l} dt\right) \cdot y_1^2 + \left(\sum_{k,l} \varepsilon_{ll_{P_k},P_l} dt\right) \cdot y_2^2 + \left(\sum_{k,l} \varepsilon_{cc_{P_k},P_l} dt\right) \cdot y_3^2$$

$$D_{P_{bl}} = \left(\sum_{k,l} \varepsilon_{rr_{P_k},P_l} dt\right) \cdot y_{1,bl}^2 + \left(\sum_{k,l} \varepsilon_{ll_{P_k},P_l} dt\right) \cdot y_{2,bl}^2 + \left(\sum_{k,l} \varepsilon_{cc_{P_k},P_l} dt\right) \cdot y_{3,bl}^2$$

Where, $P_k$ and $P_l$ are points belonging to $\gamma_{P_{bl}} \cap O_{P_{bl}}$ and if $P_{bl}=(y_{1,bl}, y_{2,bl}, y_{3,bl})$ as Cartesian coordinate Similarly, the Cartesian coordinates for Q's for mid and apical Inferiors are as follows;

For the mid of Anterior:

$$Q_{P_{ml}} : D_{P_{ml}} = \left(\sum_{k,l} \varepsilon_{rr_{P_k},P_l} dt\right) \cdot y_1^2 + \left(\sum_{k,l} \varepsilon_{ll_{P_k},P_l} dt\right) \cdot y_2^2 + \left(\sum_{k,l} \varepsilon_{cc_{P_k},P_l} dt\right) \cdot y_3^2$$

$$D_{P_{ml}} = \left(\sum_{k,l} \varepsilon_{rr_{P_k},P_l} dt\right) \cdot y_{1,ml}^2 +$$

$$\left(\sum_{k,l} \varepsilon_{ll_{P_k},P_l} dt\right) \cdot y_{2,ml}^2 + \left(\sum_{k,l} \varepsilon_{cc_{P_k},P_l} dt\right) \cdot y_{3,ml}^2$$

where, $P_k$ and $P_l$ are points belonging to $\gamma_{P_{ml}} \cap O_{P_{ml}}$ and if $P_{ml}=(y_{1,ml}, y_{2,ml}, y_{3,ml})$ as Cartesian coordinate.

For apical Anterior:

$$Q_{P_{al}} : D_{P_{al}} = \left(\sum_{k,l} \varepsilon_{rr_{P_k},P_l} dt\right) \cdot y_1^2 + \left(\sum_{k,l} \varepsilon_{ll_{P_k},P_l} dt\right) \cdot y_2^2 + \left(\sum_{k,l} \varepsilon_{cc_{P_k},P_l} dt\right) \cdot y_3^2$$

$$D_{P_{al}} = \left(\sum_{k,l} \varepsilon_{rr_{P_k},P_l} dt\right) \cdot y_{1,al}^2 +$$

$$\left(\sum_{k,l} \varepsilon_{ll_{P_k},P_l} dt\right) \cdot y_{2,al}^2 + \left(\sum_{k,l} \varepsilon_{cc_{P_k},P_l} dt\right) \cdot y_{3,al}^2$$

where, $P_k$ and $P_l$ are points belonging to $\gamma_{P_{al}} \cap O_{P_{al}}$ and if $P_{al}=(y_{1,al}, y_{2,al}, y_{3,al})$ as Cartesian coordinate.

Figure 13:
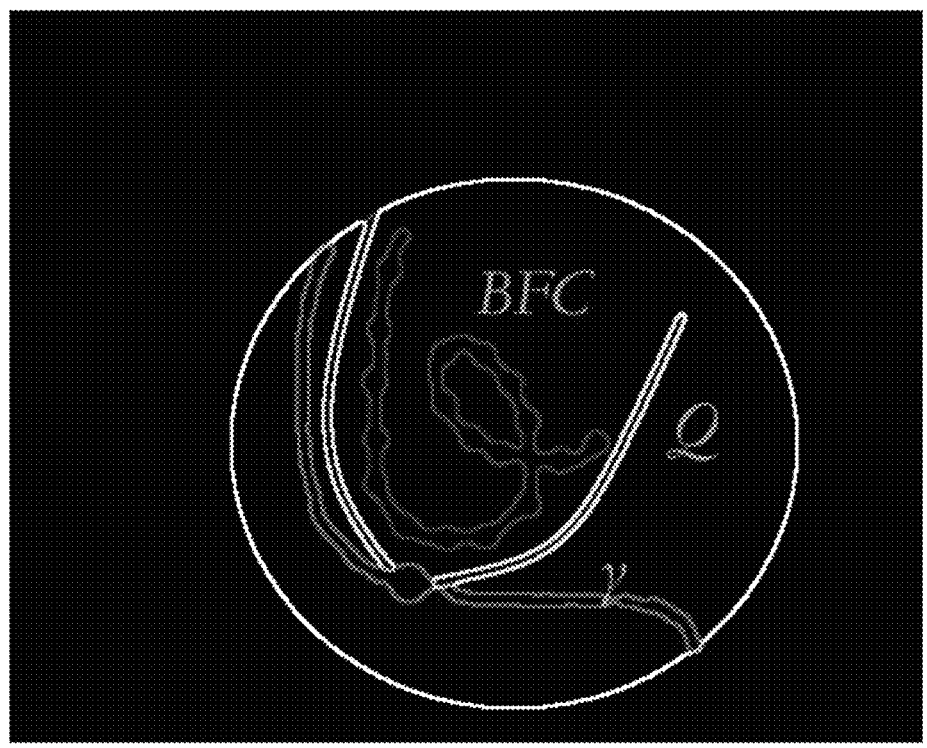
FIG. 13 shows the blood flow curve near the corresponded neighbourhood of the apical Inferior in the myocardium of the left ventricle where has been rendered at Mathlab software.

In a preferred embodiment, the invention provides an analytical solution of the Navier-Stocks equations in the region $O_{P_{al}}$ of the apical Inferior. FIG. 13 shows a rendering of these solutions in the mathlab software.

Figure 12:
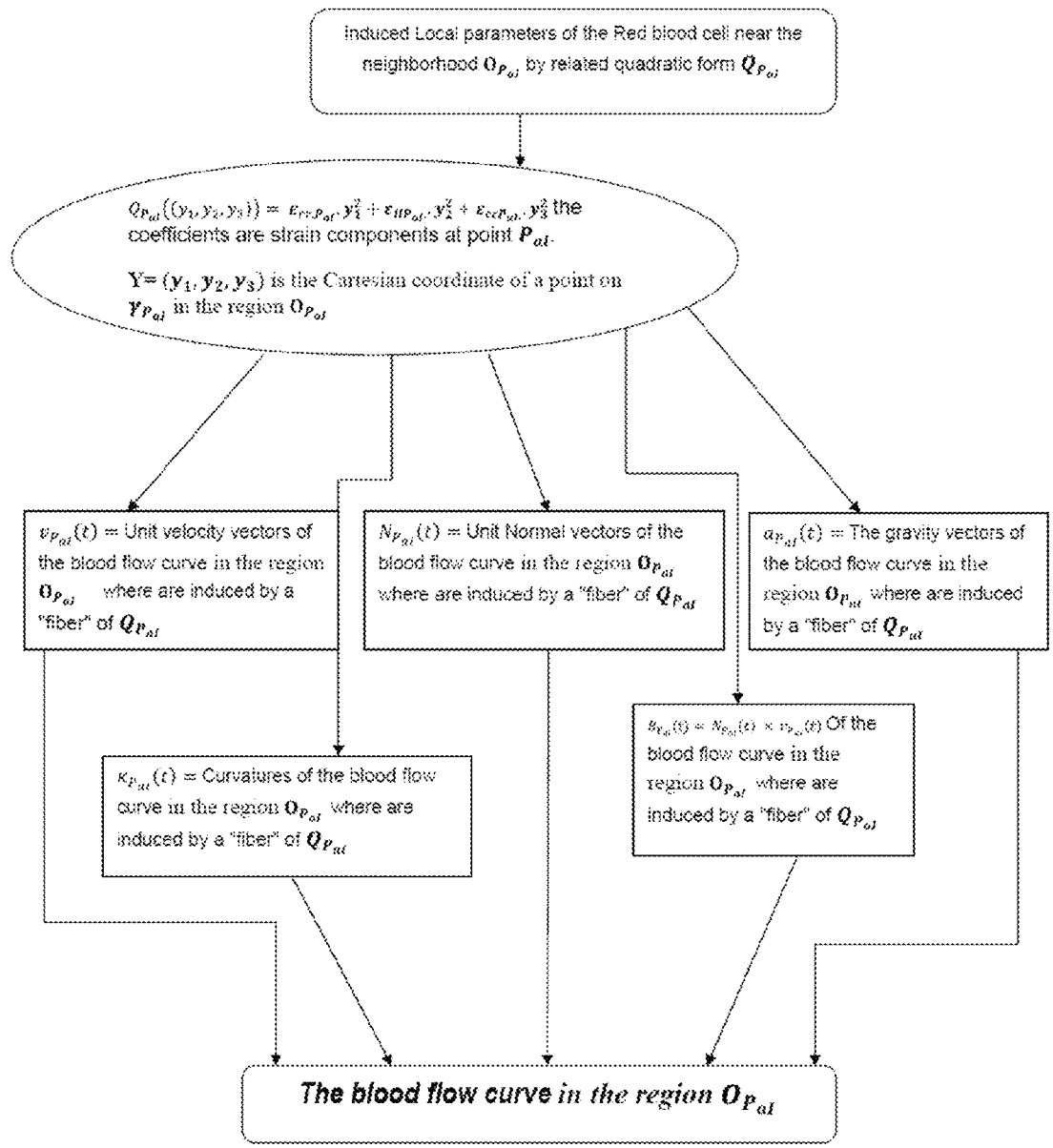
FIG. 12 shows a flowchart that models the blood flow curve near a neighbourhood of the apical Inferior in the myocardium of the left ventricle.

FIG. 12 shows the mechanical parameters of blood which were induced by $Q_{P_{al}}$ in region $O_{P_{al}}$ related to apical inferior. The surface is;

$$F_{P_{al}}((y_1, y_2, y_3)) = \left(\sum_{k,l} \varepsilon'_{rr_{P_k},P_l} dt\right) \cdot y_1^2 + \left(\sum_{k,l} \varepsilon'_{ll_{P_k},P_l} dt\right) \cdot y_2^2 + \left(\sum_{k,l} \varepsilon'_{cc_{P_k},P_l} dt\right) \cdot y_3^2 - D_{P_{al}}$$

In the region $O_{P_{al}}$, let $\phi_{1,P_{al}}(t)$, $\phi_{2,P_{al}}(t)$ and $\phi_{3,P_{al}}(t)$ are parameterized forms of the projections of the surface $F_{P_{al}}$ on xy-axis and yz-axis:

$$\varphi_{1,P_{al}}(t) = \left(t, \left(\left(D_{P_{al}} - \left(\sum_{k,l} \varepsilon'_{rr_{P_k},P_l} dt\right)t^2\right) / \left(\sum_{k,l} \varepsilon'_{ll_{P_k},P_l} dt\right)\right)^{\frac{1}{2}}\right);$$

$$\varphi_{2,P_{al}}(t) = \left(t, \left(\left(D_{P_{al}} - \left(\sum_{k,l} \varepsilon'_{rr_{P_k},P_l} dt\right)t^2\right) / \left(\sum_{k,l} \varepsilon'_{cc_{P_k},P_l} dt\right)\right)^{\frac{1}{2}}\right);$$

$$\varphi_{3,P_{al}}(t) = \left(t, \left(\left(D_{P_{al}} - \left(\sum_{k,l} \varepsilon'_{ll_{P_k},P_l} dt\right)t^2\right) / \left(\sum_{k,l} \varepsilon'_{cc_{P_k},P_l} dt\right)\right)^{\frac{1}{2}}\right)$$

Following formulae were set;

$$T_{1,P_{al}}(t) = \phi_{1,P_{al}}(t)' / |\phi_{1,P_{al}}(t)'|;$$

$$S_{1,P_{al}} = \int_{t_0}^{t} \varphi_{1,P_{al}}(u)' du;$$

$$\kappa_{1,P_{al}}(t) \cdot N_{1,P_{al}}(t) = \frac{dT_{1,P_{al}}}{ds};$$

-continued $$\kappa_{1,P_{al}}(t) = \left(\left(\left(D_{P_{al}} - \left(\sum_{k,l} \varepsilon'_{rr_{P_k,P_l}} dt\right)t^2\right)\middle/\left(\sum_{k,l} \varepsilon'_{u_{P_k,P_l}} dt\right)\right)^{\frac{1}{2}}\right) - 0\bigg/S'^3_{1,P_{al}};$$

$$a_{1,P_{al}}(t) = S_{1,P_{al}}'' \cdot T_{1,P_{al}}(t) + \kappa_{1,P_{al}}(t) \cdot N_{1,P_{al}}(t)$$

$$T_{2,P_{al}}(t) = \phi_{2,P_{al}}(t)' / |\phi_{2,P_{al}}(t)'|;$$

$$S_{2,P_{al}} = \int_{t_o}^{t} \varphi_{2,P_{al}}(u)' \, du;$$

$$\kappa_{2,P_{al}}(t) \cdot N_{2,P_{al}}(t) = \frac{dT_{2,P_{al}}}{ds};$$

$$\kappa_{2,P_{al}}(t) = \left(\left(\left(D_{P_{al}} - \left(\sum_{k,l} \varepsilon'_{rr_{P_k,P_l}} dt\right)t^2\right)\middle/\left(\sum_{k,l} \varepsilon'_{cc_{P_k,P_l}} dt\right)\right)^{\frac{1}{2}}\right) - 0\bigg/S'^3_{2,P_{al}};$$

$$a_{2,P_{al}}(t) = S_{2,P_{al}}'' \cdot T_{2,P_{al}}(t) + \kappa_{2,P_{al}}(t) \cdot N_{2,P_{al}}(t)$$

$$T_{3,P_{al}}(t) = \phi_{3,P_{al}}(t)' / |\phi_{3,P_{al}}(t)'|;$$

$$S_{3,P_{al}} = \int_{t_o}^{t} \varphi_{3,P_{al}}(u)' \, du;$$

$$\kappa_{3,P_{al}}(t) \cdot N_{3,P_{al}}(t) = \frac{dT_{2,P_{al}}}{ds};$$

$$\kappa_{3,P_{al}}(t) = \left(\left(\left(D_{P_{al}} - \left(\sum_{k,l} \varepsilon'_{u_{P_k,P_l}} dt\right)t^2\right)\middle/\left(\sum_{k,l} \varepsilon'_{u_{P_k,P_l}} dt\right)\right)^{\frac{1}{2}}\right) - 0\bigg/S'^3_{3,P_{al}};$$

$$a_{3,P_{al}}(t) = S_{3,P_{al}}'' \cdot T_{3,P_{al}}(t) + \kappa_{3,P_{al}}(t) \cdot N_{3,P_{al}}(t)$$

$(x_1, x_2, x_3, t)$ is the coordinate system of the red blood cell in a neighbourhood $O_{P_{al}}$ of the apical Inferior and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{al}}$, $C_{2,P_{al}}$ and $C_{3,P_{al}}$ are the graphs of $\phi_{1,P_{al}}(t)$, $\phi_{2,P_{al}}(t)$ and $\phi_{3,P_{al}}(t)$ respectively then the mechanical parameters of the red blood cells in the region $O_{P_{al}}$ are calculated by the following formulae:

$$v_{1,P_{al}}(t) = \int_{C_{1,P_{al}}} T_{1,P_{al}}(t) \otimes \delta(x_1, x_2, x_3, t) \, dt;$$

$$n_{1,P_{al}}(t) = \int_{C_{1,P_{al}}} N_{1,P_{al}}(t) \otimes \delta(x_1, x_2, x_3, t) \, dt;$$

$$a^{RBC}_{1,P_{al}}(t) = \int_{C_{1,P_{al}}} a_{1,P_{al}}(t) \otimes \delta(x_1, x_2, x_3, t) \, dt;$$

$$v_{2,P_{al}}(t) = \int_{C_{2,P_{al}}} T_{2,P_{al}}(t) \otimes \delta(x_1, x_2, x_3, t) \, dt;$$

$$n_{2,P_{al}}(t) = \int_{C_{2,P_{al}}} N_{2,P_{al}}(t) \otimes \delta(x_1, x_2, x_3, t) \, dt;$$

$$a^{RBC}_{2,P_{al}}(t) = \int_{C_{2,P_{al}}} a_{2,P_{al}}(t) \otimes \delta(x_1, x_2, x_3, t) \, dt;$$

$$v_{3,P_{al}}(t) = \int_{C_{3,P_{al}}} T_{3,P_{al}}(t) \otimes \delta(x_1, x_2, x_3, t) \, dt;$$

$$n_{3,P_{al}}(t) = \int_{C_{3,P_{al}}} N_{3,P_{al}}(t) \otimes \delta(x_1, x_2, x_3, t) \, dt;$$

$$a^{RBC}_{3,P_{al}}(t) = \int_{C_{3,P_{al}}} a_{3,P_{al}}(t) \otimes \delta(x_1, x_2, x_3, t) \, dt$$

Figure 15:
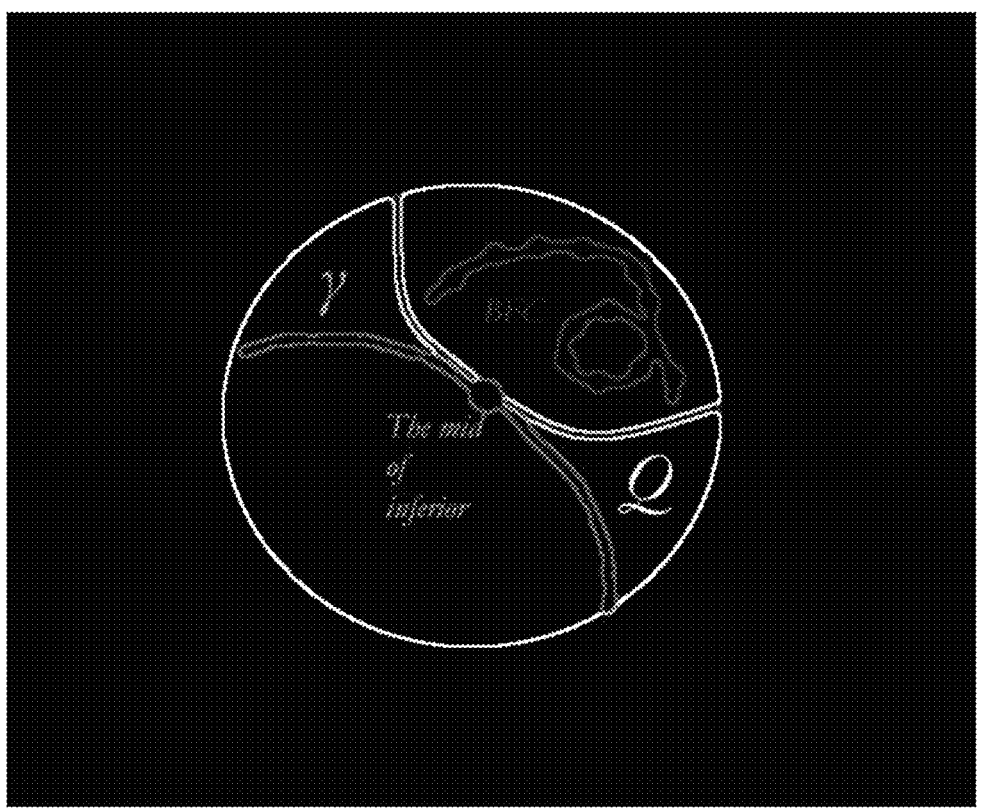
FIG. 15 shows the blood flow curve near the corresponded neighborhood of the mid Inferior in the myocardium of the left ventricle where has been rendered at Mathlab software.

In another preferred embodiment the invention provides an analytical solution of the Navier-Stocks equations in the region $O_{P_{ml}}$ of the mid Inferior. FIG. 15 shows a rendering of these solutions in the mathlab software.

Figure 14:
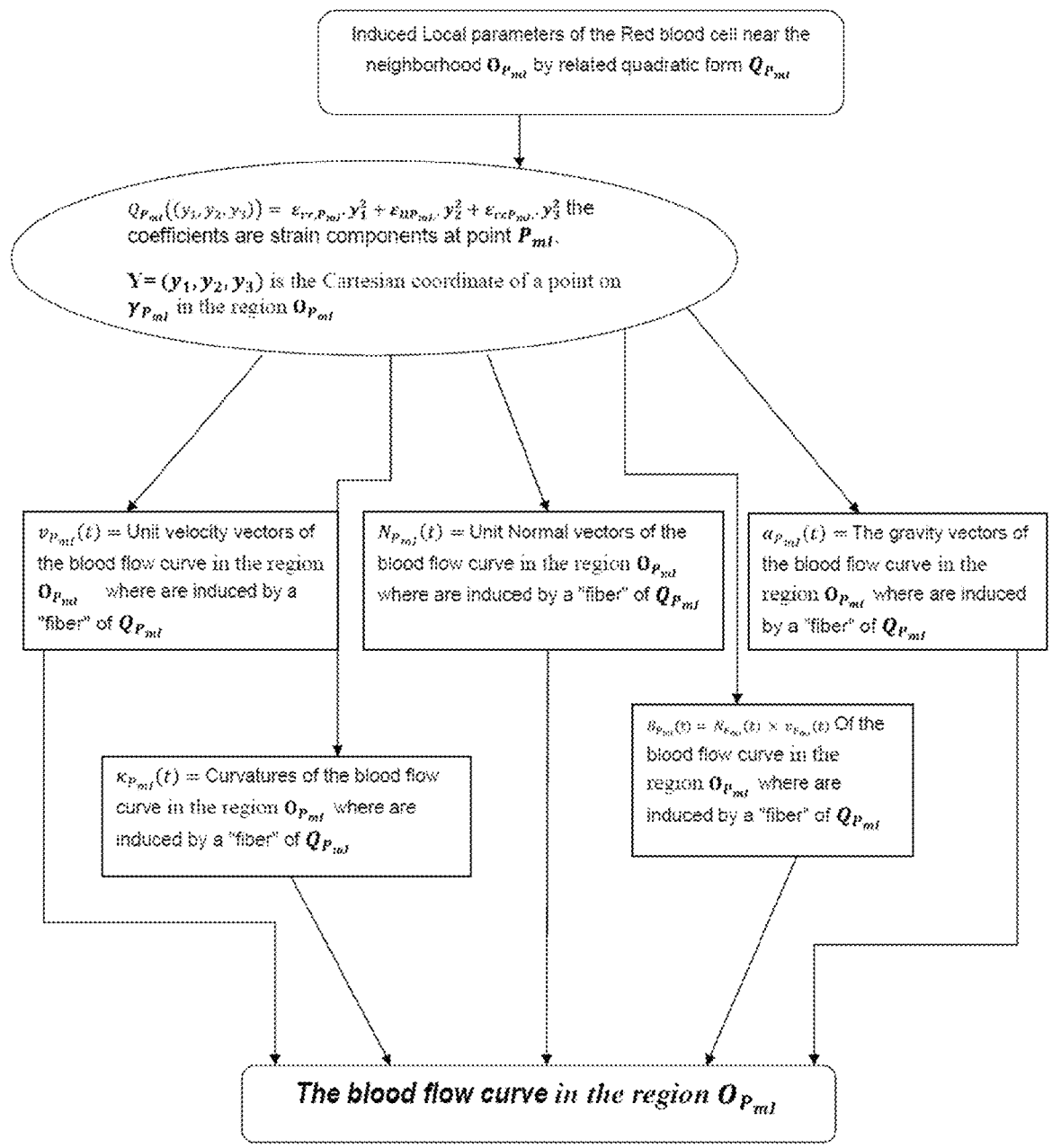
FIG. 14 shows a flowchart that models the blood flow curve near a neighborhood of the mid Inferior in the myocardium of the left ventricle.

FIG. 14 shows the mechanical parameters of blood which were induced by $Q_{P_{ml}}$ in region $O_{P_{ml}}$ related to apical inferior. The surface is;

$$F_{P_{ml}}((y_1, y_2, y_3)) = \left(\sum_{k,l} \varepsilon'_{rr_{P_k,P_l}} dt\right) \cdot y_1^2 + \left(\sum_{k,l} \varepsilon'_{u_{P_k,P_l}} dt\right) \cdot y_2^2 + \left(\sum_{k,l} \varepsilon'_{cc_{P_k,P_l}} dt\right) \cdot y_3^2 - D_{P_{ml}}$$

In the region $O_{P_{ml}}$, let $\phi_{1,P_{ml}}(t)$, $\phi_{2,P_{ml}}(t)$ and $\phi_{3,P_{ml}}(t)$ are parameterized forms of the projections of the surface $F_{P_{ml}}$ on xy-axis and yz-axis:

$$\varphi_{1,P_{ml}}(t) = \left(t, \left(\left(D_{P_{ml}} - \left(\sum_{k,l} \varepsilon'_{rr_{P_k,P_l}} dt\right)t^2\right)\middle/\left(\sum_{k,l} \varepsilon'_{u_{P_k,P_l}} dt\right)\right)^{\frac{1}{2}}\right);$$

$$\varphi_{2,P_{ml}}(t) = \left(t, \left(\left(D_{P_{ml}} - \left(\sum_{k,l} \varepsilon'_{rr_{P_k,P_l}} dt\right)t^2\right)\middle/\left(\sum_{k,l} \varepsilon'_{cc_{P_k,P_l}} dt\right)\right)^{\frac{1}{2}}\right);$$

$$\varphi_{3,P_{ml}}(t) = \left(t, \left(\left(D_{P_{ml}} - \left(\sum_{k,l} \varepsilon'_{u_{P_k,P_l}} dt\right)t^2\right)\middle/\left(\sum_{k,l} \varepsilon'_{cc_{P_k,P_l}} dt\right)\right)^{\frac{1}{2}}\right)$$

Following formulae were set;

$$T_{1,P_{ml}}(t) = \phi_{1,P_{ml}}(t)' / |\phi_{1,P_{ml}}(t)'|;$$

$$S_{1,P_{ml}} = \int_{t_o}^{t} \varphi_{1,P_{ml}}(u)' \, du;$$

$$\kappa_{1,P_{ml}}(t) \cdot N_{1,P_{ml}}(t) = \frac{dT_{1,P_{ml}}}{ds};$$

$$\kappa_{1,P_{ml}}(t) = \left(\left(\left(D_{P_{ml}} - \left(\sum_{k,l} \varepsilon'_{rr_{P_k,P_l}} dt\right)t^2\right)\middle/\left(\sum_{k,l} \varepsilon'_{u_{P_k,P_l}} dt\right)\right)^{\frac{1}{2}}\right) - 0\bigg/S'^3_{1,P_{ml}};$$

$$a_{1,P_{ml}}(t) = S_{1,P_{ml}}'' \cdot T_{1,P_{ml}}(t) + \kappa_{1,P_{ml}}(t) \cdot N_{1,P_{ml}}(t)$$

$$T_{2,P_{ml}}(t) = \phi_{2,P_{ml}}(t)' / |\phi_{2,P_{ml}}(t)'|;$$

$$S_{2,P_{ml}} = \int_{t_o}^{t} \varphi_{2,P_{ml}}(u)' \, du;$$

$$\kappa_{2,P_{ml}}(t) \cdot N_{2,P_{ml}}(t) = \frac{dT_{2,P_{ml}}}{ds};$$

$$\kappa_{2,P_{ml}}(t) =$$

$$\left(\left(\left(D_{P_{ml}} - \left(\sum_{k,l} \varepsilon'_{rr_{P_k},P_l} \, dt\right)t^2\right) \Big/ \left(\sum_{k,l} \varepsilon'_{cc_{P_k},P_l} \, dt\right)\right)^{\frac{1}{2}} - 0 \Big/ S'^3_{2,P_{ml}};$$

$$a_{2,P_{ml}}(t) = S_{2,P_{ml}}'' \cdot T_{2,P_{ml}}(t) + \kappa_{2,P_{ml}}(t) \cdot N_{2,P_{ml}}(t)$$

$$T_{3,P_{ml}}(t) = \phi_{3,P_{ml}}(t)' / |\phi_{3,P_{ml}}(t)'|;$$

$$S_{3,P_{ml}} = \int_{t_o}^{t} \varphi_{3,P_{ml}}(u)' \, du;$$

$$\kappa_{3,P_{ml}}(t) \cdot N_{3,P_{ml}}(t) = \frac{dT_{2,P_{ml}}}{ds};$$

$$\kappa_{3,P_{ml}}(t) =$$

$$\left(\left(\left(D_{P_{ml}} - \left(\sum_{k,l} \varepsilon'_{u_{P_k},P_l} \, dt\right)t^2\right) \Big/ \left(\sum_{k,l} \varepsilon'_{u_{P_k},P_l} \, dt\right)\right)^{\frac{1}{2}} - 0 \Big/ S'^3_{3,P_{ml}};$$

$$a_{3,P_{ml}}(t) = S_{3,P_{ml}}'' \cdot T_{3,P_{ml}}(t) + \kappa_{3,P_{ml}}(t) \cdot N_{3,P_{ml}}(t)$$

$(x_1, x_2, x_3, t)$ is the coordinate system of the red blood cell in a neighbourhood $O_{P_{ml}}$ of the mid Inferior and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{ml}}$, $C_{2,P_{ml}}$ and $C_{3,P_{ml}}$ are the graphs of $\phi_{1,P_{ml}}(t)$, $\phi_{2,P_{ml}}(t)$ and $\phi_{3,P_{ml}}(t)$ respectively then the mechanical parameters of the red blood cells in the region $O_{P_{ml}}$ are calculated by the following formulae:

$$v_{1,P_{ml}}(t) = \int_{C_1,P_{ml}} T_{1,P_{ml}}(t) \otimes \delta(x_1, x_2, x_3, t) \, dt;$$

$$n_{1,P_{ml}}(t) = \int_{C_1,P_{ml}} N_{1,P_{ml}}(t) \otimes \delta(x_1, x_2, x_3, t) \, dt;$$

$$a_{1,P_{ml}}^{RBC}(t) = \int_{C_1,P_{ml}} a_{1,P_{ml}}(t) \otimes \delta(x_1, x_2, x_3, t) \, dt;$$

$$v_{2,P_{ml}}(t) = \int_{C_2,P_{ml}} T_{2,P_{ml}}(t) \otimes \delta(x_1, x_2, x_3, t) \, dt;$$

$$n_{2,P_{ml}}(t) = \int_{C_2,P_{ml}} N_{2,P_{ml}}(t) \otimes \delta(x_1, x_2, x_3, t) \, dt;$$

$$a_{2,P_{ml}}^{RBC}(t) = \int_{C_2,P_{ml}} a_{2,P_{ml}}(t) \otimes \delta(x_1, x_2, x_3, t) \, dt;$$

$$v_{3,P_{ml}}(t) = \int_{C_3,P_{ml}} T_{3,P_{ml}}(t) \otimes \delta(x_1, x_2, x_3, t) \, dt;$$

$$n_{3,P_{ml}}(t) = \int_{C_3,P_{ml}} N_{3,P_{ml}}(t) \otimes \delta(x_1, x_2, x_3, t) \, dt;$$

-continued $$a_{3,P_{ml}}^{RBC}(t) = \int_{C_3,P_{ml}} a_{3,P_{ml}}(t) \otimes \delta(x_1, x_2, x_3, t) \, dt$$

Figure 17:
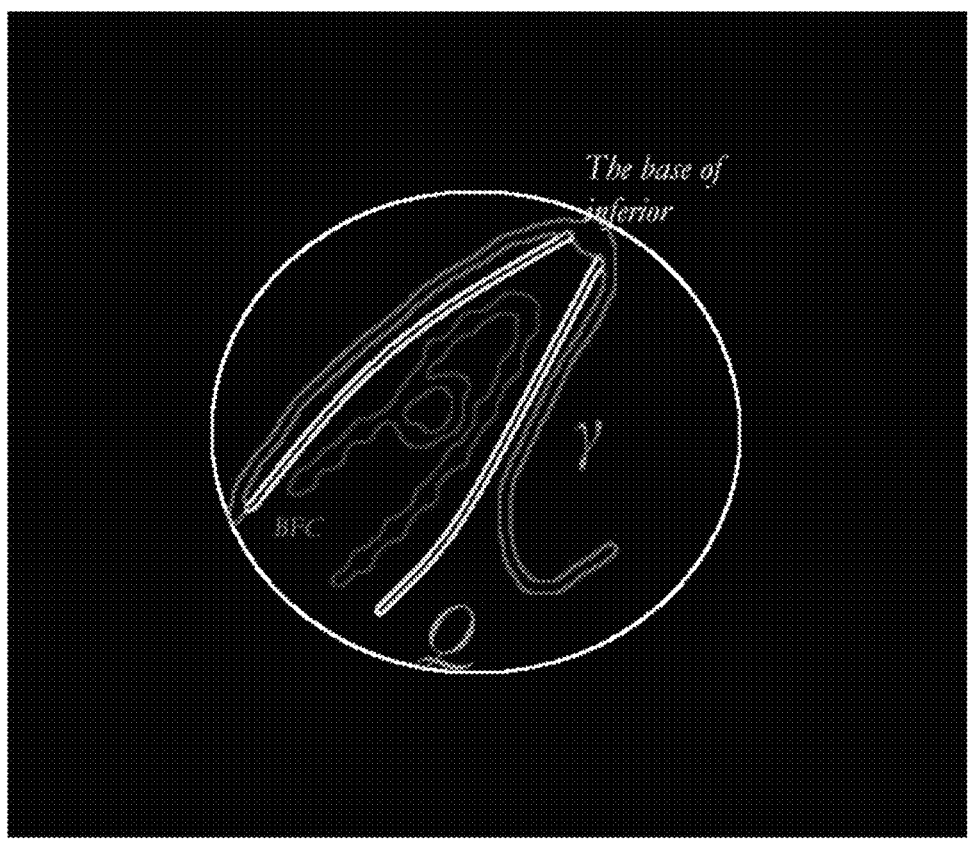
FIG. 17 shows the blood flow curve near the corresponded neighborhood of the basal Inferior in the myocardium of the left ventricle where has been rendered at Mathlab software.

In a preferred embodiment, the invention provides an analytical solution of the Navier-Stocks equations in the region $O_{P_{bl}}$ of the basal Inferior. FIG. 17 shows a rendering of these solutions in the mathlab software.

Figure 16:
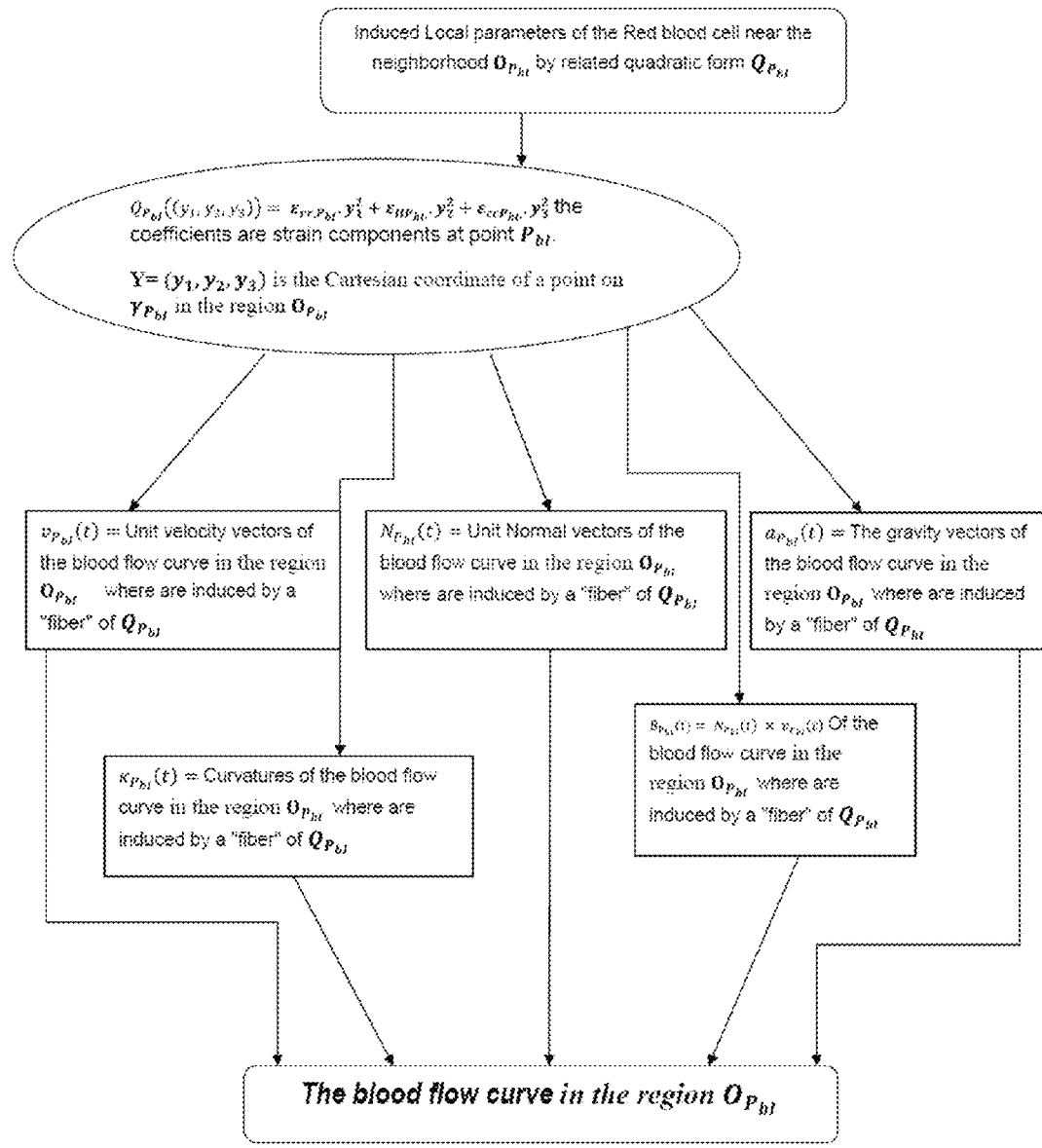
FIG. 16 shows a flowchart that models the blood flow curve near a neighborhood of the basal Inferior in the myocardium of the left ventricle.

FIG. 16 shows the mechanical parameters of blood which were induced by $Q_{P_{bl}}$ in region $O_{P_{bl}}$ related to apical inferior. The surface is;

$$F_{P_{bl}}((y_1, y_2, y_3)) = \left(\sum_{k,l} \varepsilon'_{rr_{P_k},P_l} \, dt\right) \cdot y_1^2 + \left(\sum_{k,l} \varepsilon'_{u_{P_k},P_l} \, dt\right) \cdot y_2^2 + \left(\sum_{k,l} \varepsilon'_{cc_{P_k},P_l} \, dt\right) \cdot y_3^2 - D_{P_{bl}}$$

In the region $O_{P_{bl}}$, let $\phi_{1,P_{bl}}(t)$, $\phi_{2,P_{bl}}(t)$ and $\phi_{3,P_{bl}}(t)$ are parameterized forms of the projections of the surface $F_{P_{bl}}$ on xy-axis and yz-axis:

$$\varphi_{1,P_{bl}}(t) = \left(t, \left(\left(D_{P_{bl}} - \left(\sum_{k,l} \varepsilon'_{rr_{P_k},P_l} \, dt\right)t^2\right) \Big/ \left(\sum_{k,l} \varepsilon'_{u_{P_k},P_l} \, dt\right)\right)^{\frac{1}{2}}\right);$$

$$\varphi_{2,P_{bl}}(t) = \left(t, \left(\left(D_{P_{bl}} - \left(\sum_{k,l} \varepsilon'_{rr_{P_k},P_l} \, dt\right)t^2\right) \Big/ \left(\sum_{k,l} \varepsilon'_{cc_{P_k},P_l} \, dt\right)\right)^{\frac{1}{2}}\right);$$

$$\varphi_{3,P_{bl}}(t) = \left(t, \left(\left(D_{P_{bl}} - \left(\sum_{k,l} \varepsilon'_{u_{P_k},P_l} \, dt\right)t^2\right) \Big/ \left(\sum_{k,l} \varepsilon'_{cc_{P_k},P_l} \, dt\right)\right)^{\frac{1}{2}}\right)$$

Following formulae were set;

$$T_{1,P_{bl}}(t) = \phi_{1,P_{bl}}(t)' / |\phi_{1,P_{bl}}(t)'|;$$

$$S_{1,P_{bl}} = \int_{t_o}^{t} \varphi_{1,P_{bl}}(u)' \, du;$$

$$\kappa_{1,P_{bl}}(t) \cdot N_{1,P_{bl}}(t) = \frac{dT_{1,P_{bl}}}{ds};$$

$$\kappa_{1,P_{bl}}(t) =$$

$$\left(\left(\left(D_{P_{bl}} - \left(\sum_{k,l} \varepsilon'_{rr_{P_k},P_l} \, dt\right)t^2\right) \Big/ \left(\sum_{k,l} \varepsilon'_{u_{P_k},P_l} \, dt\right)\right)^{\frac{1}{2}} - 0 \Big/ S'^3_{1,P_{bl}};$$

$$a_{1,P_{bl}}(t) = S_{1,P_{bl}}'' \cdot T_{1,P_{bl}}(t) + \kappa_{1,P_{bl}}(t) \cdot N_{1,P_{bl}}(t)$$

$$T_{2,P_{bl}}(t) = \phi_{2,P_{bl}}(t)' / |\phi_{2,P_{bl}}(t)'|;$$

$$S_{2,P_{bl}} = \int_{t_o}^{t} \varphi_{2,P_{bl}}(u)' \, du;$$

$$\kappa_{2,P_{bl}}(t) \cdot N_{2,P_{bl}}(t) = \frac{dT_{2,P_{bl}}}{ds};$$

-continued $$\kappa_{2,P_{bl}}(t) = \left[\left(\left(D_{P_{bl}} - \left(\sum_{k,l} \varepsilon'_{rr_{P_k,P_l}} dt\right)t^2\right) \middle/ \left(\sum_{k,l} \varepsilon'_{cc_{P_k,P_l}} dt\right)\right)^{\frac{1}{2}}\right] - 0 \middle/ S'^3_{2,P_{bl}};$$

$$a_{2,P_{bl}}(t) = S_{2,P_{bl}}'' \cdot T_{2,P_{bl}}(t) + \kappa_{2,P_{bl}}(t) \cdot N_{2,P_{bl}}(t)$$

$$T_{3,P_{bl}}(t) = \phi_{3,P_{bl}}(t)' / |\phi_{3,P_{bl}}(t)'|;$$

$$S_{3,P_{bl}} = \int_{t_o}^{t} \varphi_{3,P_{bl}}(u)' du;$$

$$\kappa_{3,P_{bl}}(t) \cdot N_{3,P_{bl}}(t) = \frac{dT_{2,P_{bl}}}{ds};$$

$$\kappa_{3,P_{bl}}(t) = \left[\left(\left(D_{P_{bl}} - \left(\sum_{k,l} \varepsilon'_{ll_{P_k,P_l}} dt\right)t^2\right) \middle/ \left(\sum_{k,l} \varepsilon'_{ll_{P_k,P_l}} dt\right)\right)^{\frac{1}{2}}\right] - 0 \middle/ S'^3_{3,P_{bl}};$$

$$a_{3,P_{bl}}(t) = S_{3,P_{bl}}' \cdot T_{3,P_{bl}}(t) + \kappa_{3,P_{bl}}(t) \cdot N_{3,P_{bl}}(t)$$

$(x_1, x_2, x_3, t)$ is the coordinate system of the red blood cell in a neighbourhood $O_{P_{bl}}$ of the basal inferior and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{ml}}, C_{2,P_{ml}}$ and $C_{3,P_{ml}}$ are the graphs of $\phi_{1,P_{bl}}(t), \phi_{2,P_{bl}}(t)$ and $\phi_{3,P_{bl}}(t)$ respectively then the mechanical parameters of the red blood cells in the region $O_{P_{bl}}$ are calculated by the following formulae:

$$v_{1,P_{bl}}(t) = \int_{C_{1,P_{bl}}} T_{1,P_{bl}}(t) \otimes \delta(x_1, x_2, x_3, t) dt;$$

$$n_{1,P_{bl}}(t) = \int_{C_{1,P_{bl}}} N_{1,P_{bl}}(t) \otimes \delta(x_1, x_2, x_3, t) dt;$$

$$a^{RBC}_{1,P_{bl}}(t) = \int_{C_{1,P_{bl}}} a_{1,P_{bl}}(t) \otimes \delta(x_1, x_2, x_3, t) dt$$

$$v_{2,P_{bl}}(t) = \int_{C_{2,P_{bl}}} T_{2,P_{bl}}(t) \otimes \delta(x_1, x_2, x_3, t) dt;$$

$$n_{2,P_{bl}}(t) = \int_{C_{2,P_{bl}}} N_{2,P_{bl}}(t) \otimes \delta(x_1, x_2, x_3, t) dt;$$

$$a^{RBC}_{2,P_{bl}}(t) = \int_{C_{2,P_{bl}}} a_{2,P_{bl}}(t) \otimes \delta(x_1, x_2, x_3, t) dt$$

$$v_{3,P_{bl}}(t) = \int_{C_{3,P_{bl}}} T_{3,P_{bl}}(t) \otimes \delta(x_1, x_2, x_3, t) dt;$$

$$n_{3,P_{bl}}(t) = \int_{C_{3,P_{bl}}} N_{3,P_{bl}}(t) \otimes \delta(x_1, x_2, x_3, t) dt;$$

$$a^{RBC}_{3,P_{bl}}(t) = \int_{C_{3,P_{bl}}} a_{3,P_{bl}}(t) \otimes \delta(x_1, x_2, x_3, t) dt$$

Figure 18:
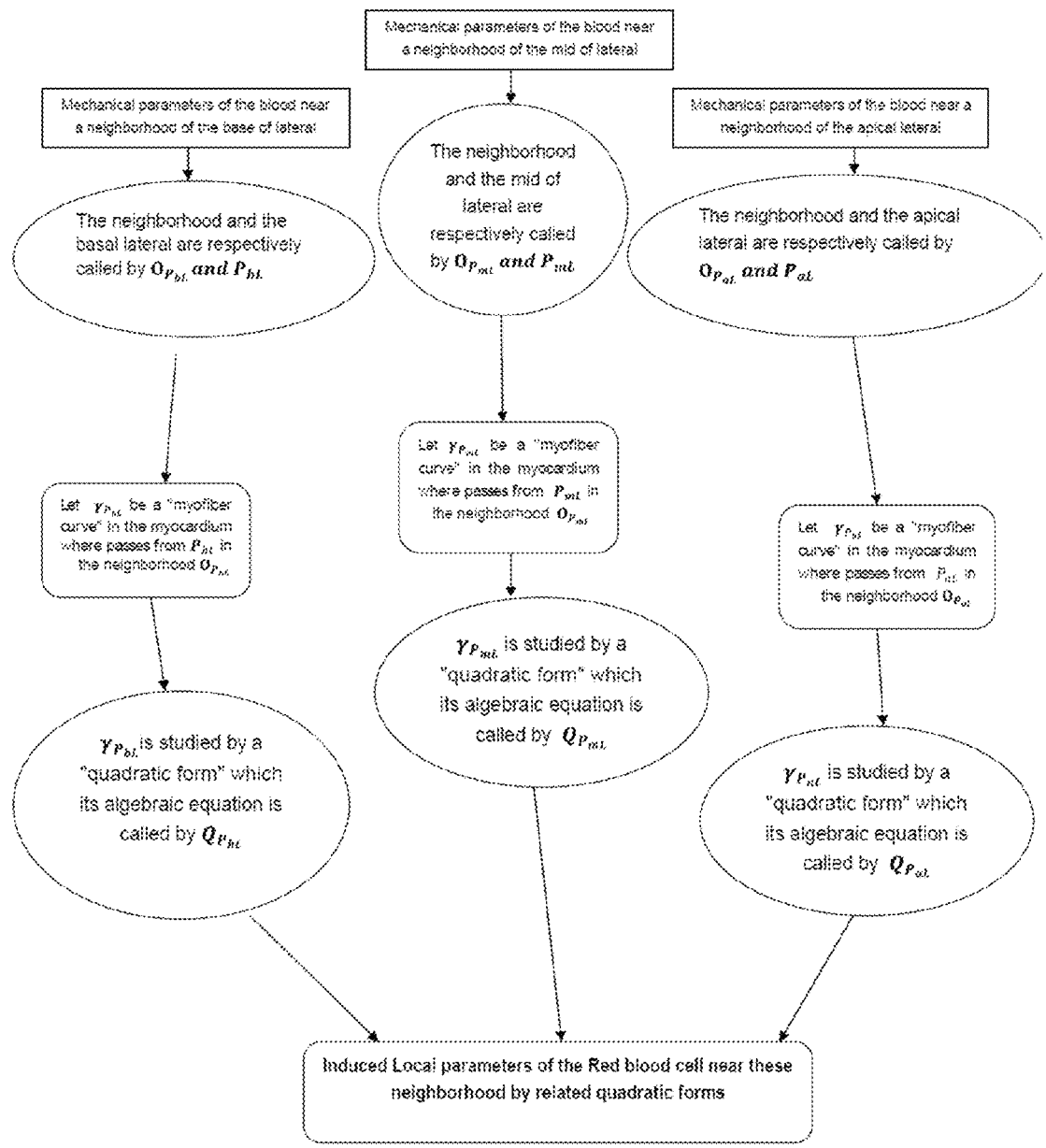
FIG. 18 shows a flowchart where states the basal, mid and apical Lateral as three echocardiography samples in the left ventricle, in their corresponded regions.

In an embodiment, as illustrated in FIG. 18, the invention provides mathematical signs of basal Lateral, mid Lateral and apical Lateral to obtain good formulizations of the induced mathematical parameters of the blood.

The invention further provides geometrical modelling of the basal, mid and apical Lateral as described below;

Let $\epsilon_{rr,P_{bL}}, \epsilon_{ll,P_{bL}}$ and $\epsilon_{cc,P_{bL}}$ be the strain components of the basal Inferior $P_{bL}$, then $$\gamma_{P_{bL}} = \{\text{each mayocardial sample } X \text{ that } \epsilon_{rr,X} \times \epsilon_{ll,X} = \epsilon_{rr,P_{bL}} \times \epsilon_{ll,P_{bL}} \text{ and } \epsilon_{rr,X} \times \epsilon_{ll,X} \times \epsilon_{cc,X} = \epsilon_{rr,P_{bL}} \times \epsilon_{ll,P_{bL}} \times \epsilon_{cc,P_{bL}}\}$$

similarly for mid and apical inferior the sets are:

$$\gamma_{P_{mL}} = \{\text{each mayocardial sample } X \text{ that } \epsilon_{rr,X} \times \epsilon_{ll,X} = \epsilon_{rr,P_{mL}} \times \epsilon_{ll,P_{mL}} \text{ and } \epsilon_{rr,X} \times \epsilon_{ll,X} \times \epsilon_{cc,X} = \epsilon_{rr,P_{mL}} \times \epsilon_{ll,P_{mL}} \times \epsilon_{cc,P_{mL}}\}$$

$$\gamma_{P_{aL}} = \{\text{each mayocardial sample } X \text{ that } \epsilon_{rr,X} \times \epsilon_{ll,X} = \epsilon_{rr,P_{aL}} \times \epsilon_{ll,P_{aL}} \text{ and } \epsilon_{rr,X} \times \epsilon_{ll,X} \times \epsilon_{cc,X} = \epsilon_{rr,P_{aL}} \times \epsilon_{ll,P_{aL}} \times \epsilon_{cc,P_{aL}}\}$$

$\gamma_{P_{bL}}, \gamma_{P_{mL}}$ and $\gamma_{P_{aL}}$ are the myofiber bands illustrated in FIG. 2. The Q's have following values $$Q_{P_{bL}} : D_{P_{bL}} = \left(\sum_{k,l} \varepsilon_{rr_{P_k,P_l}} dt\right) \cdot y_1^2 + \left(\sum_{k,l} \varepsilon_{ll_{P_k,P_l}} dt\right) \cdot y_2^2 + \left(\sum_{k,l} \varepsilon_{cc_{P_k,P_l}} dt\right) \cdot y_3^2$$

$$D_{P_{bL}} = \left(\sum_{k,l} \varepsilon_{rr_{P_k,P_l}} dt\right) \cdot y_{1,bL}^2 + \left(\sum_{k,l} \varepsilon_{ll_{P_k,P_l}} dt\right) \cdot y_{2,bL}^2 + \left(\sum_{k,l} \varepsilon_{cc_{P_k,P_l}} dt\right) \cdot y_{3,bL}^2$$

Where, $P_k$ and $P_l$ are points belonging to $\gamma_{P_{bL}} \cap O_{P_{bL}}$ and if $P_{bL} = (y_{1, bL}, y_{2, bL}, y_{3, bL})$ as Cartesian coordinate Similarly, the Cartesian coordinates for Q's for mid and apical Inferiors are as follows;

For the mid of Anterior:

$$Q_{P_{mL}} : D_{P_{bL}} = \left(\sum_{k,l} \varepsilon_{rr_{P_k,P_l}} dt\right) \cdot y_1^2 + \left(\sum_{k,l} \varepsilon_{ll_{P_k,P_l}} dt\right) \cdot y_2^2 + \left(\sum_{k,l} \varepsilon_{cc_{P_k,P_l}} dt\right) \cdot y_3^2$$

$$D_{P_{mL}} = \left(\sum_{k,l} \varepsilon_{rr_{P_k,P_l}} dt\right) \cdot y_{1,mL}^2 + \left(\sum_{k,l} \varepsilon_{ll_{P_k,P_l}} dt\right) \cdot y_{2,mL}^2 + \left(\sum_{k,l} \varepsilon_{cc_{P_k,P_l}} dt\right) \cdot y_{3,mL}^2$$

where, $P_k$ and $P_l$ are points belonging to $\gamma_{P_{mL}} \cap O_{P_{mL}}$ and if $P_{mL} = (y_{1, mL}, y_{2, mL}, y_{3, mL})$ as Cartesian coordinate:

For apical Anterior:

$$Q_{P_{aL}} : D_{P_{aL}} = \left(\sum_{k,l} \varepsilon_{rr_{P_k,P_l}} dt\right) \cdot y_1^2 + \left(\sum_{k,l} \varepsilon_{ll_{P_k,P_l}} dt\right) \cdot y_2^2 + \left(\sum_{k,l} \varepsilon_{cc_{P_k,P_l}} dt\right) \cdot y_3^2$$

$$D_{P_{aL}} = \left(\sum_{k,l} \varepsilon_{rr_{P_k,P_l}} dt\right) \cdot y_{1,aL}^2 + \left(\sum_{k,l} \varepsilon_{ll_{P_k,P_l}} dt\right) \cdot y_{2,aL}^2 + \left(\sum_{k,l} \varepsilon_{cc_{P_k,P_l}} dt\right) \cdot y_{3,aL}^2$$

where, $P_k$ and $P_l$ are points belonging to $\gamma_{P_{aL}} \cap O_{P_{aL}}$ and if $P_{aL} = (y_{1, aL}, y_{2, aL}, y_{3, aL})$ as Cartesian coordinate.

Figure 21:
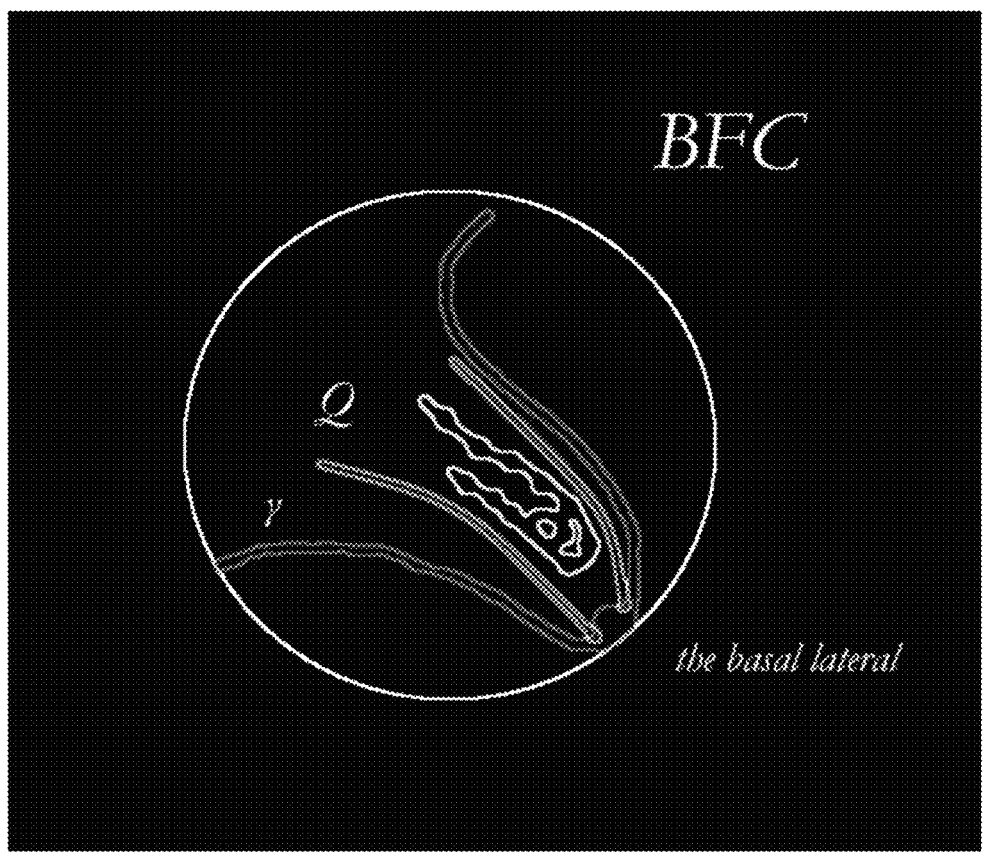
FIG. 21 shows the blood flow curve near the corresponded neighborhood of the basal Lateral in the myocardium of the left ventricle where has been rendered at Mathlab software.

In a preferred embodiment, the invention provides an analytical solution of the Navier-Stocks equations in the region $O_{P_{aL}}$ of the apical Inferior. FIG. 21 shows a rendering of these solutions in the mathlab software.

Figure 20:
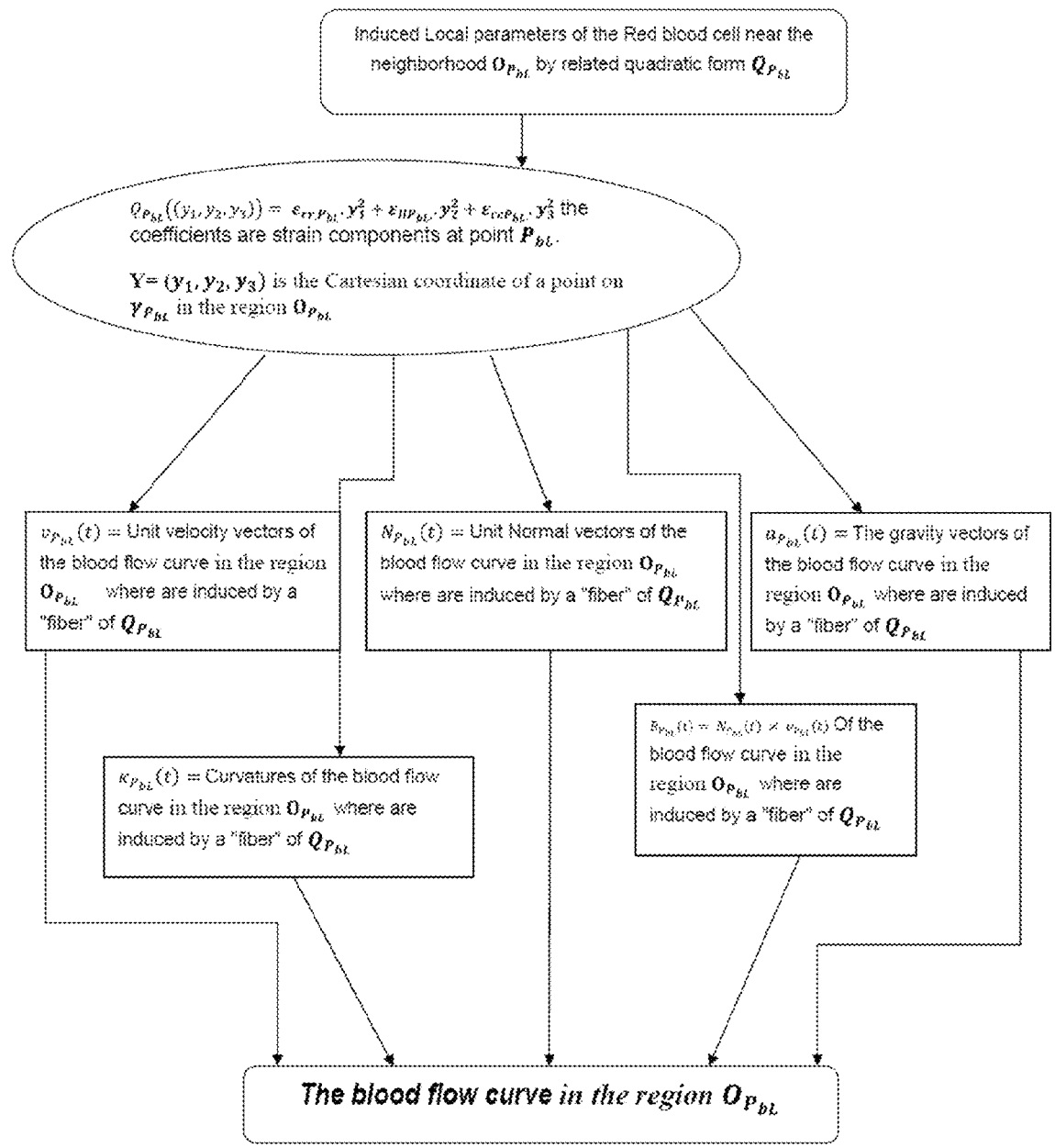
FIG. 20 shows a flowchart that models the blood flow curve near a neighborhood of the basal Lateral in the myocardium of the left ventricle.

FIG. 20, illustrates mechanical parameters of blood induced by $Q_{P_{aL}}$ in the region $O_{P_{aL}}$ related to apical Lateral. The surface parameters are as follows $$F_{P_{aL}}((y_1, y_2, y_3)) = \left(\sum_{k,l} \varepsilon'_{rr_{P_k,P_l}} dt\right) \cdot y_1^2 + \left(\sum_{k,l} \varepsilon'_{tt_{P_k,P_l}} dt\right) \cdot y_2^2 + \left(\sum_{k,l} \varepsilon'_{cc_{P_k,P_l}} dt\right) \cdot y_3^2 - D_{P_{aL}}$$

In the region $O_{P_{aL}}$, let $\phi_{1,P_{aL}}(t)$, $\phi_{2,P_{aL}}(t)$ and $\phi_{3,P_{aL}}(t)$ are parameterized forms of the projections of the surface $F_{P_{aL}}$ on xy-axis and yz-axis:

$$\varphi_{1,P_{aL}}(t) = \left(t, \left(\left(D_{P_{aL}} - \left(\sum_{k,l} \varepsilon'_{rr_{P_k,P_l}} dt\right)t^2\right) \middle/ \left(\sum_{k,l} \varepsilon'_{tt_{P_k,P_l}} dt\right)\right)^{\frac{1}{2}}\right);$$

$$\varphi_{2,P_{aL}}(t) = \left(t, \left(\left(D_{P_{aL}} - \left(\sum_{k,l} \varepsilon'_{rr_{P_k,P_l}} dt\right)t^2\right) \middle/ \left(\sum_{k,l} \varepsilon'_{cc_{P_k,P_l}} dt\right)\right)^{\frac{1}{2}}\right);$$

$$\varphi_{3,P_{aL}}(t) = \left(t, \left(\left(D_{P_{aL}} - \left(\sum_{k,l} \varepsilon'_{tt_{P_k,P_l}} dt\right)t^2\right) \middle/ \left(\sum_{k,l} \varepsilon'_{cc_{P_k,P_l}} dt\right)\right)^{\frac{1}{2}}\right)$$

Following formulae were set;

$$T_{1,P_{aL}}(t) = \phi_{1,P_{aL}}(t)' / |\phi_{1,P_{aL}}(t)'|;$$

$$S_{1,P_{aL}} = \int_{t_o}^{t} \varphi_{1,P_{aL}}(u)' du;$$

$$\kappa_{1,P_{aL}}(t) \cdot N_{1,P_{aL}}(t) = \frac{dT_{1,P_{aL}}}{ds};$$

$$\kappa_{1,P_{aL}}(t) = \left(\left(\left(D_{P_{aL}} - \left(\sum_{k,l} \varepsilon'_{rr_{P_k,P_l}} dt\right)t^2\right) \middle/ \left(\sum_{k,l} \varepsilon'_{tt_{P_k,P_l}} dt\right)\right)^{\frac{1}{2}}\right) - 0 \bigg/ S'^3_{1,P_{aL}};$$

$$a_{1,P_{aL}}(t) = S_{1,P_{aL}}'' \cdot T_{1,P_{aL}}(t) + \kappa_{1,P_{aL}}(t) \cdot N_{1,P_{aL}}(t)$$

$$T_{2,P_{aL}}(t) = \phi_{2,P_{aL}}(t)' / |\phi_{2,P_{aL}}(t)'|;$$

$$S_{2,P_{aL}} = \int_{t_o}^{t} \varphi_{2,P_{aL}}(u)' du;$$

$$\kappa_{2,P_{aL}}(t) \cdot N_{2,P_{aL}}(t) = \frac{dT_{2,P_{aL}}}{ds};$$

$$\kappa_{2,P_{aL}}(t) = \left(\left(\left(D_{P_{aL}} - \left(\sum_{k,l} \varepsilon'_{rr_{P_k,P_l}} dt\right)t^2\right) \middle/ \left(\sum_{k,l} \varepsilon'_{cc_{P_k,P_l}} dt\right)\right)^{\frac{1}{2}}\right) - 0 \bigg/ S'^3_{2,P_{aL}};$$

$$a_{2,P_{aL}}(t) = S_{2,P_{aL}}'' \cdot T_{2,P_{aL}}(t) + \kappa_{2,P_{aL}}(t) \cdot N_{2,P_{aL}}(t)$$

$$T_{3,P_{aL}}(t) = \phi_{3,P_{aL}}(t)' / |\phi_{3,P_{aL}}(t)'|;$$

$$S_{3,P_{aL}} = \int_{t_o}^{t} \varphi_{3,P_{aL}}(u)' du;$$

$$\kappa_{3,P_{aL}}(t) \cdot N_{3,P_{aL}}(t) = \frac{dT_{2,P_{aL}}}{ds};$$

$$\kappa_{3,P_{aL}}(t) = \left(\left(\left(D_{P_{aL}} - \left(\sum_{k,l} \varepsilon'_{tt_{P_k,P_l}} dt\right)t^2\right) \middle/ \left(\sum_{k,l} \varepsilon'_{tt_{P_k,P_l}} dt\right)\right)^{\frac{1}{2}}\right) - 0 \bigg/ S'^3_{3,P_{aL}};$$

$$a_{3,P_{aL}}(t) = S_{3,P_{aL}} \cdot T_{3,P_{aL}}(t) + \kappa_{3,P_{aL}}(t) \cdot N_{3,P_{aL}}(t)$$

$(x_1, x_2, x_3, t)$ is the coordinate system of the red blood cell in a neighbourhood $O_{P_{aL}}$ of the apical Lateral and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{aL}}$, $C_{2,P_{aL}}$ and $C_{3,P_{aL}}$ are the graphs of $\phi_{1,P_{aL}}(t)$, $\phi_{2,P_{aL}}(t)$ and $\phi_{3,P_{aL}}(t)$ respectively then the mechanical parameters of the red blood cells in the region $O_{P_{aL}}$ are calculated by the following formulae:

$$v_{1,P_{aL}}(t) = \int_{C_{1,P_{aL}}} T_{1,P_{aL}}(t) \otimes \delta(x_1, x_2, x_3, t) d\tau;$$

$$n_{1,P_{aL}}(t) = \int_{C_{1,P_{aL}}} N_{1,P_{aL}}(t) \otimes \delta(x_1, x_2, x_3, t) d\tau;$$

$$a^{RBC}_{1,P_{aL}}(t) = \int_{C_{1,P_{aL}}} a_{1,P_{aL}}(t) \otimes \delta(x_1, x_2, x_3, t) dt$$

$$v_{2,P_{aL}}(t) = \int_{C_{2,P_{aL}}} T_{2,P_{aL}}(t) \otimes \delta(x_1, x_2, x_3, t) d\tau;$$

$$n_{2,P_{aL}}(t) = \int_{C_{2,P_{aL}}} N_{2,P_{aL}}(t) \otimes \delta(x_1, x_2, x_3, t) d\tau;$$

$$a^{RBC}_{2,P_{aL}}(t) = \int_{C_{2,P_{aL}}} a_{2,P_{aL}}(t) \otimes \delta(x_1, x_2, x_3, t) dt$$

$$v_{3,P_{aL}}(t) = \int_{C_{3,P_{aL}}} T_{3,P_{aL}}(t) \otimes \delta(x_1, x_2, x_3, t) d\tau;$$

$$n_{3,P_{aL}}(t) = \int_{C_{3,P_{aL}}} N_{3,P_{aL}}(t) \otimes \delta(x_1, x_2, x_3, t) d\tau;$$

$$a^{RBC}_{3,P_{aL}}(t) = \int_{C_{3,P_{aL}}} a_{3,P_{aL}}(t) \otimes \delta(x_1, x_2, x_3, t) d\tau;$$

Figure 23:
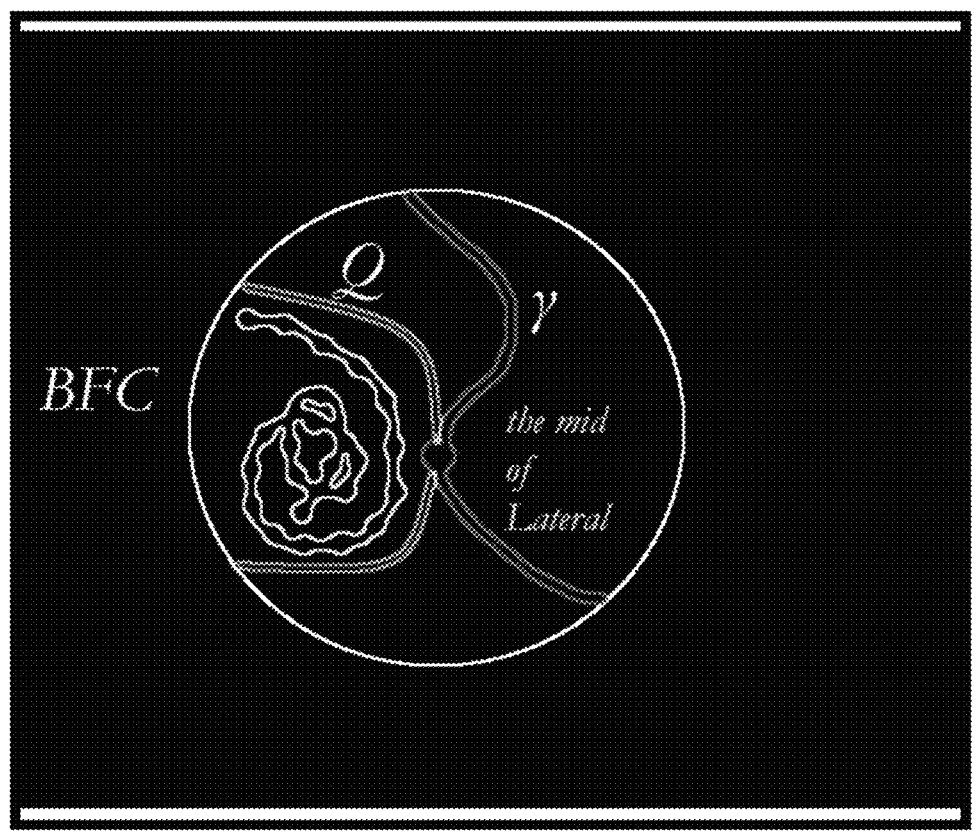
FIG. 23 shows the blood flow curve near the corresponded neighborhood of the mid Lateral in the myocardium of the left ventricle where has been rendered at Mathlab software.

In another preferred embodiment the invention provides an analytical solution of the Navier-Stocks equations in the region $O_{P_{mL}}$ of the mid Lateral. FIG. 23 shows a rendering of these solutions in the mathlab software.

Figure 22:
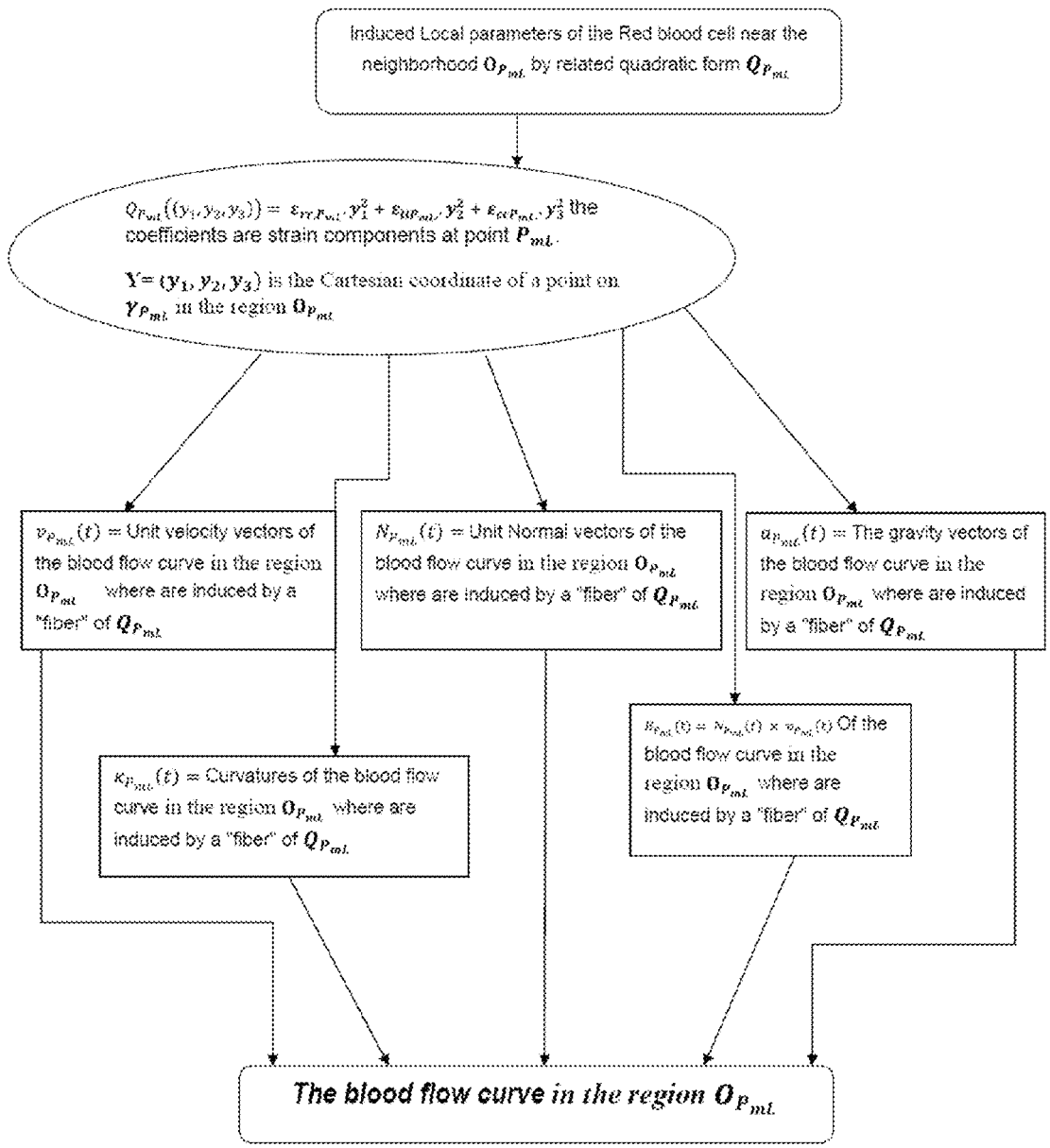
FIG. 22 shows a flowchart that models the blood flow curve near a neighborhood of the mid Lateral in the myocardium of the left ventricle.

FIG. 22 shows the mechanical parameters of blood which were induced by $Q_{P_{mL}}$ in region $O_{P_{mL}}$ related to apical inferior. The surface is;

$$F_{P_{mL}}((y_1, y_2, y_3)) = \left(\sum_{k,l} \varepsilon'_{rr_{P_k,P_l}} dt\right) \cdot y_1^2 + \left(\sum_{k,l} \varepsilon'_{tt_{P_k,P_l}} dt\right) \cdot y_2^2 + \left(\sum_{k,l} \varepsilon'_{cc_{P_k,P_l}} dt\right) \cdot y_3^2 - D_{P_{mL}}$$

In the region $O_{P_{mL}}$, let $\phi_{1,P_{mL}}(t)$, $\phi_{2,P_{mL}}(t)$ and $\phi_{3,P_{mL}}(t)$ are parameterized forms of the projections of the surface $F_{P_{mL}}$ on xy-axis, xz-axis and yz-axis:

$$\varphi_{1,P_{mL}}(t) = \left(t, \left(\left(D_{P_{mL}} - \left(\sum_{k,l} \varepsilon'_{rr_{P_k,P_l}} dt\right)t^2\right) \middle/ \left(\sum_{k,l} \varepsilon'_{tt_{P_k,P_l}} dt\right)\right)^{\frac{1}{2}}\right);$$

-continued $$\varphi_{2,P_{mL}}(t) = \left(t, \left(\left(D_{P_{mL}} - \left(\sum_{k,l}\varepsilon'_{rr_{P_k,P_l}}dt\right)t^2\right)\Big/\left(\sum_{k,l}\varepsilon'_{cc_{P_k,P_l}}dt\right)\right)^{\frac{1}{2}}\right);$$

$$\varphi_{3,P_{mL}}(t) = \left(t, \left(\left(D_{P_{mL}} - \left(\sum_{k,l}\varepsilon'_{u_{P_k,P_l}}dt\right)t^2\right)\Big/\left(\sum_{k,l}\varepsilon'_{cc_{P_k,P_l}}dt\right)\right)^{\frac{1}{2}}\right)$$

Following formulae were set;

$$T_{1,P_{mL}}(t) = \phi_{1,P_{mL}}(t)'/|\phi_{1,P_{mL}}(t)'|;$$

$$S_{1,P_{mL}} = \int_{t_o}^{t}\varphi_{1,P_{mL}}(u)'\,du;$$

$$\kappa_{1,P_{mL}}(t)\cdot N_{1,P_{mL}}(t) = \frac{dT_{1,P_{mL}}}{ds};$$

$$\kappa_{1,P_{mL}}(t) =$$
$$\left(\left(\left(D_{P_{mL}} - \left(\sum_{k,l}\varepsilon'_{rr_{P_k,P_l}}dt\right)t^2\right)\Big/\left(\sum_{k,l}\varepsilon'_{u_{P_k,P_l}}dt\right)\right)^{\frac{1}{2}}\right) - 0\Big/S'^3_{1,P_{mL}};$$

$$a_{1,P_{mL}}(t) = S_{1,P_{mL}}''\cdot T_{1,P_{mL}}(t) + \kappa_{1,P_{mL}}(t)\cdot N_{1,P_{mL}}(t)$$

$$T_{2,P_{mL}}(t) = \phi_{2,P_{mL}}(t)'/|\phi_{2,P_{mL}}(t)'|;$$

$$S_{2,P_{mL}} = \int_{t_o}^{t}\varphi_{2,P_{mL}}(u)'\,du;$$

$$\kappa_{2,P_{mL}}(t)\cdot N_{2,P_{mL}}(t) = \frac{dT_{2,P_{mL}}}{ds};$$

$$\kappa_{2,P_{mL}}(t) =$$
$$\left(\left(\left(D_{P_{mL}} - \left(\sum_{k,l}\varepsilon'_{rr_{P_k,P_l}}dt\right)t^2\right)\Big/\left(\sum_{k,l}\varepsilon'_{cc_{P_k,P_l}}dt\right)\right)^{\frac{1}{2}}\right) - 0\Big/S'^3_{2,P_{mL}};$$

$$a_{2,P_{mL}}(t) = S_{2,P_{mL}}''\cdot T_{2,P_{mL}}(t) + \kappa_{2,P_{mL}}(t)\cdot N_{2,P_{mL}}(t)$$

$$T_{3,P_{mL}}(t) = \phi_{3,P_{mL}}(t)'/|\phi_{3,P_{mL}}(t)'|;$$

$$S_{3,P_{mL}} = \int_{t_o}^{t}\varphi_{3,P_{mL}}(u)'\,du;$$

$$\kappa_{3,P_{mL}}(t)\cdot N_{3,P_{mL}}(t) = \frac{dT_{2,P_{mL}}}{ds};$$

$$\kappa_{3,P_{mL}}(t) =$$
$$\left(\left(\left(D_{P_{mL}} - \left(\sum_{k,l}\varepsilon'_{u_{P_k,P_l}}dt\right)t^2\right)\Big/\left(\sum_{k,l}\varepsilon'_{u_{P_k,P_l}}dt\right)\right)^{\frac{1}{2}}\right) - 0\Big/S'^3_{3,P_{mL}};$$

$$a_{3,P_{mL}}(t) = S_{3,P_{mL}}''\cdot T_{3,P_{mL}}(t) + \kappa_{3,P_{mL}}(t)\cdot N_{3,P_{mL}}(t)$$

$(x_1, x_2, x_3, t)$ is the coordinate system of the red blood cell in a neighbourhood $O_{P_{mL}}$ of the mid Lateral and $\delta(x_1,x_2,x_3,t) = \delta^*(x_1, t)\cdot\delta^*(x_2, t)\cdot\delta^*(x_3, t)$ where $\delta^*$ is the dirac function and $C_{1,P_{mL}}$, $C_{2,P_{mL}}$ and $C_{3,P_{mL}}$ are the graphs of $\phi_{1,P_{mL}}(t)$, $\phi_{2,P_{mL}}(t)$ and $\phi_{3,P_{mL}}(t)$ respectively then the mechanical parameters of the red blood cells in the region $O_{P_{mL}}$ are calculated by the following formulae:

$$v_{1,P_{mL}}(t) = \int_{C_{1,P_{mL}}} T_{1,P_{mL}}(t)\otimes\delta(x_1, x_2, x_3, t)\,dt;$$

$$n_{1,P_{mL}}(t) = \int_{C_{1,P_{mL}}} N_{1,P_{mL}}(t)\otimes\delta(x_1, x_2, x_3, t)\,dt;$$

$$a^{RBC}_{1,P_{mL}}(t) = \int_{C_{1,P_{mL}}} a_{1,P_{mL}}(t)\otimes\delta(x_1, x_2, x_3, t)\,dt$$

$$v_{2,P_{mL}}(t) = \int_{C_{2,P_{mL}}} T_{2,P_{mL}}(t)\otimes\delta(x_1, x_2, x_3, t)\,dt;$$

$$n_{2,P_{mL}}(t) = \int_{C_{2,P_{mL}}} N_{2,P_{mL}}(t)\otimes\delta(x_1, x_2, x_3, t)\,dt;$$

$$a^{RBC}_{2,P_{mL}}(t) = \int_{C_{2,P_{mL}}} a_{2,P_{mL}}(t)\otimes\delta(x_1, x_2, x_3, t)\,dt$$

$$v_{3,P_{mL}}(t) = \int_{C_{3,P_{mL}}} T_{3,P_{mL}}(t)\otimes\delta(x_1, x_2, x_3, t)\,dt;$$

$$n_{3,P_{mL}}(t) = \int_{C_{3,P_{mL}}} N_{3,P_{mL}}(t)\otimes\delta(x_1, x_2, x_3, t)\,dt;$$

$$a^{RBC}_{3,P_{mL}}(t) = \int_{C_{3,P_{mL}}} a_{3,P_{mL}}(t)\otimes\delta(x_1, x_2, x_3, t)\,dt;$$

Figure 25:
FIG. 25 shows the blood flow curve near the corresponded neighborhood of the apical Lateral in the myocardium of the left ventricle where has been rendered at Mathlab software.

In another preferred embodiment the invention provides an analytical solution of the Navier-Stocks equations in the region $O_{P_{bL}}$ of the basal Lateral. FIG. 25 shows a rendering of these solutions in the mathlab software.

Figure 24:
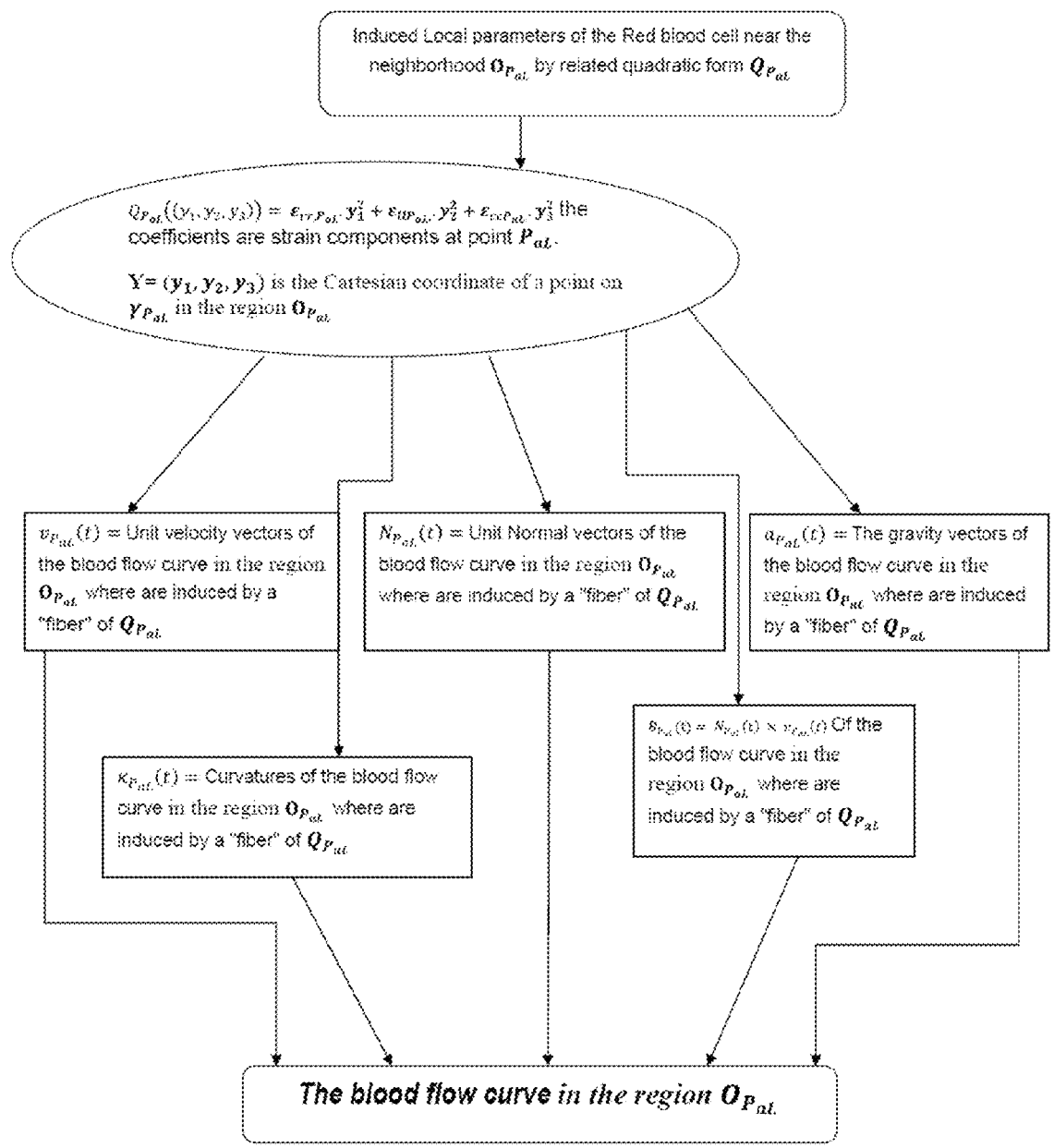
FIG. 24 shows a flowchart that models the blood flow curve near a neighborhood of the apical Lateral in the myocardium of the left ventricle.

FIG. 24 shows the mechanical parameters of blood which were induced by $Q_{P_{bL}}$ in region $O_{P_{bL}}$ related to apical inferior. The surface is;

$$F_{P_{bL}}((y_1, y_2, y_3)) = \left(\sum_{k,l}\varepsilon'_{rr_{P_k,P_l}}dt\right)\cdot y_1^2 + \left(\sum_{k,l}\varepsilon'_{u_{P_k,P_l}}dt\right)\cdot y_2^2 + \left(\sum_{k,l}\varepsilon'_{cc_{P_k,P_l}}dt\right)\cdot y_3^2 - D_{P_{bL}}$$

In the region $O_{P_{bL}}$, let $\phi_{1,P_{bL}}(t)$, $\phi_{2,P_{bL}}(t)$ and $\phi_{3,P_{bL}}(t)$ are parameterized forms of the projections of the surface $F_{P_{bL}}$ on xy-axis, xz-axis and yz-axis:

$$\varphi_{1,P_{bL}}(t) = \left(t, \left(\left(D_{P_{bL}} - \left(\sum_{k,l}\varepsilon'_{rr_{P_k,P_l}}dt\right)t^2\right)\Big/\left(\sum_{k,l}\varepsilon'_{u_{P_k,P_l}}dt\right)\right)^{\frac{1}{2}}\right);$$

$$\varphi_{2,P_{bL}}(t) = \left(t, \left(\left(D_{P_{bL}} - \left(\sum_{k,l}\varepsilon'_{rr_{P_k,P_l}}dt\right)t^2\right)\Big/\left(\sum_{k,l}\varepsilon'_{cc_{P_k,P_l}}dt\right)\right)^{\frac{1}{2}}\right);$$

$$\varphi_{3,P_{bL}}(t) = \left(t, \left(\left(D_{P_{bL}} - \left(\sum_{k,l}\varepsilon'_{rr_{P_k,P_l}}dt\right)t^2\right)\Big/\left(\sum_{k,l}\varepsilon'_{cc_{P_k,P_l}}dt\right)\right)^{\frac{1}{2}}\right)$$

Following formulae were set;

$$T_{1,P_{bL}}(t) = \phi_{1,P_{bL}}(t)'/|\phi_{1,P_{bL}}(t)'|;$$

$$S_{1,P_{bL}} = \int_{t_0}^{t} \varphi_{1,P_{bL}}(u)' du;$$

$$\kappa_{1,P_{bL}}(t) \cdot N_{1,P_{bL}}(t) = \frac{dT_{1,P_{bL}}}{ds};$$

$$\kappa_{1,P_{bL}}(t) =$$

$$\left[\left(\left(D_{P_{bL}} - \left(\sum_{k,l} \varepsilon'_{rr_{P_k,P_l}} dt\right)t^2\right) \Big/ \left(\sum_{k,l} \varepsilon'_{ll_{P_k,P_l}} dt\right)\right)^{\frac{1}{2}}\right] - 0 \Big/ S'^3_{1,P_{bL}};$$

$$a_{1,P_{bL}}(t) = S_{1,P_{bL}}'' \cdot T_{1,P_{bL}}(t) + \kappa_{1,P_{bL}}(t) \cdot N_{1,P_{bL}}(t)$$

$$T_{2,P_{bL}}(t) = \phi_{2,P_{bL}}(t)' / |\phi_{2,P_{bL}}(t)'|;$$

$$S_{2,P_{bL}} = \int_{t_0}^{t} \varphi_{2,P_{bL}}(u)' du;$$

$$\kappa_{2,P_{bL}}(t) \cdot N_{2,P_{bL}}(t) = \frac{dT_{2,P_{bL}}}{ds};$$

$$\kappa_{2,P_{bL}}(t) =$$

$$\left[\left(\left(D_{P_{bL}} - \left(\sum_{k,l} \varepsilon'_{rr_{P_k,P_l}} dt\right)t^2\right) \Big/ \left(\sum_{k,l} \varepsilon'_{cc_{P_k,P_l}} dt\right)\right)^{\frac{1}{2}}\right] - 0 \Big/ S'^3_{2,P_{bL}};$$

$$a_{2,P_{bL}}(t) = S_{2,P_{bL}}'' \cdot T_{2,P_{bL}}(t) + \kappa_{2,P_{bL}}(t) \cdot N_{2,P_{bL}}(t)$$

$$T_{3,P_{bL}}(t) = \phi_{3,P_{bL}}(t)' / |\phi_{3,P_{bL}}(t)'|;$$

$$S_{3,P_{bL}} = \int_{t_0}^{t} \varphi_{3,P_{bL}}(u)' du;$$

$$\kappa_{3,P_{bL}}(t) \cdot N_{3,P_{bL}}(t) = \frac{dT_{2,P_{bL}}}{ds};$$

$$\kappa_{3,P_{bL}}(t) =$$

$$\left[\left(\left(D_{P_{bL}} - \left(\sum_{k,l} \varepsilon'_{ll_{P_k,P_l}} dt\right)t^2\right) \Big/ \left(\sum_{k,l} \varepsilon'_{ll_{P_k,P_l}} dt\right)\right)^{\frac{1}{2}}\right] - 0 \Big/ S'^3_{3,P_{bL}};$$

$$a_{3,P_{bL}}(t) = S_{3,P_{bL}}'' \cdot T_{3,P_{bL}}(t) + \kappa_{3,P_{bL}}(t) \cdot N_{3,P_{bL}}(t)$$

$(x_1, x_2, x_3, t)$ is the coordinate system of the red blood cell in a neighbourhood $O_{P_{bL}}$ of the basal Lateral and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{bL}}$, $C_{2,P_{bL}}$ and $C_{3,P_{bL}}$ are the graphs of $\phi_{1,P_{bL}}(t)$, $\phi_{2,P_{bL}}(t)$ and $\phi_{3,P_{bL}}(t)$ respectively then the mechanical parameters of the red blood cells in the region $O_{P_{bL}}$ are calculated by the following formulae:

$$v_{1,P_{bL}}(t) = \int_{C_1,P_{bL}} T_{1,P_{bL}}(t) \otimes \delta(x_1, x_2, x_3, t) dt;$$

-continued $$n_{1,P_{bL}}(t) = \int_{C_1,P_{bL}} N_{1,P_{bL}}(t) \otimes \delta(x_1, x_2, x_3, t) dt;$$

$$a_{1,P_{bL}}^{RBC}(t) = \int_{C_1,P_{bL}} a_{1,P_{bL}}(t) \otimes \delta(x_1, x_2, x_3, t) dt$$

$$v_{2,P_{bL}}(t) = \int_{C_2,P_{bL}} T_{2,P_{bL}}(t) \otimes \delta(x_1, x_2, x_3, t) dt;$$

$$n_{2,P_{bL}}(t) = \int_{C_2,P_{bL}} N_{2,P_{bL}}(t) \otimes \delta(x_1, x_2, x_3, t) dt;$$

$$a_{2,P_{bL}}^{RBC}(t) = \int_{C_2,P_{bL}} a_{2,P_{bL}}(t) \otimes \delta(x_1, x_2, x_3, t) dt$$

$$v_{3,P_{bL}}(t) = \int_{C_3,P_{bL}} T_{3,P_{bL}}(t) \otimes \delta(x_1, x_2, x_3, t) dt;$$

$$n_{3,P_{bL}}(t) = \int_{C_3,P_{bL}} N_{3,P_{bL}}(t) \otimes \delta(x_1, x_2, x_3, t) dt;$$

$$a_{3,P_{bL}}^{RBC}(t) = \int_{C_3,P_{bL}} a_{3,P_{bL}}(t) \otimes \delta(x_1, x_2, x_3, t) dt$$

Figure 26:
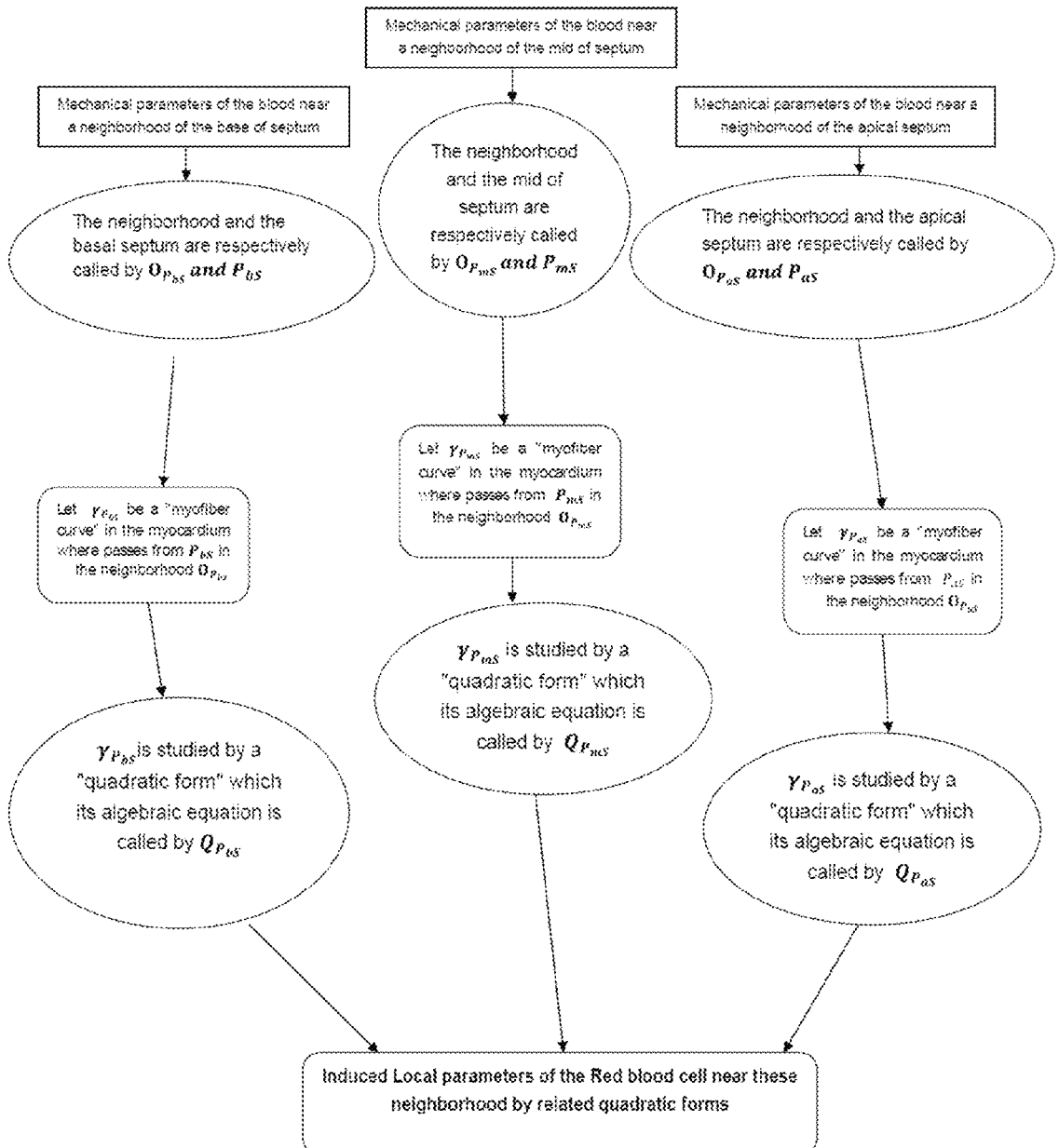
FIG. 26 shows a flowchart where states the basal, mid and apical Septum as three echocardiography samples in the left ventricle, in their corresponded regions.
Figure 27:
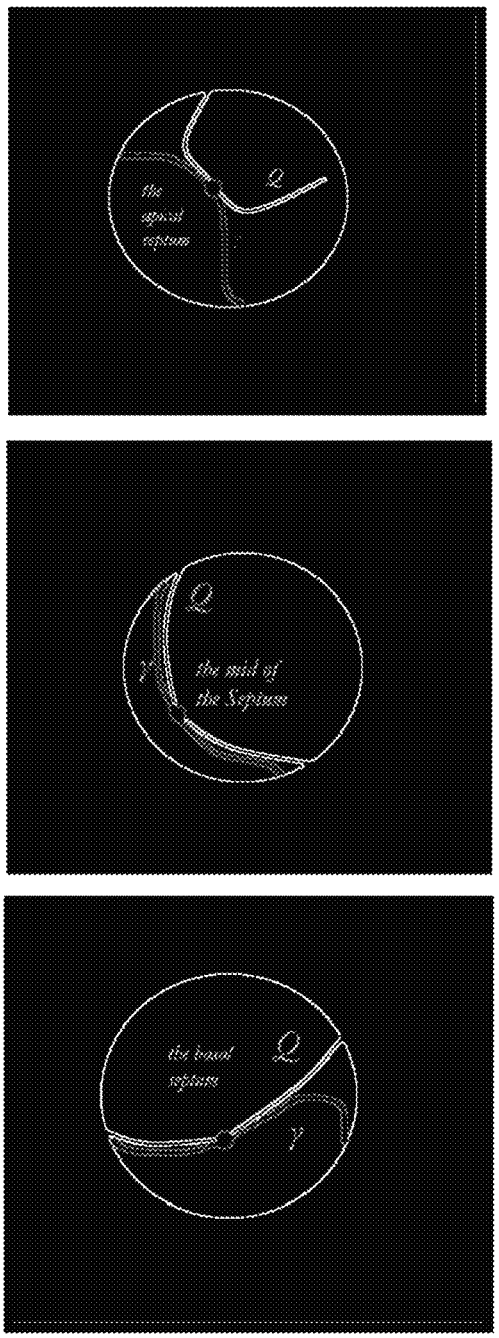
FIG. 27 shows three rendering of the basal, mid and apical septum in their corresponded regions at Mathlab software.
Figure 28:
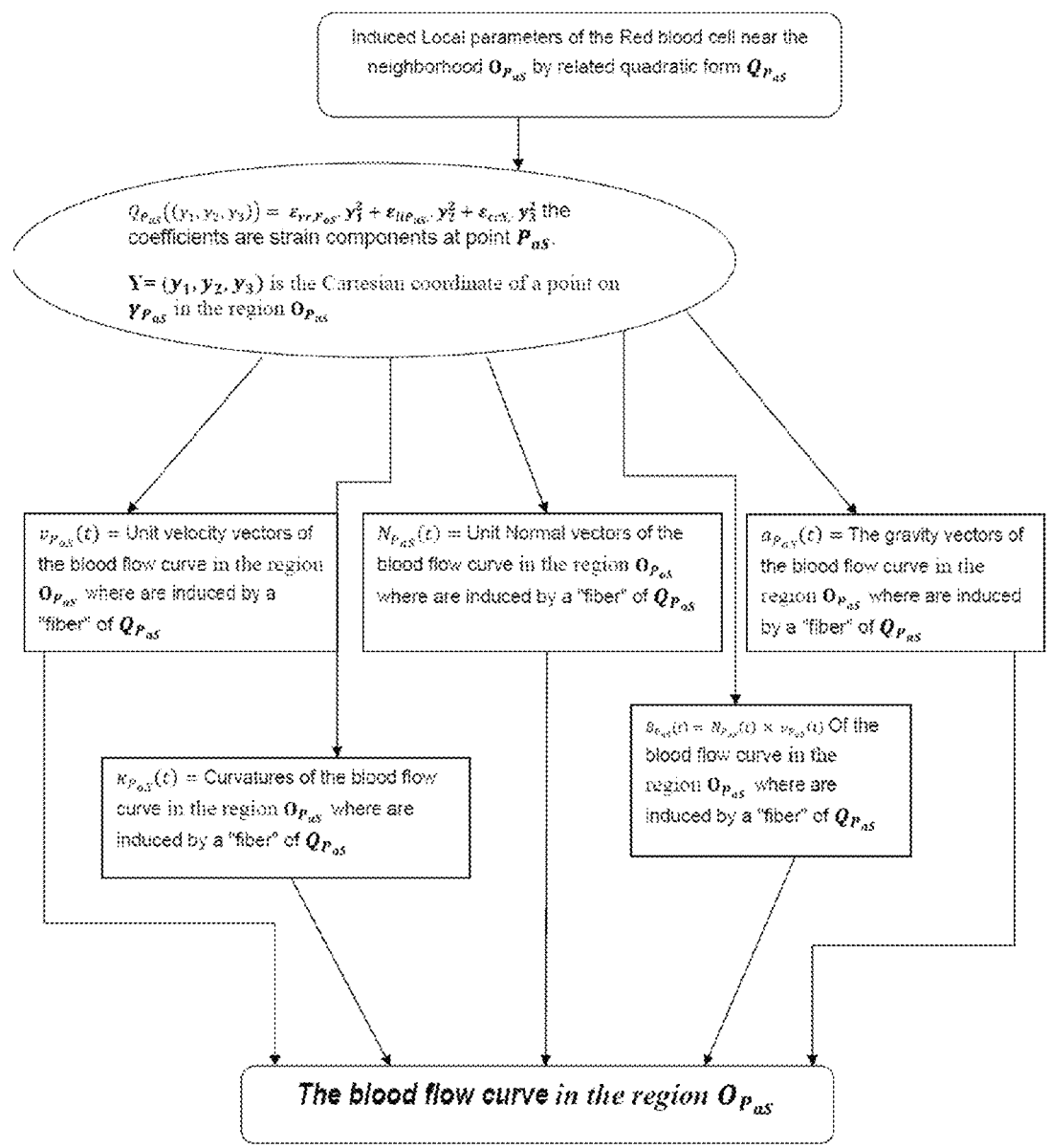
FIG. 28 shows a flowchart that models the blood flow curve near a neighborhood of the apical Septum in the myocardium of the left ventricle.

In an embodiment, as illustrated in FIG. 26, the invention provides mathematical signs of basal Septum, mid Septum and apical Septum to obtain good formulizations of the induced mathematical parameters of the blood.

The invention further provides geometrical modelling of the basal, mid and apical Septum as described below;

Let $\epsilon_{rr,P_{bS}}$, $\epsilon_{P_{bS}}$ and $\epsilon_{cc,P_{bS}}$ be the strain components of the basal Inferior $P_{bS}$, then $$\gamma_{P_{bS}} = \{\text{each mayocardial sample } X \text{ that } \epsilon_{rr,X} \times \epsilon_{ll,X} = \epsilon_{rr,P_{bS}} \times \epsilon_{ll,P_{bS}} \text{ and } \epsilon_{rr,X} \times \epsilon_{ll,X} \times \epsilon_{cc,X} = \epsilon_{rr,P_{bS}} \times \epsilon_{ll,P_{bS}} \times \epsilon_{cc,P_{bS}}\}$$

similarly for mid and apical inferior the sets are:

$$\gamma_{P_{mS}} = \{\text{each mayocardial sample } X \text{ that } \epsilon_{rr,X} \times \epsilon_{ll,X} = \epsilon_{rr,P_{mS}} \times \epsilon_{ll,P_{mS}} \text{ and } \epsilon_{rr,X} \times \epsilon_{ll,X} \times \epsilon_{cc,X} = \epsilon_{rr,P_{mS}} \times \epsilon_{ll,P_{mS}} \times \epsilon_{cc,P_{mS}}\}$$

$$\gamma_{P_{aS}} = \{\text{each mayocardial sample } X \text{ that } \epsilon_{rr,X} \times \epsilon_{ll,X} = \epsilon_{rr,P_{aS}} \times \epsilon_{ll,P_{aS}} \text{ and } \epsilon_{rr,X} \times \epsilon_{ll,X} \times \epsilon_{cc,X} = \epsilon_{rr,P_{aS}} \times \epsilon_{ll,P_{aS}} \times \epsilon_{cc,P_{aS}}\}$$

$\gamma_{P_{bS}}$, $\gamma_{P_{mS}}$ and $\gamma_{P_{aS}}$ are the myofiber bands illustrated in FIG. 2. The Q's have following values $$Q_{P_{bS}} : D_{P_{bS}} =$$

$$\left(\sum_{k,l} \varepsilon_{rr_{P_k,P_l}} dt\right) \cdot y_1^2 + \left(\sum_{k,l} \varepsilon_{ll_{P_k,P_l}} dt\right) \cdot y_2^2 + \left(\sum_{k,l} \varepsilon_{cc_{P_k,P_l}} dt\right) \cdot y_3^2$$

$$D_{P_{bS}} = \left(\sum_{k,l} \varepsilon_{rr_{P_k,P_l}} dt\right) \cdot y_{1,bS}^2 +$$

$$\left(\sum_{k,l} \varepsilon_{ll_{P_k,P_l}} dt\right) \cdot y_{2,bS}^2 + \left(\sum_{k,l} \varepsilon_{cc_{P_k,P_l}} dt\right) \cdot y_{3,bS}^2$$

Where, $P_k$ and $P_l$ are points belonging to $\gamma_{P_{bS}} \cap O_{P_{bS}}$ and if $P_{bS} = (y_{1,bS}, y_{2,bS}, y_{3,bS})$ as Cartesian coordinate Similarly, the Cartesian coordinates for Q's for mid and apical Inferiors are as follows;

For the mid of Septum:

$$Q_{P_{mS}} : D_{P_{mS}} =$$

$$\left(\sum_{k,l} \varepsilon_{rr_{P_k,P_l}} dt\right) \cdot y_1^2 + \left(\sum_{k,l} \varepsilon_{ll_{P_k,P_l}} dt\right) \cdot y_2^2 + \left(\sum_{k,l} \varepsilon_{cc_{P_k,P_l}} dt\right) \cdot y_3^2$$

-continued $$D_{P_{mS}} = \left(\sum_{k,l} \varepsilon_{rr_{P_k,P_l}} dt\right) \cdot y_{1,mS}^2 + \left(\sum_{k,l} \varepsilon_{u_{P_k,P_l}} dt\right) \cdot y_{2,mS}^2 + \left(\sum_{k,l} \varepsilon_{cc_{P_k,P_l}} dt\right) \cdot y_{3,mS}^2$$

where, $P_k$ and $P_l$ are points belonging to $\gamma_{P_{mS}} \cap O_{P_{mS}}$ and if $P_{mS} = (y_{1,mS}, y_{2,mS}, y_{3,mS})$ as Cartesian coordinate.

For apical Anterior:

$$Q_{P_{aS}} : D_{P_{aS}} = \left(\sum_{k,l} \varepsilon_{rr_{P_k,P_l}} dt\right) \cdot y_1^2 + \left(\sum_{k,l} \varepsilon_{u_{P_k,P_l}} dt\right) \cdot y_2^2 + \left(\sum_{k,l} \varepsilon_{cc_{P_k,P_l}} dt\right) \cdot y_3^2$$

$$D_{P_{aS}} = \left(\sum_{k,l} \varepsilon_{rr_{P_k,P_l}} dt\right) \cdot y_{1,aS}^2 + \left(\sum_{k,l} \varepsilon_{u_{P_k,P_l}} dt\right) \cdot y_{2,aS}^2 + \left(\sum_{k,l} \varepsilon_{cc_{P_k,P_l}} dt\right) \cdot y_{3,aS}^2$$

where, $P_k$ and $P_l$ are points belonging to $\gamma_{P_{aS}} \cap O_{P_{aS}}$ and if $P_{aS} = (y_{1,aS}, y_{2,aS}, y_{3,aS})$ as Cartesian coordinate.

Figure 30:
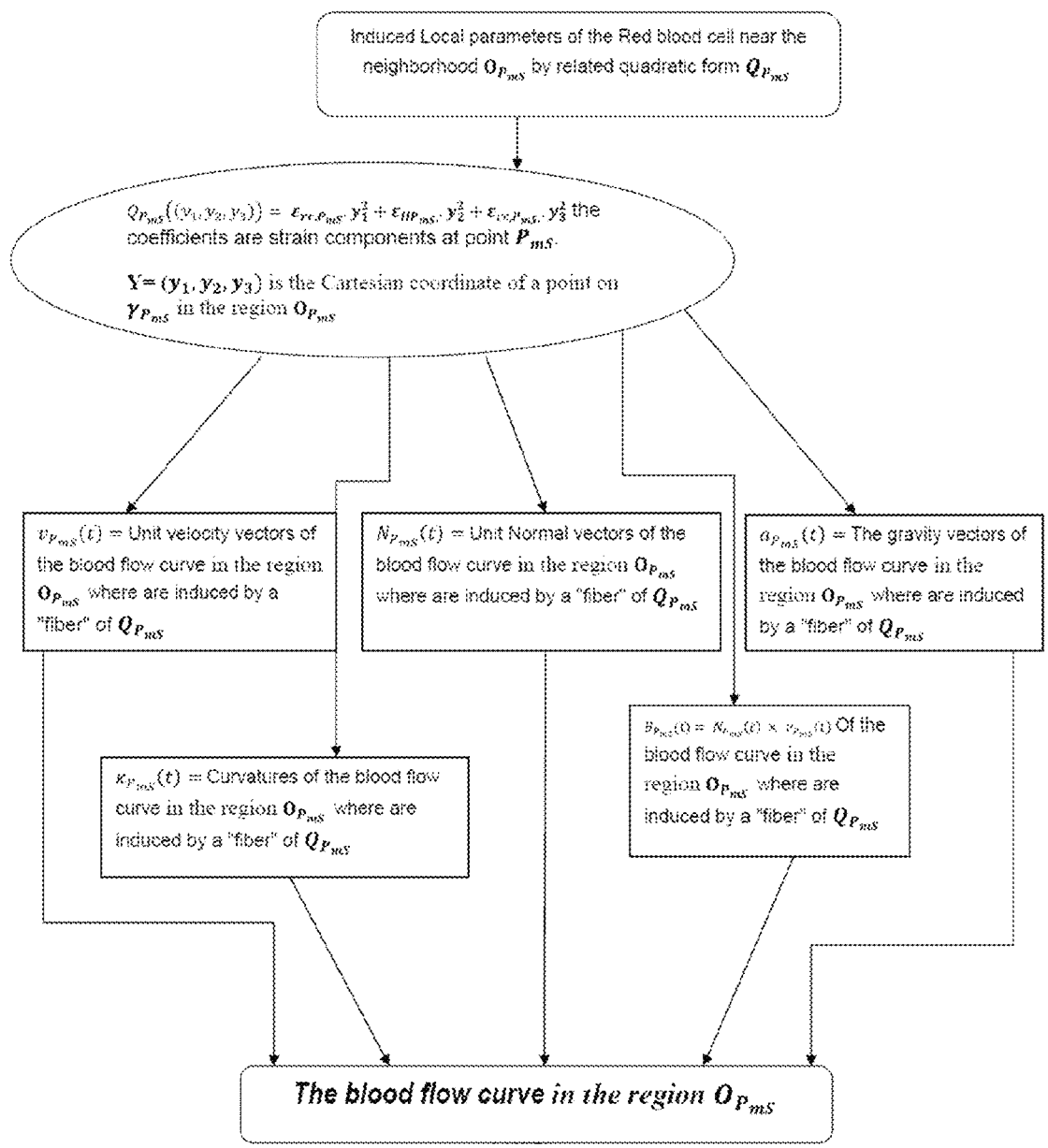
FIG. 30 shows a flowchart that models the blood flow curve near a neighborhood of the mid Septum in the myocardium of the left ventricle.

In a preferred embodiment, the invention provides an analytical solution of the Navier-Stocks equations in the region $O_{P_{aS}}$ of the apical Septum. FIG. 30 shows a rendering of these solutions in the mathlab software.

Figure 29:
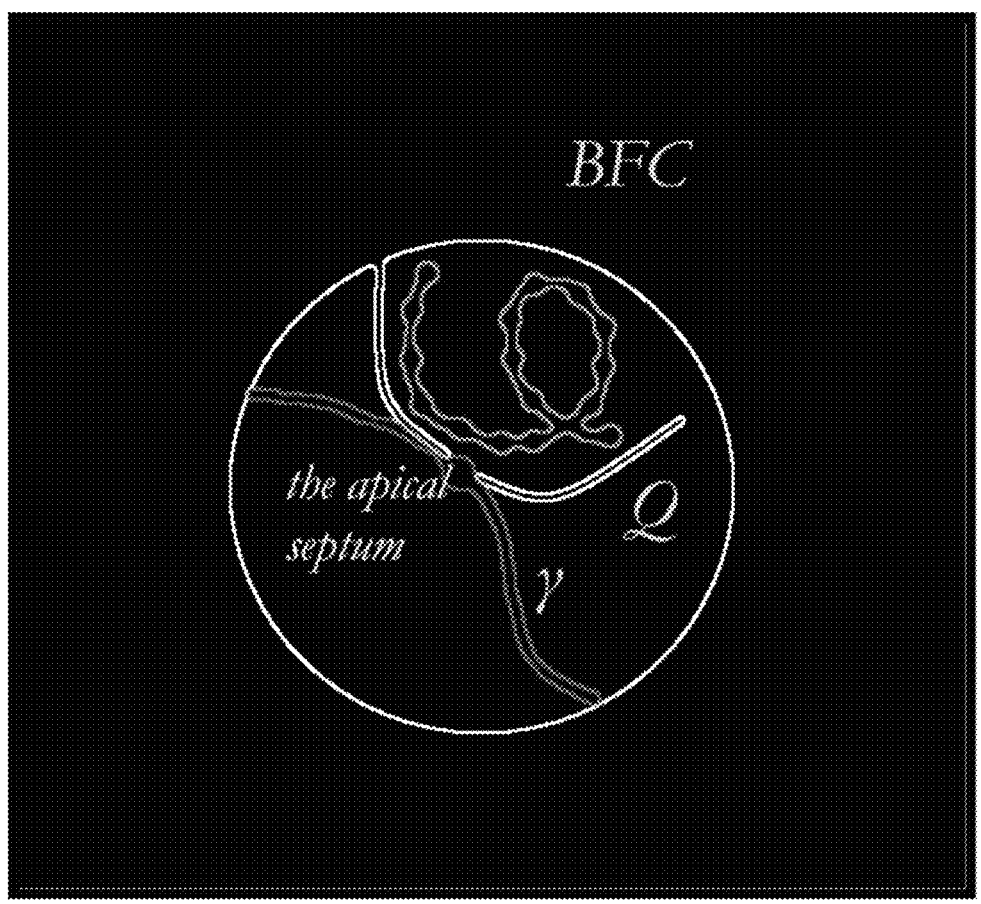
FIG. 29 shows the blood flow curve near the corresponded neighborhood of the apical Septum in the myocardium of the left ventricle where has been rendered at Mathlab software.

FIG. 29, illustrates mechanical parameters of blood induced by $Q_{P_{aS}}$ in the region $O_{P_{aS}}$ related to apical Lateral. The surface parameters are as follows $$F_{P_{aS}}((y_1, y_2, y_3)) = \left(\sum_{k,l} \varepsilon'_{rr_{P_k,P_l}} dt\right) \cdot y_1^2 + \left(\sum_{k,l} \varepsilon'_{u_{P_k,P_l}} dt\right) \cdot y_2^2 + \left(\sum_{k,l} \varepsilon'_{cc_{P_k,P_l}} dt\right) \cdot y_3^2 - D_{P_{aS}}$$

In the region $O_{P_{aS}}$, let $\phi_{1,P_{aS}}(t)$, $\phi_{2,P_{aS}}(t)$ and $\phi_{3,P_{aS}}(t)$ are parameterized forms of the projections of the surface $F_{P_{aS}}$ on xy-axis, xz-axis and yz-axis:

$$\varphi_{1,P_{aS}}(t) = \left(t, \left(\left(D_{P_{aS}} - \left(\sum_{k,l} \varepsilon'_{rr_{P_k,P_l}} dt\right)t^2\right) \middle/ \left(\sum_{k,l} \varepsilon'_{u_{P_k,P_l}} dt\right)\right)^{\frac{1}{2}}\right);$$

$$\varphi_{2,P_{aS}}(t) = \left(t, \left(\left(D_{P_{aS}} - \left(\sum_{k,l} \varepsilon'_{rr_{P_k,P_l}} dt\right)t^2\right) \middle/ \left(\sum_{k,l} \varepsilon'_{cc_{P_k,P_l}} dt\right)\right)^{\frac{1}{2}}\right);$$

$$\varphi_{3,P_{aS}}(t) = \left(t, \left(\left(D_{P_{aS}} - \left(\sum_{k,l} \varepsilon'_{u_{P_k,P_l}} dt\right)t^2\right) \middle/ \left(\sum_{k,l} \varepsilon'_{cc_{P_k,P_l}} dt\right)\right)^{\frac{1}{2}}\right)$$

Following formulae were set;

$$T_{1,P_{aS}}(t) = \phi_{1,P_{aS}}(t)'/|\phi_{1,P_{aS}}(t)'|;$$

$$S_{1,P_{aS}} = \int_{t_o}^{t} \varphi_{1,P_{aS}}(u)' \, du;$$

$$\kappa_{1,P_{aS}}(t) \cdot N_{1,P_{aS}}(t) = \frac{dT_{1,P_{aS}}}{ds};$$

$$\kappa_{1,P_{aS}}(t) = \left(\left(\left(D_{P_{aS}} - \left(\sum_{k,l} \varepsilon'_{rr_{P_k,P_l}} dt\right)t^2\right) \middle/ \left(\sum_{k,l} \varepsilon'_{u_{P_k,P_l}} dt\right)\right)^{\frac{1}{2}}\right) - 0 / S_{1,P_{aS}}^{'3};$$

$$a_{1,P_{aS}}(t) = S_{1,P_{aS}}'' \cdot T_{1,P_{aS}}(t) + \kappa_{1,P_{aS}}(t) \cdot N_{1,P_{aS}}(t)$$

$$T_{2,P_{aS}}(t) = \phi_{2,P_{aS}}(t)'/|\phi_{2,P_{aS}}(t)'|;$$

$$S_{2,P_{aS}} = \int_{t_o}^{t} \varphi_{2,P_{aS}}(u)' \, du;$$

$$\kappa_{2,P_{aS}}(t) \cdot N_{2,P_{aS}}(t) = \frac{dT_{2,P_{aS}}}{ds};$$

$$\kappa_{2,P_{aS}}(t) = \left(\left(\left(D_{P_{aS}} - \left(\sum_{k,l} \varepsilon'_{rr_{P_k,P_l}} dt\right)t^2\right) \middle/ \left(\sum_{k,l} \varepsilon'_{cc_{P_k,P_l}} dt\right)\right)^{\frac{1}{2}}\right) - 0 / S_{2,P_{aS}}^{'3};$$

$$a_{2,P_{aS}}(t) = S_{2,P_{aS}}'' \cdot T_{2,P_{aS}}(t) + \kappa_{2,P_{aS}}(t) \cdot N_{2,P_{aS}}(t)$$

$$T_{3,P_{aS}}(t) = \phi_{3,P_{aS}}(t)'/|\phi_{3,P_{aS}}(t)'|;$$

$$S_{3,P_{aS}} = \int_{t_o}^{t} \varphi_{3,P_{aS}}(u)' \, du;$$

$$\kappa_{3,P_{aS}}(t) \cdot N_{3,P_{aS}}(t) = \frac{dT_{2,P_{aS}}}{ds};$$

$$\kappa_{3,P_{aS}}(t) = \left(\left(\left(D_{P_{aS}} - \left(\sum_{k,l} \varepsilon'_{u_{P_k,P_l}} dt\right)t^2\right) \middle/ \left(\sum_{k,l} \varepsilon'_{u_{P_k,P_l}} dt\right)\right)^{\frac{1}{2}}\right) - 0 / S_{3,P_{aS}}^{'3};$$

$$a_{3,P_{aS}}(t) = S_{3,P_{aS}}' \cdot T_{3,P_{aS}}(t) + \kappa_{3,P_{aS}}(t) \cdot N_{3,P_{aS}}(t)$$

$(x_1, x_2, x_3, t)$ is the coordinate system of the red blood cell in a neighbourhood $O_{P_{aS}}$ of the apical Septum and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{aS}}$, $C_{2,P_{aS}}$ and $C_{3,P_{aS}}$ are the graphs of $\phi_{1,P_{aS}}(t)$, $\phi_{2,P_{aS}}(t)$ and $\phi_{3,P_{aS}}(t)$ respectively then the mechanical parameters of the red blood cells in the region $O_{P_{aS}}$ are calculated by the following formulae:

$$v_{1,P_{aS}}(t) = \int_{C_{1,P_{aS}}} T_{1,P_{aS}}(t) \otimes \delta(x_1, x_2, x_3, t) \, d\tau;$$

$$n_{1,P_{aS}}(t) = \int_{C_{1,P_{aS}}} N_{1,P_{aS}}(t) \otimes \delta(x_1, x_2, x_3, t) \, d\tau;$$

$$a_{1,P_{aS}}^{RBC}(t) = \int_{C_{1,P_{aS}}} a_{1,P_{aS}}(t) \otimes \delta(x_1, x_2, x_3, t) \, d\tau$$

-continued $$v_{2,P_{aS}}(t) = \int_{C_{2,P_{aS}}} T_{2,P_{aS}}(t) \otimes \delta(x_1, x_2, x_3, t) \, dt;$$

$$n_{2,P_{aS}}(t) = \int_{C_{2,P_{aS}}} N_{2,P_{aS}}(t) \otimes \delta(x_1, x_2, x_3, t) \, dt;$$

$$a_{2,P_{aS}}^{RBC}(t) = \int_{C_{2,P_{aS}}} a_{2,P_{aS}}(t) \otimes \delta(x_1, x_2, x_3, t) \, dt$$

$$v_{3,P_{aS}}(t) = \int_{C_{3,P_{aS}}} T_{3,P_{aS}}(t) \otimes \delta(x_1, x_2, x_3, t) \, dt;$$

$$n_{3,P_{aS}}(t) = \int_{C_{3,P_{aS}}} N_{3,P_{aS}}(t) \otimes \delta(x_1, x_2, x_3, t) \, dt;$$

$$a_{3,P_{aS}}^{RBC}(t) = \int_{C_{3,P_{aS}}} a_{3,P_{aS}}(t) \otimes \delta(x_1, x_2, x_3, t) \, dt$$

Figure 32:
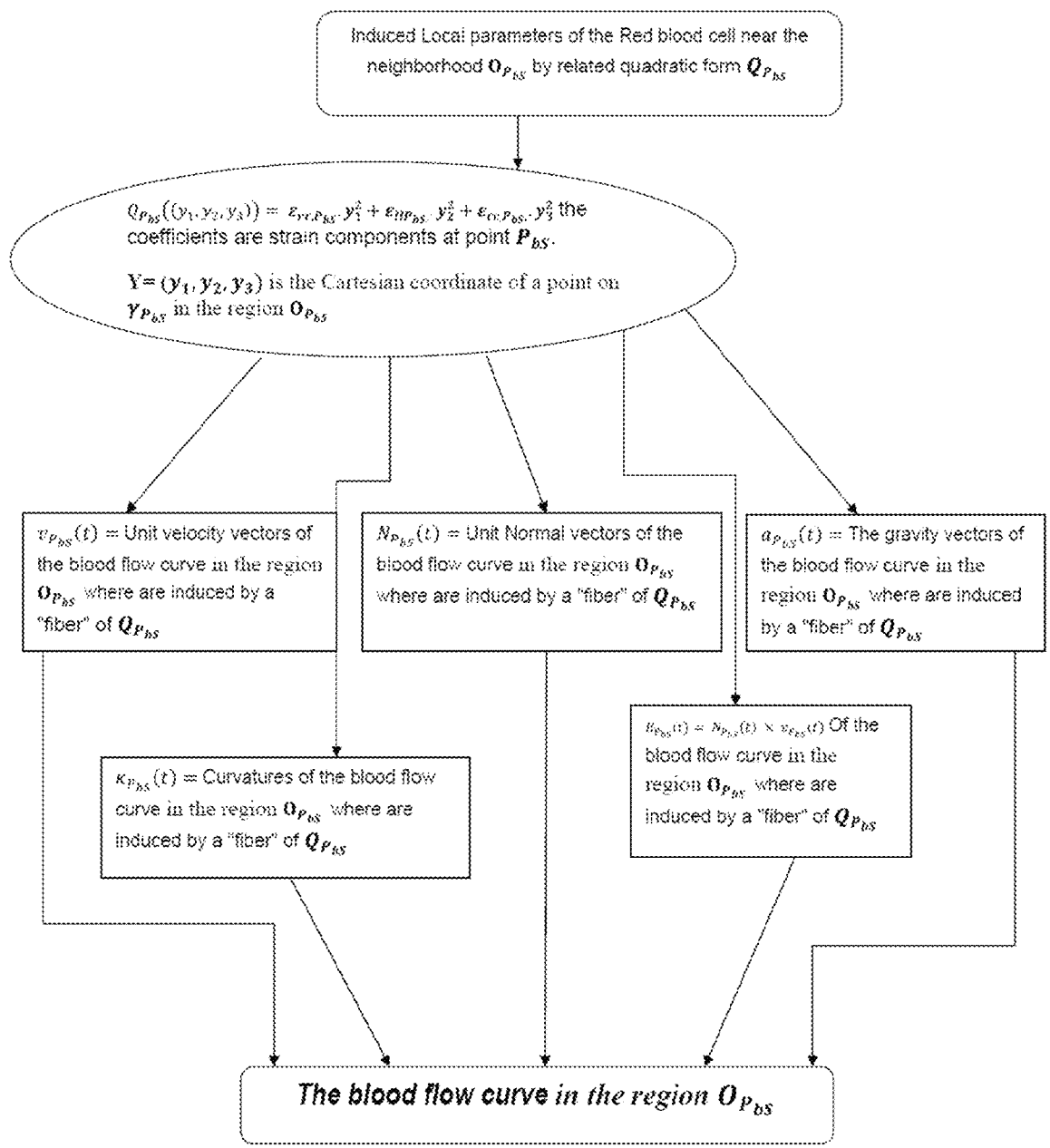
FIG. 32 shows a flowchart that models the blood flow curve near a neighborhood of the basal Septum in the myocardium of the left ventricle.

In a preferred embodiment, the invention provides an analytical solution of the Navier-Stocks equations in the region $O_{P_{mS}}$ of the mid Septum. FIG. 32 shows a rendering of these solutions in the mathlab software.

Figure 31:
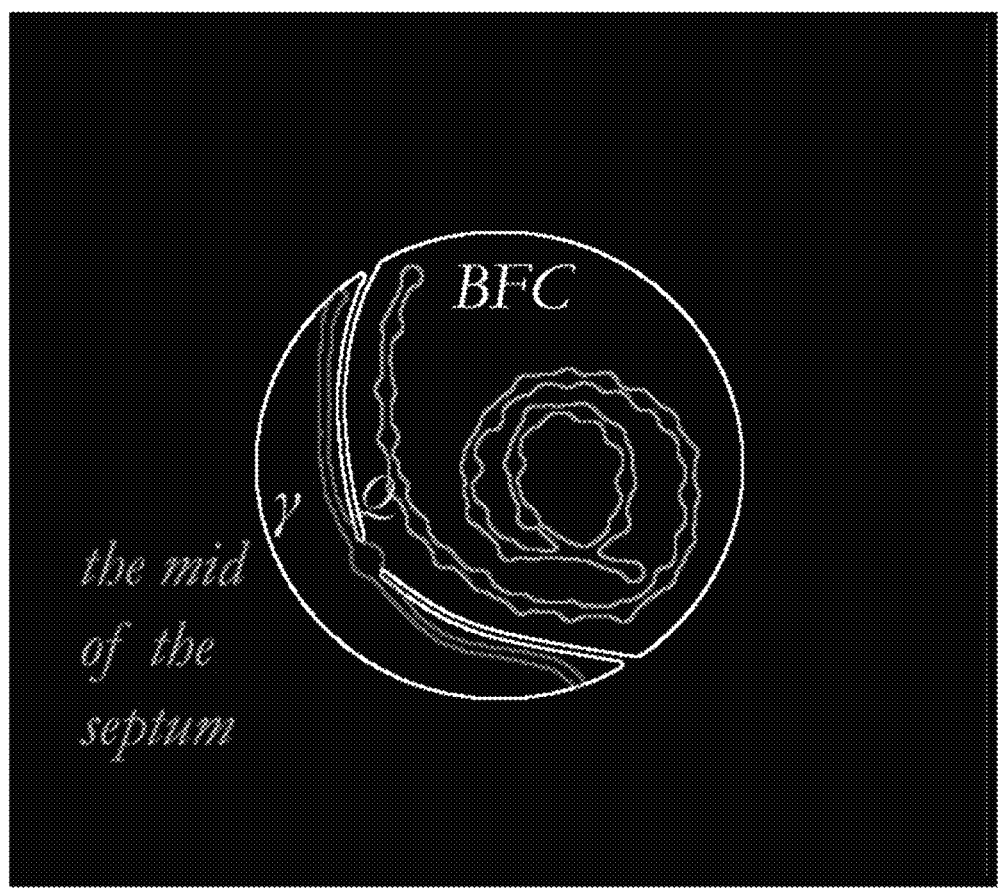
FIG. 31 shows the blood flow curve near the corresponded neighborhood of the mid Septum in the myocardium of the left ventricle where has been rendered at Mathlab software.

FIG. 31, illustrates mechanical parameters of blood induced by $Q_{P_{mS}}$ in the region $O_{P_{mS}}$ related to mid Lateral. The surface parameters are as follows $$F_{P_{mS}}((y_1, y_2, y_3)) = \left(\sum_{k,l} \varepsilon'_{rr_{P_k,P_l}} \, dt\right) \cdot y_1^2 + \left(\sum_{k,l} \varepsilon'_{u_{P_k,P_l}} \, dt\right) \cdot y_2^2 + \left(\sum_{k,l} \varepsilon'_{cc_{P_k,P_l}} \, dt\right) \cdot y_3^2 - D_{P_{mS}}$$

In the region $O_{P_{mS}}$, let $\phi_{1,P_{mS}}(t)$, $\phi_{2,P_{mS}}(t)$ and $\phi_{3,P_{mS}}(t)$ are parameterized forms of the projections of the surface $F_{P_{mS}}$ on xy-axis, xz-axis and yz-axis:

$$\varphi_{1,P_{mS}}(t) = \left(t, \left(\left(D_{P_{mS}} - \left(\sum_{k,l} \varepsilon'_{rr_{P_k,P_l}} \, dt\right)t^2\right) \middle/ \left(\sum_{k,l} \varepsilon'_{u_{P_k,P_l}} \, dt\right)\right)^{\frac{1}{2}}\right);$$

$$\varphi_{2,P_{mS}}(t) = \left(t, \left(\left(D_{P_{mS}} - \left(\sum_{k,l} \varepsilon'_{rr_{P_k,P_l}} \, dt\right)t^2\right) \middle/ \left(\sum_{k,l} \varepsilon'_{cc_{P_k,P_l}} \, dt\right)\right)^{\frac{1}{2}}\right);$$

$$\varphi_{3,P_{mS}}(t) = \left(t, \left(\left(D_{P_{mS}} - \left(\sum_{k,l} \varepsilon'_{u_{P_k,P_l}} \, dt\right)t^2\right) \middle/ \left(\sum_{k,l} \varepsilon'_{cc_{P_k,P_l}} \, dt\right)\right)^{\frac{1}{2}}\right)$$

Following formulae were set;

$$T_{1,P_{mS}}(t) = \phi_{1,P_{mS}}(t)'/|\phi_{1,P_{mS}}(t)'|;$$

$$S_{1,P_{mS}} = \int_{t_o}^{t} \varphi_{1,P_{mS}}(u)' \, du;$$

$$\kappa_{1,P_{mS}}(t) \cdot N_{1,P_{mS}}(t) = \frac{dT_{1,P_{mS}}}{ds};$$

$$\kappa_{2,P_{mS}}(t) = \left(\left(\left(D_{P_{mS}} - \left(\sum_{k,l} \varepsilon'_{rr_{P_k,P_l}} \, dt\right)t^2\right) \middle/ \left(\sum_{k,l} \varepsilon'_{u_{P_k,P_l}} \, dt\right)\right)^{\frac{1}{2}} - 0\right) \middle/ S'^3_{1,P_{mS}};$$

$$a_{1,P_{mS}}(t) = S_{1,P_{mS}}'' \cdot T_{1,P_{mS}}(t) + \kappa_{1,P_{mS}}(t) \cdot N_{1,P_{mS}}(t)$$

$$T_{2,P_{mS}}(t) = \phi_{2,P_{mS}}(t)'/|\phi_{1,P_{mS}}(t)'|;$$

$$S_{2,P_{mS}} = \int_{t_o}^{t} \varphi_{2,P_{mS}}(u)' \, du;$$

$$\kappa_{2,P_{mS}}(t) \cdot N_{2,P_{mS}}(t) = \frac{dT_{2,P_{mS}}}{ds};$$

$$\kappa_{2,P_{mS}}(t) = \left(\left(\left(D_{P_{mS}} - \left(\sum_{k,l} \varepsilon'_{rr_{P_k,P_l}} \, dt\right)t^2\right) \middle/ \left(\sum_{k,l} \varepsilon'_{cc_{P_k,P_l}} \, dt\right)\right)^{\frac{1}{2}} - 0\right) \middle/ S'^3_{2,P_{mS}};$$

$$a_{2,P_{mS}}(t) = S_{2,P_{mS}}'' \cdot T_{2,P_{mS}}(t) + \kappa_{2,P_{mS}}(t) \cdot N_{2,P_{mS}}(t)$$

$$T_{3,P_{mS}}(t) = \phi_{3,P_{mS}}(t)'/|\phi_{3,P_{mS}}(t)'|;$$

$$S_{3,P_{mS}} = \int_{t_o}^{t} \varphi_{3,P_{mS}}(u)' \, du;$$

$$\kappa_{3,P_{mS}}(t) \cdot N_{3,P_{mS}}(t) = \frac{dT_{2,P_{mS}}}{ds};$$

$$\kappa_{3,P_{mS}}(t) = \left(\left(\left(D_{P_{mS}} - \left(\sum_{k,l} \varepsilon'_{u_{P_k,P_l}} \, dt\right)t^2\right) \middle/ \left(\sum_{k,l} \varepsilon'_{u_{P_k,P_l}} \, dt\right)\right)^{\frac{1}{2}} - 0\right) \middle/ S'^3_{3,P_{mS}};$$

$$a_{3,P_{mS}}(t) = S_{3,P_{mS}}' \cdot T_{3,P_{mS}}(t) + \kappa_{3,P_{mS}}(t) \cdot N_{3,P_{mS}}(t)$$

Following formulae were set;

$$T_{1,P_{mS}}(t) = \phi_{1,P_{mS}}(t)'/|\phi_{3,P_{mS}}(t)'|;$$

$$S_{1,P_{mS}} = \int_{t_o}^{t} \varphi_{1,P_{mS}}(u)' \, du;$$

$$\kappa_{1,P_{mS}}(t) \cdot N_{1,P_{mS}}(t) = \frac{dT_{1,P_{mS}}}{ds};$$

$$\kappa_{1,P_{mS}}(t) = \left(\left(\left(D_{P_{mS}} - \left(\sum_{k,l} \varepsilon'_{rr_{P_k,P_l}} \, dt\right)t^2\right) \middle/ \left(\sum_{k,l} \varepsilon'_{u_{P_k,P_l}} \, dt\right)\right)^{\frac{1}{2}} - 0\right) \middle/ S'^3_{1,P_{mS}};$$

$$a_{1,P_{mS}}(t) = S_{1,P_{mS}}'' \cdot T_{1,P_{mS}}(t) + \kappa_{1,P_{mS}}(t) \cdot N_{1,P_{mS}}(t)$$

$$T_{2,P_{mS}}(t) = \phi_{2,P_{mS}}(t)'/|\phi_{2,P_{mS}}(t)'|;$$

$$S_{2,P_{mS}} = \int_{t_o}^{t} \varphi_{2,P_{mS}}(u)' \, du;$$

$$\kappa_{2,P_{mS}}(t) \cdot N_{2,P_{mS}}(t) = \frac{dT_{2,P_{mS}}}{ds};$$

$$\kappa_{2,P_{mS}}(t) =$$
$$\left(\left(\left(D_{P_{mS}} - \left(\sum_{k,l} \varepsilon'_{rr_{P_k},P_l} dt\right)t^2\right) \bigg/ \left(\sum_{k,l} \varepsilon'_{cc_{P_k},P_l} dt\right)\right)^{\frac{1}{2}}\right) - 0 \bigg/ S'^{3}_{2,P_{mS}};$$

$$a_{2,P_{mS}}(t) = S_{2,P_{mS}}'' \cdot T_{2,P_{mS}}(t) + \kappa_{2,P_{mS}}(t) \cdot N_{2,P_{mS}}(t)$$

$$T_{3,P_{mS}}(t) = \phi_{3,P_{mS}}(t)' / |\phi_{3,P_{mS}}(t)'|;$$

$$S_{3,P_{mS}} = \int_{t_o}^{t} \varphi_{3,P_{mS}}(u)' \, du;$$

$$\kappa_{3,P_{mS}}(t) \cdot N_{3,P_{mS}}(t) = \frac{dT_{2,P_{mS}}}{ds};$$

$$\kappa_{3,P_{mS}}(t) =$$
$$\left(\left(\left(D_{P_{mS}} - \left(\sum_{k,l} \varepsilon'_{u_{P_k},P_l} dt\right)t^2\right) \bigg/ \left(\sum_{k,l} \varepsilon'_{u_{P_k},P_l} dt\right)\right)^{\frac{1}{2}}\right) - 0 \bigg/ S'^{3}_{3,P_{mS}};$$

$$a_{3,P_{mS}}(t) = S_{3,P_{mS}} \cdot T_{3,P_{mS}}(t) + \kappa_{3,P_{mS}}(t) \cdot N_{3,P_{mS}}(t)$$

$(x_1, x_2, x_3, t)$ is the coordinate system of the red blood cell in a neighbourhood $O_{P_{mS}}$ of the apical Septum and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{mS}}$, $C_{2,P_{mS}}$ and $C_{3,P_{mS}}$ are the graphs of $\phi_{1,P_{mS}}(t)$, $\phi_{2,P_{mS}}(t)$ and $\phi_{3,P_{mS}}(t)$ respectively then the mechanical parameters of the red blood cells in the region $O_{P_{mS}}$ are calculated by the following formulae:

$$v_{1,P_{mS}}(t) = \int_{C_{1,P_{mS}}} T_{1,P_{mS}}(t) \otimes \delta(x_1, x_2, x_3, t) \, dt;$$

$$n_{1,P_{mS}}(t) = \int_{C_{1,P_{mS}}} N_{1,P_{mS}}(t) \otimes \delta(x_1, x_2, x_3, t) \, dt;$$

$$a^{RBC}_{1,P_{mS}}(t) = \int_{C_{1,P_{mS}}} a_{1,P_{mS}}(t) \otimes \delta(x_1, x_2, x_3, t) \, dt$$

$$v_{2,P_{mS}}(t) = \int_{C_{2,P_{mS}}} T_{2,P_{mS}}(t) \otimes \delta(x_1, x_2, x_3, t) \, dt;$$

$$n_{2,P_{mS}}(t) = \int_{C_{2,P_{mS}}} N_{2,P_{mS}}(t) \otimes \delta(x_1, x_2, x_3, t) \, dt;$$

$$a^{RBC}_{2,P_{mS}}(t) = \int_{C_{2,P_{mS}}} a_{2,P_{mS}}(t) \otimes \delta(x_1, x_2, x_3, t) \, dt$$

$$v_{3,P_{mS}}(t) = \int_{C_{3,P_{mS}}} T_{3,P_{mS}}(t) \otimes \delta(x_1, x_2, x_3, t) \, dt;$$

$$n_{3,P_{mS}}(t) = \int_{C_{3,P_{mS}}} N_{3,P_{mS}}(t) \otimes \delta(x_1, x_2, x_3, t) \, dt;$$

$$a^{RBC}_{3,P_{mS}}(t) = \int_{C_{3,P_{mS}}} a_{3,P_{mS}}(t) \otimes \delta(x_1, x_2, x_3, t) \, dt$$

In a preferred embodiment, the invention provides an analytical solution of the Navier-Stocks equations in the region $O_{P_{aS}}$ of the apical Septum. FIG. 30 shows a rendering of these solutions in the mathlab software.

FIG. 29, illustrates mechanical parameters of blood induced by $Q_{P_{aS}}$ in the region $O_{P_{aS}}$ related to apical Lateral. The surface parameters are as follows $$F_{P_{aS}}((y_1, y_2, y_3)) =$$
$$\left(\sum_{k,l} \varepsilon'_{rr_{P_k},P_l} dt\right) \cdot y_1^2 + \left(\sum_{k,l} \varepsilon'_{u_{P_k},P_l} dt\right) \cdot y_2^2 + \left(\sum_{k,l} \varepsilon'_{cc_{P_k},P_l} dt\right) \cdot y_3^2 - D_{P_{aS}}$$

In the region $O_{P_{aS}}$, let $\phi_{1,P_{aS}}(t)$, $\phi_{2,P_{aS}}(t)$ and $\phi_{3,P_{aS}}(t)$ are parameterized forms of the projections of the surface $F_{P_{aS}}$ on xy-axis, xz-axis and yz-axis:

$$\varphi_{1,P_{aS}}(t) = \left(t, \left(\left(D_{P_{aS}} - \left(\sum_{k,l} \varepsilon'_{rr_{P_k},P_l} dt\right)t^2\right) \bigg/ \left(\sum_{k,l} \varepsilon'_{u_{P_k},P_l} dt\right)\right)^{\frac{1}{2}}\right);$$

$$\varphi_{2,P_{aS}}(t) = \left(t, \left(\left(D_{P_{aS}} - \left(\sum_{k,l} \varepsilon'_{rr_{P_k},P_l} dt\right)t^2\right) \bigg/ \left(\sum_{k,l} \varepsilon'_{cc_{P_k},P_l} dt\right)\right)^{\frac{1}{2}}\right);$$

$$\varphi_{3,P_{aS}}(t) = \left(t, \left(\left(D_{P_{aS}} - \left(\sum_{k,l} \varepsilon'_{u_{P_k},P_l} dt\right)t^2\right) \bigg/ \left(\sum_{k,l} \varepsilon'_{cc_{P_k},P_l} dt\right)\right)^{\frac{1}{2}}\right)$$

Following formulae were set;

$$T_{1,P_{aS}}(t) = \phi_{1,P_{aS}}(t)' / |\phi_{1,P_{aS}}(t)'|;$$

$$S_{1,P_{aS}} = \int_{t_o}^{t} \varphi_{1,P_{aS}}(u)' \, du;$$

$$\kappa_{1,P_{aS}}(t) \cdot N_{1,P_{aS}}(t) = \frac{dT_{1,P_{aS}}}{ds};$$

$$\kappa_{1,P_{aS}}(t) =$$
$$\left(\left(\left(D_{P_{aS}} - \left(\sum_{k,l} \varepsilon'_{rr_{P_k},P_l} dt\right)t^2\right) \bigg/ \left(\sum_{k,l} \varepsilon'_{u_{P_k},P_l} dt\right)\right)^{\frac{1}{2}}\right) - 0 \bigg/ S'^{3}_{1,P_{aS}};$$

$$a_{1,P_{aS}}(t) = S_{1,P_{aS}} \cdot T_{1,P_{aS}}(t) + \kappa_{1,P_{aS}}(t) \cdot N_{1,P_{aS}}(t)$$

$$T_{2,P_{aS}}(t) = \phi_{2,P_{aS}}(t)' / |\phi_{2,P_{aS}}(t)'|;$$

$$S_{2,P_{aS}} = \int_{t_o}^{t} \varphi_{2,P_{aS}}(u)' \, du;$$

$$\kappa_{2,P_{aS}}(t) \cdot N_{2,P_{aS}}(t) = \frac{dT_{2,P_{aS}}}{ds};$$

$$\kappa_{2,P_{aS}}(t) =$$

$$\left(\left(\left(D_{P_{aS}} - \left(\sum_{k,l} \varepsilon'_{rr_{P_k,P_l}} dt\right)^{\!2}\right)\!\middle/\!\left(\sum_{k,l} \varepsilon'_{cc_{P_k,P_l}} dt\right)\right)^{\!\frac{1}{2}}\right) - 0 \Big/ S'^3_{2,P_{aS}};$$

$$a_{2,P_{aS}}(t) = S_{2,P_{aS}}'' \cdot T_{2,P_{aS}}(t) + \kappa_{2,P_{aS}}(t) \cdot N_{2,P_{aS}}(t)$$

$$T_{3,P_{aS}}(t) = \phi_{3,P_{aS}}(t)' / |\phi_{3,P_{aS}}(t)'|;$$

$$S_{3,P_{aS}} = \int_{t_0}^{t} \varphi_{3,P_{aS}}(u)' \, du;$$

$$\kappa_{3,P_{aS}}(t) \cdot N_{3,P_{aS}}(t) = \frac{dT_{2,P_{aS}}}{ds};$$

$$\kappa_{3,P_{aS}}(t) =$$

$$\left(\left(\left(D_{P_{aS}} - \left(\sum_{k,l} \varepsilon'_{u_{P_k,P_l}} dt\right)^{\!2}\right)\!\middle/\!\left(\sum_{k,l} \varepsilon'_{u_{P_k,P_l}} dt\right)\right)^{\!\frac{1}{2}}\right) - 0 \Big/ S'^3_{3,P_{aS}};$$

$$a_{3,P_{aS}}(t) = S_{3,P_{aS}}'' \cdot T_{3,P_{aS}}(t) + \kappa_{3,P_{aS}}(t) \cdot N_{3,P_{aS}}(t)$$

$(x_1, x_2, x_3, t)$ is the coordinate system of the red blood cell in a neighbourhood $O_{P_{aS}}$ of the apical Septum and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{aS}}$, $C_{2,P_{aS}}$ and $C_{3,P_{aS}}$ are the graphs of $\phi_{1,P_{aS}}(t)$, $\phi_{2,P_{aS}}(t)$ and $\phi_{3,P_{aS}}(t)$ respectively then the mechanical parameters of the red blood cells in the region $O_{P_{aS}}$ are calculated by the following formulae:

$$v_{1,P_{aS}}(t) = \int_{C_{1,P_{aS}}} T_{1,P_{aS}}(t) \otimes \delta(x_1, x_2, x_3, t) \, dt;$$

$$n_{1,P_{aS}}(t) = \int_{C_{1,P_{aS}}} N_{1,P_{aS}}(t) \otimes \delta(x_1, x_2, x_3, t) \, dt;$$

$$a^{RBC}_{1,P_{aS}}(t) = \int_{C_{1,P_{aS}}} a_{1,P_{aS}}(t) \otimes \delta(x_1, x_2, x_3, t) \, dt$$

$$v_{2,P_{aS}}(t) = \int_{C_{2,P_{aS}}} T_{2,P_{aS}}(t) \otimes \delta(x_1, x_2, x_3, t) \, dt;$$

$$n_{2,P_{aS}}(t) = \int_{C_{2,P_{aS}}} N_{2,P_{aS}}(t) \otimes \delta(x_1, x_2, x_3, t) \, dt;$$

$$a^{RBC}_{2,P_{aS}}(t) = \int_{C_{2,P_{aS}}} a_{2,P_{aS}}(t) \otimes \delta(x_1, x_2, x_3, t) \, dt$$

$$v_{3,P_{aS}}(t) = \int_{C_{3,P_{aS}}} T_{3,P_{aS}}(t) \otimes \delta(x_1, x_2, x_3, t) \, dt;$$

$$n_{3,P_{aS}}(t) = \int_{C_{3,P_{aS}}} N_{3,P_{aS}}(t) \otimes \delta(x_1, x_2, x_3, t) \, dt;$$

$$a^{RBC}_{3,P_{aS}}(t) = \int_{C_{3,P_{aS}}} a_{3P_{aS}}(t) \otimes \delta(x_1, x_2, x_3, t) \, dt$$

In a preferred embodiment, the invention provides an analytical solution of the Navier-Stocks equations in the region $O_{P_{bS}}$ of the base Septum. FIG. 34 shows a rendering of these solutions in the mathlab software.

Figure 33:
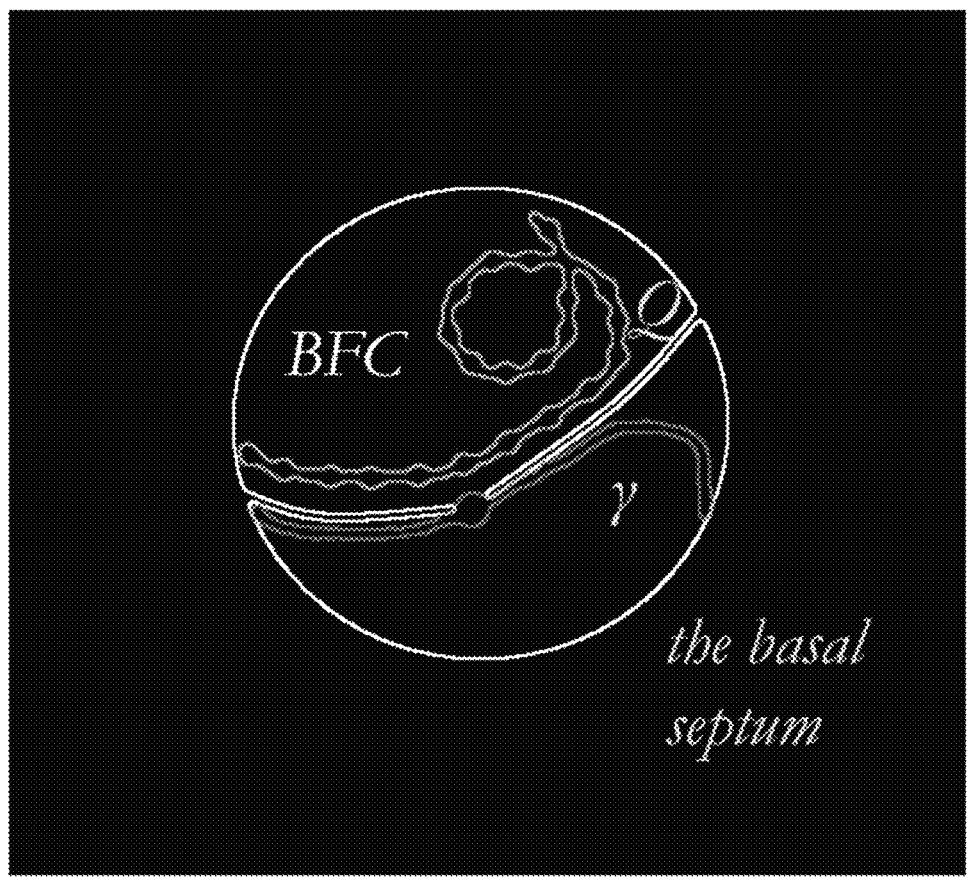
FIG. 33 shows the blood flow curve near the corresponded neighborhood of the basal Septum in the myocardium of the left ventricle where has been rendered at Mathlab software.
Figure 35:
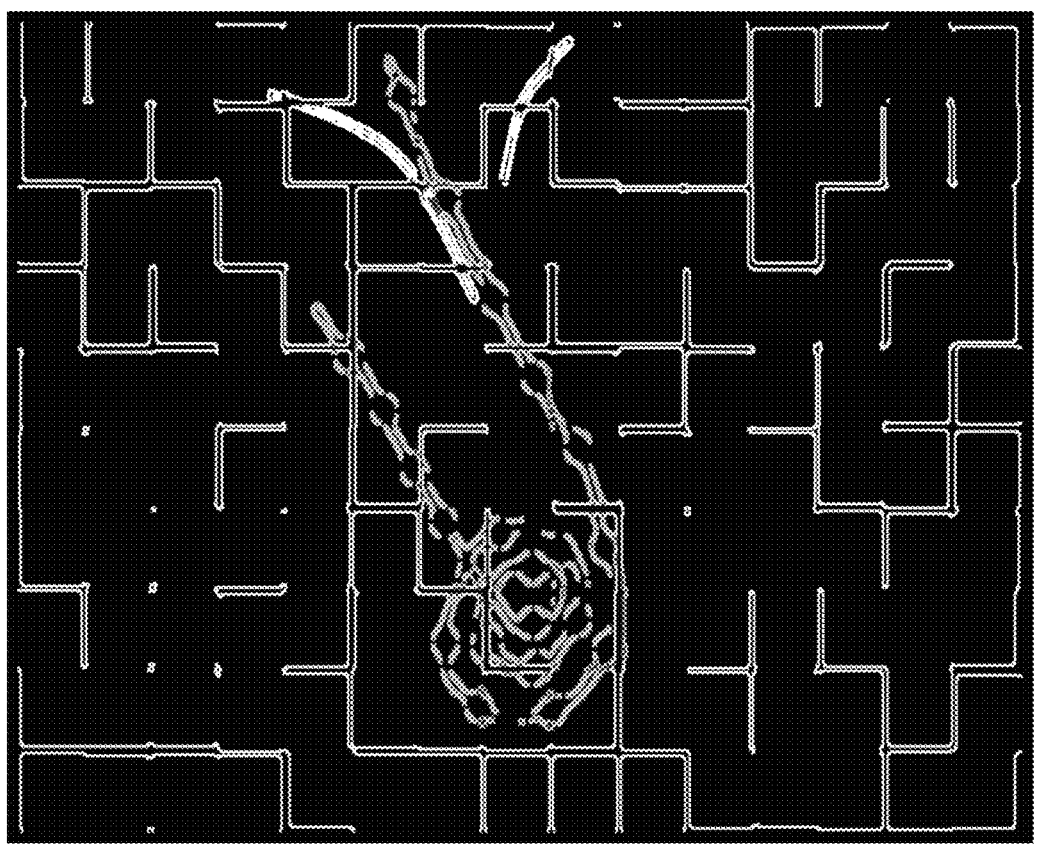
FIG. 35 shows the 2-D blood flow curve view in the Mathlab software.
Figure 36:
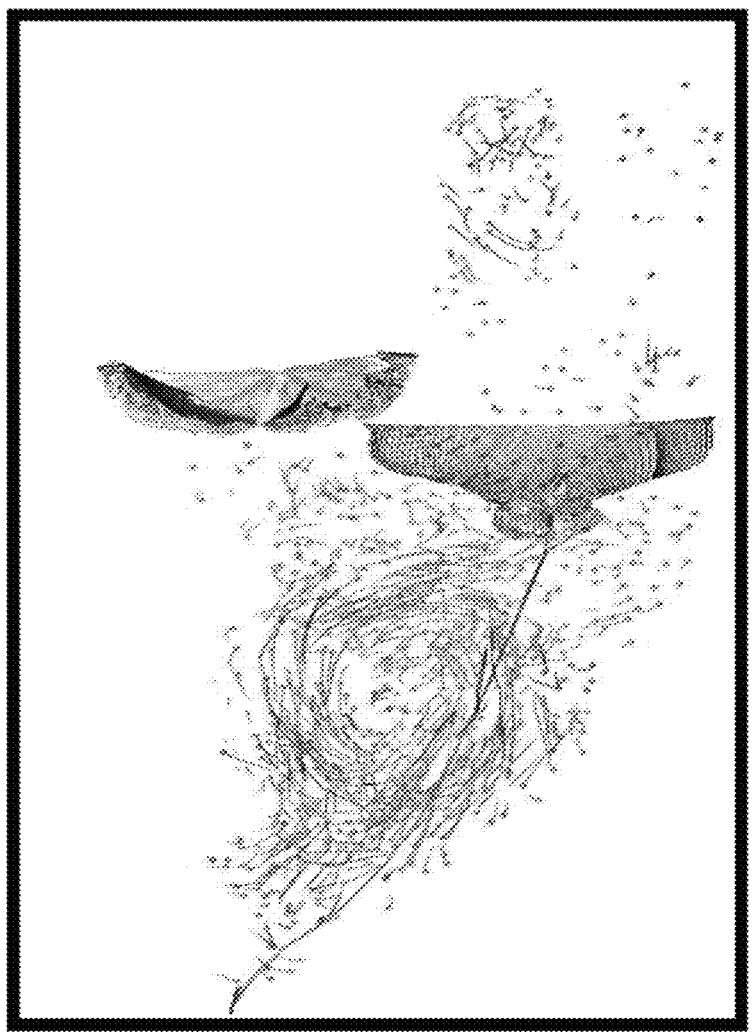
FIG. 36 shows the flow of the blood inside the left ventricle related to the other works.
Figure 40:
FIG. 40 shows the blood flow curve after the best prosthetic Mitral valve replacement.

FIG. 33, illustrates mechanical parameters of blood induced by $Q_{P_{bS}}$ in the region $O_{P_{bS}}$ related to mid Lateral. The surface parameters are as follows $$F_{P_{bS}}((y_1, y_2, y_3)) =$$

$$\left(\sum_{k,l} \varepsilon'_{rr_{P_k,P_l}} dt\right) \cdot y_1^2 + \left(\sum_{k,l} \varepsilon'_{u_{P_k,P_l}} dt\right) \cdot y_2^2 + \left(\sum_{k,l} \varepsilon'_{cc_{P_k,P_l}} dt\right) \cdot y_3^2 - D_{P_{bS}}$$

In the region $O_{P_{bS}}$, let $\phi_{1,P_{bS}}(t)$, $\phi_{2,P_{bS}}(t)$ and $\phi_{3,P_{bS}}(t)$ are parameterized forms of the projections of the surface $F_{P_{bS}}$ on xy-axis, xz-axis and yz-axis:

$$\varphi_{1,P_{bS}}(t) = \left(t, \left(\left(D_{P_{bS}} - \left(\sum_{k,l} \varepsilon'_{rr_{P_k,P_l}} dt\right)^{\!2}\right)\!\middle/\!\left(\sum_{k,l} \varepsilon'_{u_{P_k,P_l}} dt\right)\right)^{\!\frac{1}{2}}\right);$$

$$\varphi_{2,P_{bS}}(t) = \left(t, \left(\left(D_{P_{mS}} - \left(\sum_{k,l} \varepsilon'_{rr_{P_k,P_l}} dt\right)^{\!2}\right)\!\middle/\!\left(\sum_{k,l} \varepsilon'_{cc_{P_k,P_l}} dt\right)\right)^{\!\frac{1}{2}}\right);$$

$$\varphi_{3,P_{bS}}(t) = \left(t, \left(\left(D_{P_{bS}} - \left(\sum_{k,l} \varepsilon'_{u_{P_k,P_l}} dt\right)^{\!2}\right)\!\middle/\!\left(\sum_{k,l} \varepsilon'_{cc_{P_k,P_l}} dt\right)\right)^{\!\frac{1}{2}}\right)$$

Following formulae were set;

$$T_{1,P_{bS}}(t) = \phi_{1,P_{bS}}(t)' / |\phi_{1,P_{bS}}(t)'|;$$

$$S_{1,P_{bS}} = \int_{t_0}^{t} \varphi_{1,P_{bS}}(u)' \, du;$$

$$\kappa_{1,P_{bS}}(t) \cdot N_{1,P_{bS}}(t) = \frac{dT_{1,P_{bS}}}{ds};$$

$$\kappa_{1,P_{bS}}(t) =$$

$$\left(\left(\left(D_{P_{bS}} - \left(\sum_{k,l} \varepsilon'_{rr_{P_k,P_l}} dt\right)^{\!2}\right)\!\middle/\!\left(\sum_{k,l} \varepsilon'_{u_{P_k,P_l}} dt\right)\right)^{\!\frac{1}{2}}\right) - 0 \Big/ S'^3_{1,P_{bS}};$$

$$a_{1,P_{bS}}(t) = S_{1,P_{bS}}'' \cdot T_{1,P_{bS}}(t) + \kappa_{1,P_{bS}}(t) \cdot N_{1,P_{bS}}(t)$$

$$T_{2,P_{bS}}(t) = \phi_{2,P_{bS}}(t)' / |\phi_{2,P_{bS}}(t)'|;$$

$$S_{2,P_{bS}} = \int_{t_0}^{t} \varphi_{2,P_{bS}}(u)' \, du;$$

$$\kappa_{2,P_{bS}}(t) \cdot N_{2,P_{bS}}(t) = \frac{dT_{2,P_{bS}}}{ds};$$

$$\kappa_{2,P_{bS}}(t) =$$

$$\left(\left(\left(D_{P_{bS}} - \left(\sum_{k,l} \varepsilon'_{rr_{P_k,P_l}} dt\right)^{\!2}\right)\!\middle/\!\left(\sum_{k,l} \varepsilon'_{cc_{P_k,P_l}} dt\right)\right)^{\!\frac{1}{2}}\right) - 0 \Big/ S'^3_{2,P_{bS}};$$

$$a_{2,P_{bS}}(t) = S_{2,P_{bS}}'' \cdot T_{2,P_{bS}}(t) + \kappa_{2,P_{bS}}(t) \cdot N_{2,P_{bS}}(t)$$

$$T_{3,P_{bS}}(t) = \phi_{3,P_{bS}}(t)' / |\phi_{3,P_{bS}}(t)'|;$$

$$S_{3,P_{bS}} = \int_{t_o}^{t} \varphi_{3,P_{bS}}(u)' \, du;$$

$$\kappa_{3,P_{bS}}(t) \cdot N_{3,P_{bS}}(t) = \frac{dT_{2,P_{bS}}}{ds};$$

$$\kappa_{3,P_{bS}}(t) = \left(\left(\left(D_{P_{bS}} - \left(\sum_{k,l} \varepsilon'_{u_{P_k,P_l}} dt\right)t^2\right) \middle/ \left(\sum_{k,l} \varepsilon'_{u_{P_k,P_l}} dt\right)\right)^{\frac{1}{2}}\right) - 0 \big/ S'^3_{3,P_{bS}};$$

$$a_{3,P_{bS}}(t) = S_{3,P_{bS}} \cdot T_{3,P_{bS}}(t) + \kappa_{3,P_{bS}}(t) \cdot N_{3,P_{bS}}(t)$$

Following formulae were set;

$$T_{1,P_{bS}}(t) = \phi_{1,P_{bS}}(t)' / |\phi_{1,P_{bS}}(t)'|;$$

$$S_{1,P_{bS}} = \int_{t_o}^{t} \varphi_{1,P_{bS}}(u)' \, du;$$

$$\kappa_{1,P_{bS}}(t) \cdot N_{1,P_{bS}}(t) = \frac{dT_{1,P_{bS}}}{ds};$$

$$\kappa_{1,P_{bS}}(t) = \left(\left(\left(D_{P_{bS}} - \left(\sum_{k,l} \varepsilon'_{rr_{P_k,P_l}} dt\right)t^2\right) \middle/ \left(\sum_{k,l} \varepsilon'_{u_{P_k,P_l}} dt\right)\right)^{\frac{1}{2}}\right) - 0 \big/ S'^3_{1,P_{bS}};$$

$$a_{1,P_{bS}}(t) = S_{1,P_{bS}}'' \cdot T_{1,P_{bS}}(t) + \kappa_{1,P_{bS}}(t) \cdot N_{1,P_{bS}}(t)$$

$$T_{2,P_{bS}}(t) = \phi_{2,P_{bS}}(t)' / |\phi_{2,P_{bS}}(t)'|;$$

$$S_{2,P_{bS}} = \int_{t_o}^{t} \varphi_{2,P_{bS}}(u)' \, du;$$

$$\kappa_{2,P_{bS}}(t) \cdot N_{2,P_{bS}}(t) = \frac{dT_{2,P_{bS}}}{ds};$$

$$\kappa_{2,P_{bS}}(t) = \left(\left(\left(D_{P_{bS}} - \left(\sum_{k,l} \varepsilon'_{rr_{P_k,P_l}} dt\right)t^2\right) \middle/ \left(\sum_{k,l} \varepsilon'_{cc_{P_k,P_l}} dt\right)\right)^{\frac{1}{2}}\right) - 0 \big/ S'^3_{2,P_{bS}};$$

$$a_{2,P_{bS}}(t) = S_{2,P_{bS}}'' \cdot T_{2,P_{bS}}(t) + \kappa_{2,P_{bS}}(t) \cdot N_{2,P_{bS}}(t)$$

$$T_{3,P_{bS}}(t) = \phi_{3,P_{bS}}(t)' / |\phi_{3,P_{bS}}(t)'|;$$

$$S_{3,P_{bS}} = \int_{t_o}^{t} \varphi_{3,P_{bS}}(u)' \, du;$$

$$\kappa_{3,P_{bS}}(t) \cdot N_{3,P_{bS}}(t) = \frac{dT_{2,P_{bS}}}{ds};$$

-continued $$\kappa_{3,P_{bS}}(t) = \left(\left(\left(D_{P_{bS}} - \left(\sum_{k,l} \varepsilon'_{u_{P_k,P_l}} dt\right)t^2\right) \middle/ \left(\sum_{k,l} \varepsilon'_{u_{P_k,P_l}} dt\right)\right)^{\frac{1}{2}}\right) - 0 \big/ S'^3_{3,P_{bS}};$$

$$a_{3,P_{bS}}(t) = S_{3,P_{bS}} \cdot T_{3,P_{bS}}(t) + \kappa_{3,P_{bS}}(t) \cdot N_{3,P_{bS}}(t)$$

$(x_1, x_2, x_3, t)$ is the coordinate system of the red blood cell in a neighbourhood $O_{P_{bS}}$ of the basal Septum and $\delta(x_1, x_2, x_3, t) = \delta^*(x_1, t) \cdot \delta^*(x_2, t) \cdot \delta^*(x_3, t)$ where $\delta^*$ is the dirac function and $C_{1,P_{bS}}$, $C_{2,P_{bS}}$ and $C_{3,P_{bS}}$ are the graphs of $\phi_{1,P_{bS}}(t)$, $\phi_{2,P_{bS}}(t)$ and $\phi_{3,P_{bS}}(t)$ respectively then the mechanical parameters of the red blood cells in the region $O_{P_{bS}}$ are calculated by the following formulae:

$$v_{1,P_{bS}}(t) = \int_{C_{1,P_{bS}}} T_{1,P_{bS}}(t) \otimes \delta(x_1, x_2, x_3, t) d\tau;$$

$$n_{1,P_{bS}}(t) = \int_{C_{1,P_{bS}}} N_{1,P_{bS}}(t) \otimes \delta(x_1, x_2, x_3, t) d\tau;$$

$$a_{1,P_{bS}}^{RBC}(t) = \int_{C_{1,P_{bS}}} a_{1,P_{bS}}(t) \otimes \delta(x_1, x_2, x_3, t) dt$$

$$v_{2,P_{bS}}(t) = \int_{C_{2,P_{bS}}} T_{2,P_{bS}}(t) \otimes \delta(x_1, x_2, x_3, t) d\tau;$$

$$n_{2,P_{bS}}(t) = \int_{C_{2,P_{bS}}} N_{2,P_{bS}}(t) \otimes \delta(x_1, x_2, x_3, t) d\tau;$$

$$a_{2,P_{bS}}^{RBC}(t) = \int_{C_{2,P_{bS}}} a_{2,P_{bS}}(t) \otimes \delta(x_1, x_2, x_3, t) dt$$

$$v_{3,P_{bS}}(t) = \int_{C_{3,P_{bS}}} T_{3,P_{bS}}(t) \otimes \delta(x_1, x_2, x_3, t) d\tau;$$

$$n_{3,P_{bS}}(t) = \int_{C_{3,P_{bS}}} N_{3,P_{bS}}(t) \otimes \delta(x_1, x_2, x_3, t) d\tau;$$

$$a_{3,P_{bS}}^{RBC}(t) = \int_{C_{3,P_{bS}}} a_{3,P_{bS}}(t) \otimes \delta(x_1, x_2, x_3, t) dt$$

In an embodiment, the invention provides method for regionally making blood flow curve as described below;

For apical Anterior:

Setting $v_{P_{aA}}(t) = (v_{1,P_{aA}}(t), v_{2,P_{aA}}(t), v_{3,P_{aA}}(t))$ as field velocity vectors of the blood in region $O_{P_{aA}}$, field of displacements in the real time at the same region is obtained by:

$$r_{P_{aA}}(t,s) = \left(t, \int_{t_o}^{s} v_{1,P_{aA}}(u) du, \int_{t_o}^{s} v_{2,P_{aA}}(u) du, \int_{t_o}^{s} v_{3,P_{aA}}(u) du\right)$$

If, algebraic form of $r_{P_{aA}}$ is called as $BFC_{P_{aA}}((x_1, x_2, x_3, t))$ then $$X_{P_{aA}} = \text{Spec}\left(\frac{R[x_1, x_2, x_3, t]}{BFC_{P_{aA}}((x_1, x_2, x_3, t))}\right)$$

Similarly,

For mid Anterior

Setting $v_{P_{mA}}(t) = (v_{1,P_{mA}}(t), v_{2,P_{mA}}(t), v_{3,P_{mA}}(t))$ as field velocity vectors of the blood in region $O_{P_{mA}}$, field of displacements in the real time at the same region is obtained by:

$$r_{P_{mA}}(t, s) = \left(t, \int_{t_o}^{s} v_{1,P_{mA}}(u)du, \int_{t_o}^{s} v_{2,P_{mA}}(u)du, \int_{t_o}^{s} v_{3,P_{mA}}(u)du\right)$$

If, algebraic form of $r_{P_{mA}}$ is called as $BFC_{P_{mA}}((x_1,x_2,x_3, t))$ then $$X_{P_{mA}} = \text{Spec}\left(\frac{R[x_1, x_2, x_3, t]}{BFC_{P_{mA}}((x_1, x_2, x_3, t))}\right)$$

For basal Anterior
Setting $v_{P_{bA}}(t)=(v_{1,P_{bA}}(t), v_{2,P_{bA}}(t), v_{3,P_{bA}}(t))$ as field velocity vectors of the blood in region $O_{P_{bA}}$, field of displacements in the real time at the same region is obtained by:

$$r_{P_{bA}}(t, s) = \left(t, \int_{t_o}^{s} v_{1,P_{bA}}(u)du, \int_{t_o}^{s} v_{2,P_{bA}}(u)du, \int_{t_o}^{s} v_{3,P_{bA}}(u)du\right)$$

If, algebraic form of $r_{P_{bA}}$ is called as $BFC_{P_{bA}}((x_1,x_2,x_3, t))$ then $$X_{P_{bA}} = \text{Spec}\left(\frac{R[x_1, x_2, x_3, t]}{BFC_{P_{bA}}((x_1, x_2, x_3, t))}\right)$$

For the apical inferior
Setting $v_{P_{aI}}(t)=(v_{1,P_{aI}}(t), v_{2,P_{aI}}(t), v_{3,P_{aI}}(t))$ as field velocity vectors of the blood in region $O_{P_{aI}}$, field of displacements in the real time at the same region is obtained by:

$$r_{P_{aI}}(t, s) = \left(t, \int_{t_o}^{s} v_{1,P_{aI}}(u)du, \int_{t_o}^{s} v_{2,P_{aI}}(u)du, \int_{t_o}^{s} v_{3,P_{aI}}(u)du\right)$$

If, algebraic form of $r_{P_{aI}}$ is called as $BFC_{P_{aI}}((x_1,x_2,x_3, t))$ then $$X_{P_{aI}} = \text{Spec}\left(\frac{R[x_1, x_2, x_3, t]}{BFC_{P_{aI}}((x_1, x_2, x_3, t))}\right)$$

Similarly,
For mid Inferior
Setting $v_{P_{mI}}(t)=(v_{1,P_{mI}}(t), v_{2,P_{mI}}(t), v_{3,P_{mI}}(t))$ as field velocity vectors of the blood in region $O_{P_{mI}}$, field of displacements in the real time at the same region is obtained by:

$$r_{P_{mI}}(t, s) = \left(t, \int_{t_o}^{s} v_{1,P_{mI}}(u)du, \int_{t_o}^{s} v_{2,P_{mI}}(u)du, \int_{t_o}^{s} v_{3,P_{mI}}(u)du\right)$$

If, algebraic form of $r_{P_{mI}}$ is called as $BFC_{P_{mI}}((x_1,x_2,x_3, t))$ then $$X_{P_{mI}} = \text{Spec}\left(\frac{R[x_1, x_2, x_3, t]}{BFC_{P_{mI}}((x_1, x_2, x_3, t))}\right)$$

For basal Inferior
Setting $v_{P_{bI}}(t)=(v_{1,P_{bI}}(t), v_{2,P_{bI}}(t), v_{3,P_{bI}}(t))$ as field velocity vectors of the blood in region $O_{P_{bI}}$, field of displacements in the real time at the same region is obtained by:

$$r_{P_{bI}}(t, s) = \left(t, \int_{t_o}^{s} v_{1,P_{bI}}(u)du, \int_{t_o}^{s} v_{2,P_{bI}}(u)du, \int_{t_o}^{s} v_{3,P_{bI}}(u)du\right)$$

If, algebraic form of $r_{P_{bI}}$ is called as $BFC_{P_{bI}}((x_1,x_2,x_3, t))$ then $$X_{P_{bI}} = \text{Spec}\left(\frac{R[x_1, x_2, x_3, t]}{BFC_{P_{bI}}((x_1, x_2, x_3, t))}\right)$$

For the apical Lateral
Setting $v_{P_{aL}}(t)=(v_{1,P_{aL}}(t), v_{2,P_{aL}}(t), v_{3,P_{aL}}(t))$ as field velocity vectors of the blood in region $O_{P_{aL}}$, field of displacements in the real time at the same region is obtained by:

$$r_{P_{aL}}(t, s) = \left(t, \int_{t_o}^{s} v_{1,P_{aL}}(u)du, \int_{t_o}^{s} v_{2,P_{aL}}(u)du, \int_{t_o}^{s} v_{3,P_{aL}}(u)du\right)$$

If, algebraic form of $r_{P_{aL}}$ is called as $BFC_{P_{aL}}((x_1,x_2,x_3, t))$ then $$X_{P_{aL}} = \text{Spec}\left(\frac{R[x_1, x_2, x_3, t]}{BFC_{P_{aL}}((x_1, x_2, x_3, t))}\right)$$

Similarly,
For mid Lateral
Setting $v_{P_{mL}}(t)=(v_{1,P_{mL}}(t), v_{2,P_{mL}}(t), v_{3,P_{mL}}(t))$ as field velocity vectors of the blood in region $O_{P_{mL}}$, field of displacements in the real time at the same region is obtained by:

$$r_{P_{mL}}(t, s) = \left(t, \int_{t_o}^{s} v_{1,P_{mL}}(u)du, \int_{t_o}^{s} v_{2,P_{mL}}(u)du, \int_{t_o}^{s} v_{3,P_{mL}}(u)du\right)$$

If, algebraic form of $r_{P_{mL}}$ is called as $BFC_{P_{mL}}((x_1,x_2,x_3, t))$ then $$X_{P_{mL}} = \text{Spec}\left(\frac{R[x_1, x_2, x_3, t]}{BFC_{P_{mL}}((x_1, x_2, x_3, t))}\right)$$

For basal Lateral
Setting $v_{P_{bL}}(t)=(v_{1,P_{bL}}(t), v_{2,P_{bL}}(t), v_{3,P_{bL}}(t))$ as field velocity vectors of the blood in region $O_{P_{bL}}$, field of displacements in the real time at the same region is obtained by:

$$r_{P_{bL}}(t, s) = \left(t, \int_{t_o}^{s} v_{1,P_{bL}}(u)du, \int_{t_o}^{s} v_{2,P_{bL}}(u)du, \int_{t_o}^{s} v_{3,P_{bL}}(u)du\right)$$

If, algebraic form of $r_{P_{bL}}$ is called as $BFC_{P_{bL}}((x_1,x_2,x_3, t))$ then $$X_{P_{bL}} = \text{Spec}\left(\frac{R[x_1, x_2, x_3, t]}{BFC_{P_{bL}}((x_1, x_2, x_3, t))}\right)$$

For the apical Septum

Setting $v_{P_{aS}}(t)=(v_{1,P_{aS}}(t), v_{2,P_{aS}}(t), v_{3,P_{aS}}(t))$ as field velocity vectors of the blood in region $O_{P_{aS}}$, field of displacements in the real time at the same region is obtained by:

$$r_{P_{aS}}(t, s) = \left(t, \int_{t_0}^{s} v_{1,P_{aS}}(u)du, \int_{t_0}^{s} v_{2,P_{aS}}(u)du, \int_{t_0}^{s} v_{3,P_{aS}}(u)du\right)$$

If, algebraic form of $r_{P_{aS}}$ is called as $BFC_{P_{aS}}((x_1,x_2,x_3, t))$ then $$X_{P_{aS}} = \text{Spec}\left(\frac{R[x_1, x_2, x_3, t]}{BFC_{P_{aS}}((x_1, x_2, x_3, t))}\right)$$

Similarly,
For mid Septum
Setting $v_{P_{mS}}(t)=(v_{1,P_{mS}}(t), v_{2,P_{mS}}(t), v_{3,P_{mS}}(t))$ as field velocity vectors of the blood in region $O_{P_{mS}}$, field of displacements in the real time at the same region is obtained by:

$$r_{P_{mS}}(t, s) = \left(t, \int_{t_0}^{s} v_{1,P_{mS}}(u)du, \int_{t_0}^{s} v_{2,P_{mS}}(u)du, \int_{t_0}^{s} v_{3,P_{mS}}(u)du\right)$$

If, algebraic form of $r_{P_{mS}}$ is called as $BFC_{P_{mS}}((x_1,x_2,x_3, t))$ then $$X_{P_{mS}} = \text{Spec}\left(\frac{R[x_1, x_2, x_3, t]}{BFC_{P_{mS}}((x_1, x_2, x_3, t))}\right)$$

For basal Septum
Setting $v_{P_{bS}}(t)=(v_{1,P_{bS}}(t), v_{2,P_{bS}}(t), v_{3,P_{bS}}(t))$ as field velocity vectors of the blood in region $O_{P_{bS}}$, field of displacements in the real time at the same region is obtained by:

$$r_{P_{bS}}(t, s) = \left(t, \int_{t_0}^{s} v_{1,P_{bS}}(u)du, \int_{t_0}^{s} v_{2,P_{bS}}(u)du, \int_{t_0}^{s} v_{3,P_{bS}}(u)du\right)$$

If, algebraic form of $r_{P_{bS}}$ is called as $BFC_{P_{bS}}((x_1,x_2,x_3, t))$ then $$X_{P_{bS}} = \text{Spec}\left(\frac{R[x_1, x_2, x_3, t]}{BFC_{P_{bS}}((x_1, x_2, x_3, t))}\right)$$

The scheme of blood flow curve is as below $$X_{Blood\,flow\,in\,LV} = X_{P_{aA}} \cup X_{P_{mA}} \cup X_{P_{bA}} \cup X_{P_{aI}} \cup X_{P_{mI}} \cup X_{P_{bI}} \cup X_{P_{aL}} \cup X_{P_{mL}} \cup X_{P_{bL}} \cup X_{P_{aS}} \cup X_{P_{mS}} \cup X_{P_{bS}}$$

We claim:

1. A computer implemented method for solving the Navier-Stokes equation of blood dynamics for studying blood flow curves combined with regional blood flow and contrasted with echocardiography samples along with blood flows globally inside the left ventricle comprising:
   A processor to perform the steps of:
   modeling myocardial motion in an elastic membrane by analyzing blood flow curves to determine regional blood flow near echocardiography samples and global blood flow inside the left ventricle, and wherein the echocardiography samples are collected from anterior, inferior, lateral and septum regions of the left ventricle to calculate the mechanical parameters of blood near the echocardiography samples to model heart diseases using echocardiography.

2. The method according to claim 1, wherein the method comprises:
   a. calculating the mechanical parameters of blood near the echocardiography samples numerically, and wherein the mechanical parameters of blood comprise strain components, velocity, filed velocity vector of blood, unit velocity vector of blood, unit normal vector of blood and gravity vector of blood;
   b. calculating the myofiber curve for echocardiography samples of step (a);
   c. calculating the quadratic equation for the curve of step (b) for each echocardiography samples;
   d. determining the blood flow curve from step (c) for each echocardiography samples and;
   e. integrating the blood flow curves of step (d) for determining blood flow curve for left ventricle globally.

3. The method as claimed in claim 1, wherein anterior samples are collected from apical, mid and basal regions of the anterior region of the left ventricle.

4. The method as claimed in claim 1, wherein anterior samples are collected from apical, mid and basal regions of the inferior region of the left ventricle.

5. The method as claimed in claim 1, wherein anterior samples are collected from apical, mid and basal regions of the lateral region of the left ventricle.

6. The method as claimed in claim 1, wherein anterior samples are collected from apical, mid and basal regions of the septum of the left ventricle.

7. An echocardiography system for solving the Navier-Stokes equation of blood dynamics comprising:
   a processor in which equations and echocardiography samples are inputted for solving the Navier-Stokes equation of blood dynamics to generate blood flow curves of the blood flowing regionally near the echocardiography samples and globally inside the left ventricle;
   wherein the echocardiography samples are collected from anterior, inferior, lateral and septum of the left ventricle and wherein anterior samples are collected from apical, mid and basal regions of septum.

8. The echocardiography system as claimed in claim 7, wherein the mechanical parameters of blood near echocardiography samples are calculated, and wherein the mechanical parameters of blood are strain components, velocity, filed velocity vector of blood, unit velocity vector of blood, unit normal vector of blood and gravity vector of blood.

9. The echocardiography system as claimed in claim 7, wherein anterior samples are collected from apical, mid and basal regions of the anterior and lateral regions of the left ventricle.

10. The echocardiography system as claimed in claim 7, wherein anterior samples are collected from apical, mid and basal regions of the inferior region of the left ventricle.

* * * * *